(12) United States Patent
Mews et al.

(10) Patent No.: US 12,077,527 B2
(45) Date of Patent: *Sep. 3, 2024

(54) COMPOSITIONS AND METHODS FOR INHIBITING ACSS2

(71) Applicant: THE TRUSTEES OF THE UNIVERSITY OF PENNSYLVANIA, Philadelphia, PA (US)

(72) Inventors: Philipp Mews, New York, NY (US); Shelley L Berger, Wayne, PA (US); Jeffrey D. Winkler, Wynnewood, PA (US); Andrew Glass, Philadelphia, PA (US); Simon David Peter Baugh, Ringoes, NJ (US)

(73) Assignee: The Trustees of the University of Pennsylvania, Pennsylvania, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/650,901

(22) PCT Filed: Sep. 26, 2018

(86) PCT No.: PCT/US2018/052839
§ 371 (c)(1),
(2) Date: Mar. 26, 2020

(87) PCT Pub. No.: WO2019/067528
PCT Pub. Date: Apr. 4, 2019

(65) Prior Publication Data
US 2020/0291005 A1    Sep. 17, 2020

Related U.S. Application Data

(60) Provisional application No. 62/563,148, filed on Sep. 26, 2017.

(51) Int. Cl.
 C07D 241/44    (2006.01)
 A61K 31/498    (2006.01)
 A61P 25/00     (2006.01)
 C07D 409/14    (2006.01)

(52) U.S. Cl.
 CPC ............ C07D 409/14 (2013.01); A61P 25/00 (2018.01)

(58) Field of Classification Search
 CPC ..... C07D 241/44; A61K 31/498; A61P 25/28; A61P 25/00; A61P 25/30; A61P 25/32; A61P 25/34; A61P 25/36
 USPC .......................................... 544/356; 514/249
 See application file for complete search history.

(56) References Cited

U.S. PATENT DOCUMENTS 8,993,758 B2 * 3/2015 Natarajan ............ C07D 401/14
                                                  548/266.4
9,434,701 B2    9/2016 Ferrie 2009/0163545 A1    6/2009 Goldfarb
2013/0085133 A1    4/2013 Severson
2013/0289041 A1   10/2013 Natarajan
2017/0152245 A1    6/2017 Huang

FOREIGN PATENT DOCUMENTS

WO    WO 2011-097607 A1 *  8/2011 ............. A61K 31/41

OTHER PUBLICATIONS

Crowe, A. et al.: High throughput screening for small molecule inhibitors of heparin-induced tau fibril formation. Biochem. & Biophys. Res. Commun., vol. 358, pp. 1-6, 2007.*
Rajule, R. et al.: Perturbing pro-survival proteins using quinoxaline derivatives: A structure-activity relationship study. Biorganic & Med. Chem., vol. 20, pp. 2227-2234, 2012.*
Compounds with RN 508185-73-7 and RN 709000-08-8.*
Ariyannur, P. S. et al., 2010, "Nuclear-cytoplasmic localization of acetyl coenzyme A synthetase-1 in the rat brain", J. Comp. Neurol., 518:2952-2977.
Balderas, I. et al., 2008, "The consolidation of object and context recognition memory involve different regions of the temporal lobe", Learn. Mem., 15:618-624.
Barrett, R. M. et al., 2011, "Hippocampal focal knockout of CBP affects specific histone modifications, long-term potentiation, and long-term memory", Neuropsychopharmacology, 36:1545-1556.
Bonthuis et al., 2015, "Noncanonical Genomic Imprinting Effects in Offspring", Cell Rep., 12:979-991.
Cai, L., et al., 2011, "Acetyl-CoA Induces Cell Growth and Proliferation by Promoting the Acetylation of Histones at Growth Genes", Mol. Cell, 42:426-437.
Cates et al., 2018, "Fosb Induction in Nucleus Accumbens by Cocaine Is Regulated by E2F3a", Biol. Psychiatry, 84:167-179.
Comerford, S. A. et al., 2014, "Acetate Dependence of Tumors", Cell, 159:1591-1602.
Egervari et al., 2018, "Shaping vulnerability to addiction—the contribution of behavior, neural circuits and molecular mechanisms", Neurosci. Biobehav. Rev., 85:117-125.
Gao, X. et al., 2016, "Acetate functions as an epigenetic metabolite to promote lipid synthesis under hypoxia", Nat. Commun., 7:11960.
Gräff, J. et al., 2012, "Dynamic histone marks in the hippocampus and cortex facilitate memory consolidation", Nat. Commun., 3:991.
Graff, J. et al., 2013, "Histone acetylation: molecular mnemonics on the chromatin", Nat. Rev. Neurosci., 14:97-111.
Gut, P. et al., 2013, "The nexus of chromatin regulation and intermediary metabolism", Nature, 502:489-498.
Kaelin, W. G. Jr. et al., 2013, "Influence of Metabolism on Epigenetics and Disease", Cell, 153:56-69.
Kandel, E. R. et al., 2014, "The Molecular and Systems Biology of Memory", Cell, 157:163-186.

(Continued)

*Primary Examiner* — Charanjit Aulakh
(74) *Attorney, Agent, or Firm* — Riverside Law LLP

(57) ABSTRACT

The present invention provides compositions and methods for inhibiting ACSS2 for modulating histone acetylation or for treating or preventing a neurological disease or disorder.

11 Claims, 43 Drawing Sheets

(56) References Cited

OTHER PUBLICATIONS

Katada, S., et al., 2012, "Connecting Threads: Epigenetics and Metabolism", Cell, 148:24-28.
Kim et al., 2006, "Acute in vivo effect of ethanol (binge drinking) on histone H3 modifications in rat tissues", Alcohol Alcohol., 41:126-132.
Korzus, E. et al., 2004, "CBP Histone Acetyltransferase Activity Is a Critical Component of Memory Consolidation", Neuron, 42:961-972.
Lein, E. S. et al., 2007, "Genome-wide atlas of gene expression in the adult mouse brain", Nature, 445:168-176.
Mamiya, N. et al., 2009, "Brain Region-Specific Gene Expression Activation Required for Reconsolidation and Extinction of Contextual Fear Memory", J. Neurosci., 29:402-413.
Mandal et al., 2017, "In Utero Alcohol Exposure and the Alteration of Histone Marks in the Developing Fetus: An Epigenetic Phenomenon of Maternal Drinking", Int. J. Biol. Sci., 13:1100-1108.
Maren, S. et al., 2000, "The hippocampus and contextual memory retrieval in Pavlovian conditioning", Behav. Brain Res., 110:97-108.
Mariño, G. et al., 2014, "Regulation of Autophagy by Cytosolic Acetyl-Coenzyme A", Mol. Cell, 53:710-725.
Mashimo, T. et al., 2014, "Acetate Is a Bioenergetic Substrate for Human Glioblastoma and Brain Metastases", Cell, 159:1603-1614.
Mews et al., "Acetyl-CoA synthetase regulates histone acetylation and hippocampal memory", Nature, (Jun. 15, 2017), vol. 546, pp. 381-386, XP055586593.
Mews et al., 2016, "Chapter Twelve—Exploring the Dynamic Relationship Between Cellular Meta bolism and Chromatin Structure Using SILAC-Mass Spec and ChIP-Sequencing", Methods Enzymol., 574:311-329.
Mews et al., 2017, "Cross-talk between the epigenome and neural circuits in drug addiction", Prog. Brain Res., 235:19-63.
Mulligan et al., 2011, "Molecular Profiles of Drinking Alcohol to Intoxication in C57BL/6J Mice", Alcohol. Clin. Exp. Res., 35:659-670.
Peixoto, L. L. et al., 2015, "Memory acquisition and retrieval impact different epigenetic processes that regulate gene expression", BMC Genomics, 16:S5.
Peleg, S. et al., 2010, "Altered Histone Acetylation Is Associated with Age-Dependent Memory Impairment in Mice", Science, 328:753-756.
Pietrocola, F. et al., 2015, "Acetyl Coenzyme A: A Central Metabolite and Second Messenger", Cell Metab., 21:805-821.
Poplawski, S. G. et al., 2014, "Object-location training elicits an overlapping but temporally distinct transcriptional profile from contextual fear conditioning", Neurobiol. Learn. Mem., 116:90-95.
Qi, Y. et al., 1997, "Characterization of a CNS Cell Line, CAD, in which Morphological Differentiation Is Initiated by Serum Deprivation", J. Neurosci., 17:1217-1225.
Ribeiro et al., "Possible involvement of ACSS2 gene in alcoholism", J. Neural. Transm., (May 26, 2017), XP036302290.
Robinson et al., 2011, "Transcriptional and Epigenetic Mechanisms of Addiction", Nat. Rev. Neurosci., 12:623-637.
Rogers, J. L. et al., 2006, "EVects of ventral and dorsal CA1 subregional lesions on trace fear conditioning", Neurobiol. Learn. Mem., 86:72-81.
Ron et al., 2016, "Molecular mechanisms underlying alcohol-drinking behaviours", Nat. Publ. Gr., 17:576-591.
Sardi, S. P. et al., 2006, "Presenilin-Dependent ErbB4 Nuclear Signaling Regulates the Timing of Astrogenesis in the Developing Brain", Cell, 127:185-197.
Sarkola et al., 2002, "Ethanol, Acetaldehyde, Acetate, and Lactate Levels After Alcohol Intake in White Men and Women: Effect of 4-Methylpyrazole", Alcohol. Clin. Exp. Res., 26:239-245.
Shah, P. P. et al., "Lamin B1 depletion in senescent cells triggers large-scale changes in gene expression and the chromatin landscape", 2013, Genes Dev., 27:1787-1799.
Stanford, S. C., 2007, "The Open Field Test: reinventing the wheel", J. Psychopharmacol., 21:134-135.
Starkman et al., 2011, "Epigenetics-Beyond the Genome in Alcoholism", Alcohol Research: Current Reviews, 34:293-305.
Stergiopoulos et al., 2016, "Nuclear receptor NR5A2 controls neural stem cell fate decisions during development", Nat. Commun., 7:1-16.
Takahashi, H. et al., 2006, "Nucleocytosolic Acetyl-Coenzyme A Synthetase Is Required for Histone Acetylation and Global Transcription", Mol. Cell, 23:207-217.
Veazey et al., 2015, "Dose-dependent alcohol-induced alterations in chromatin structure persist beyond the window of exposure and correlate with fetal alcohol syndrome birth defects", Epigenetics Chromatin, 2015, 8:39.
Vecsey, C. G. et al., 2007, "Histone Deacetylase Inhibitors Enhance Memory and Synaptic Plasticity via CREB: CBP-Dependent Transcriptional Activation", J. Neurosci., 27:6128-6140.
Walker, D. M. et al., 2015, "Regulation of chromatin states by drugs of abuse", Curr. Opin. Neurobiol., 30:112-121.
Wellen, K. E. et al., 2009, "ATP-citrate lyase links cellular metabolism to histone acetylation", Science, 324:1076-1080.
Wood, M. A. et al., 2005, "Transgenic mice expressing a truncated form of CREB-binding protein (CBP) exhibit deficits in hippocampal synaptic plasticity and memory storage", Learn. Mem., 12:111-119.
Yehuda et al 2015, "Post-traumatic stress disorder", Nat. Rev. Dis. Prim., 15057 doi:10.1038/nrdp.2015.57.
Zakhari, 2013, "Alcohol Metabolism and Epigenetics Changes", Alcohol Res., 35:6-16.
Zannas et al., 2015, "Epigenetics of Posttraumatic Stress Disorder: Current Evidence, Challenges, and Future Directions", Biol. Psychiatry, 78:1-9.
Zimatkin et al., 2006, "Enzymatic Mechanisms of Ethanol Oxidation in the Brain", Alcohol. Clin. Exp. Res., 30:1500-1505.
Zovkic, I. B. et al., 2013, "Epigenetic regulation of memory formation and maintenance", Learn. Mem., 20:61-74.

* cited by examiner

Figure 10A
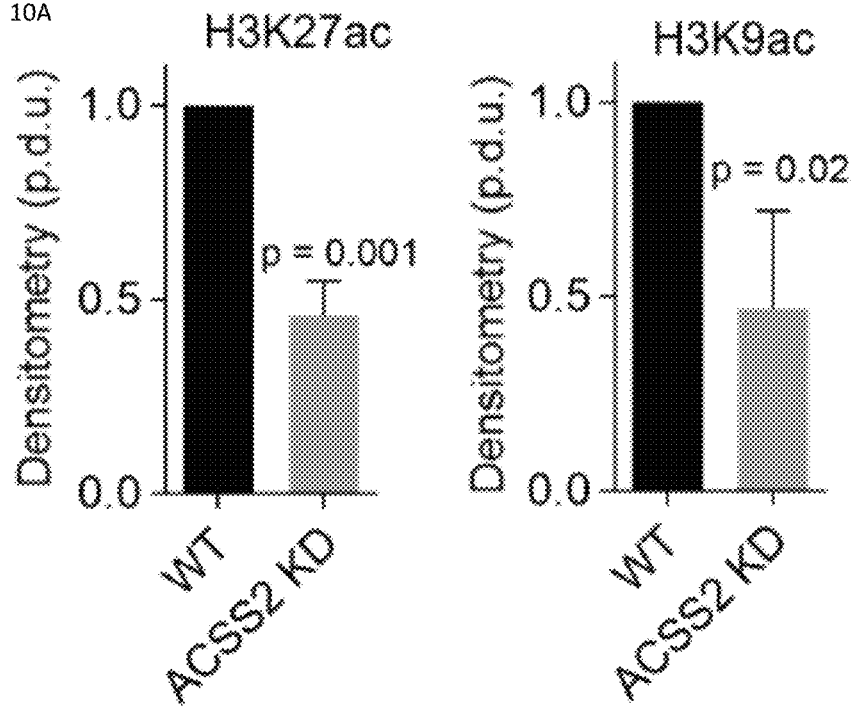
Figure 10B
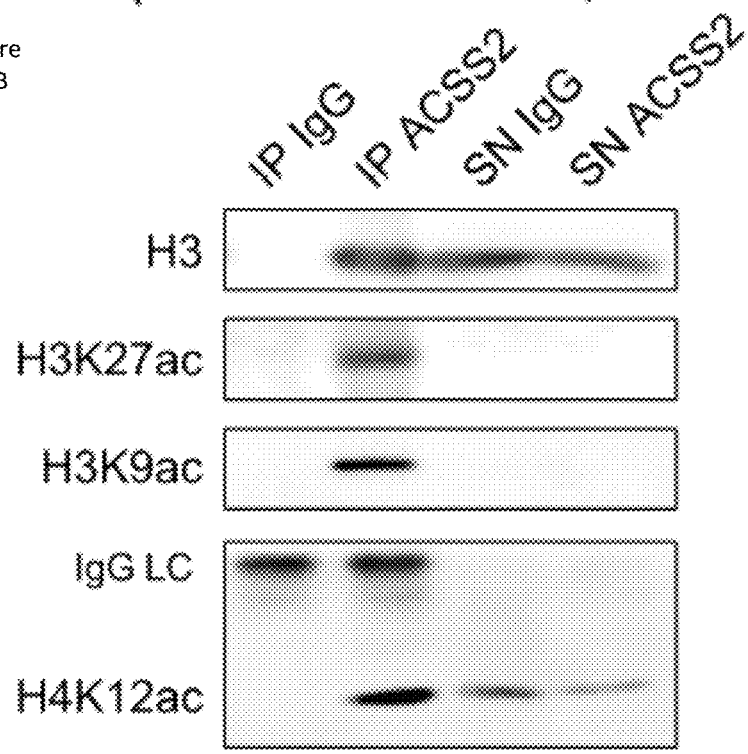
Figure 10

Figure 11A
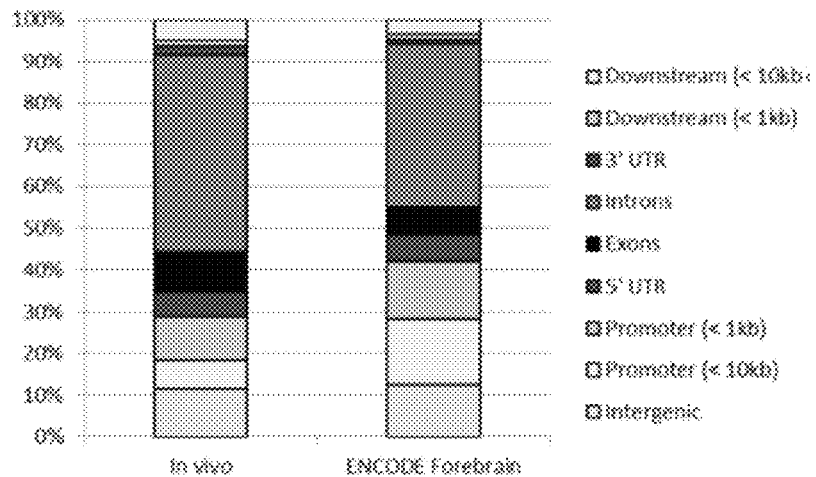
Figure 11B
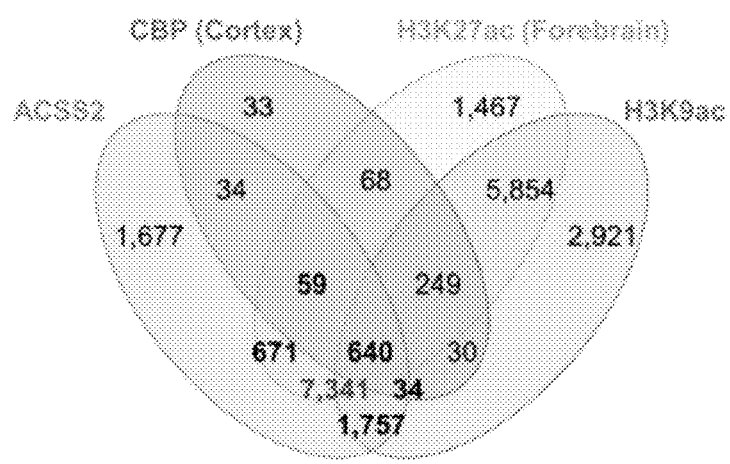
Figure 11C
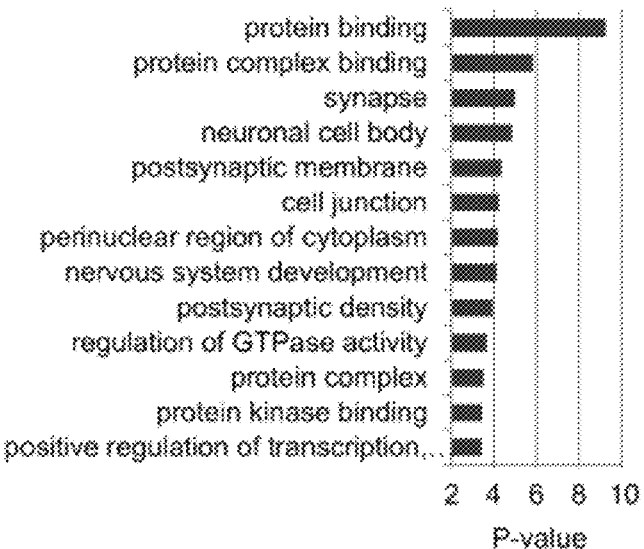
Figure 11

Figure 12A
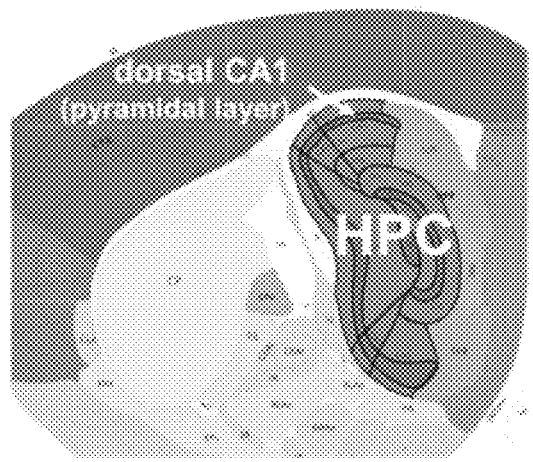
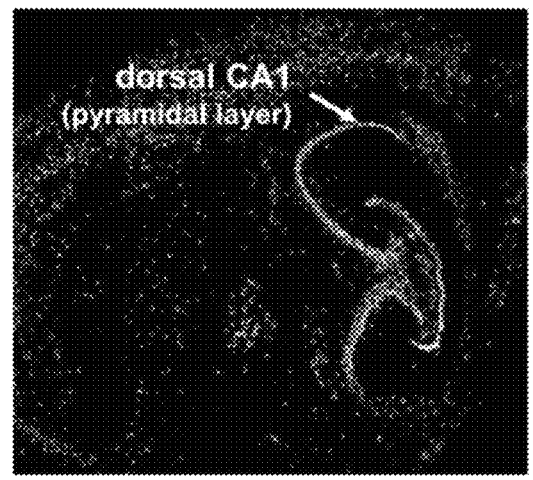
Figure 12B
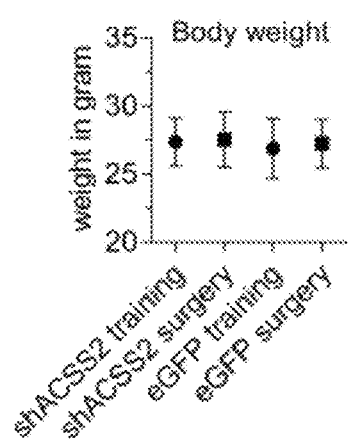
Figure 12C
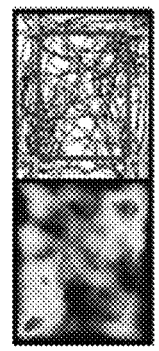
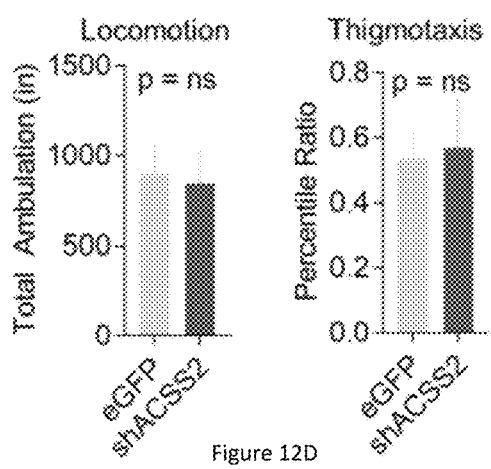
Figure 12D
Figure 12

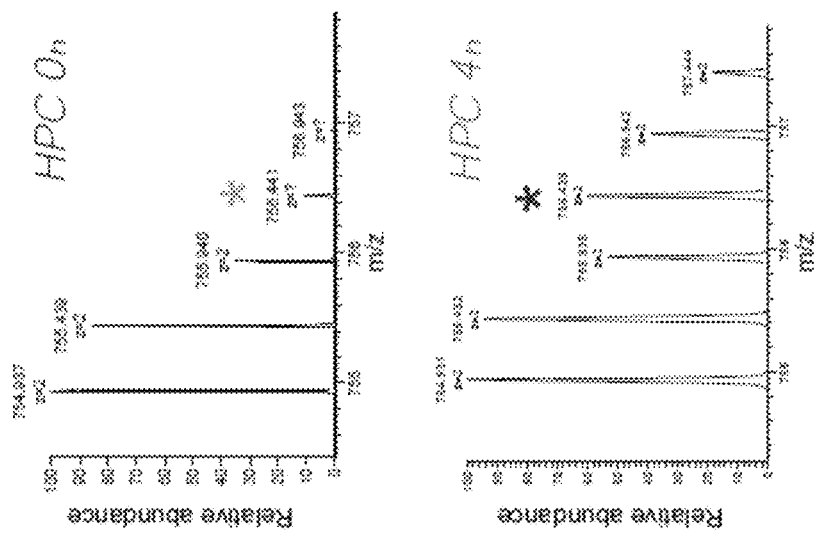
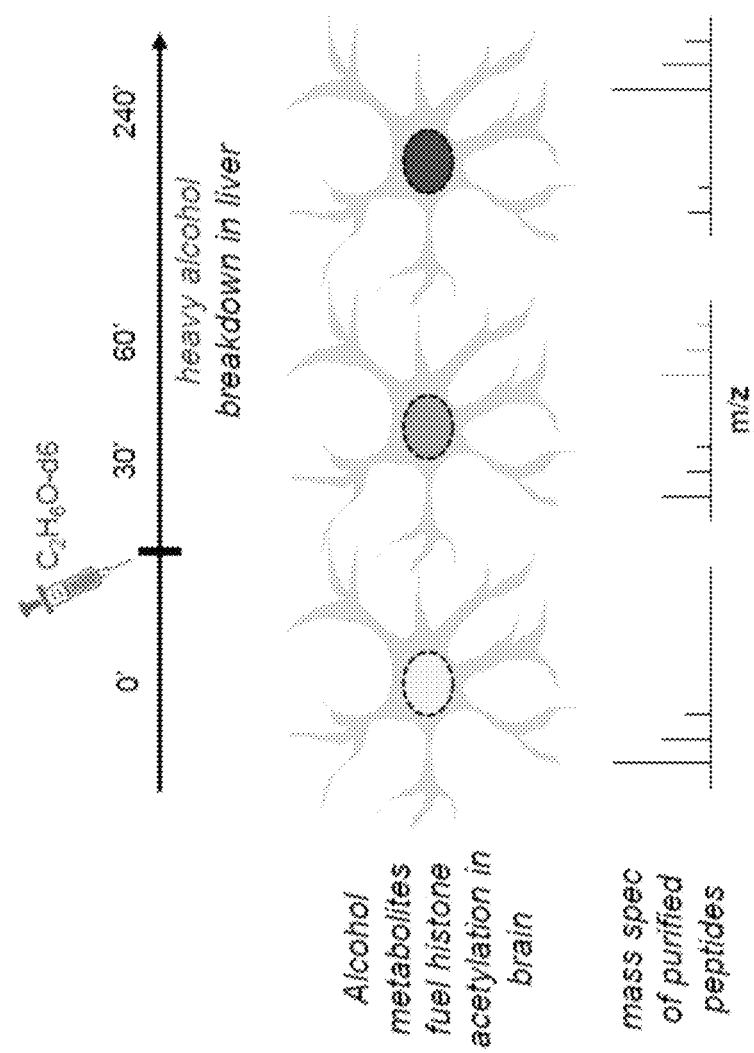
Figure 21A
Figure 21

Figure 21B
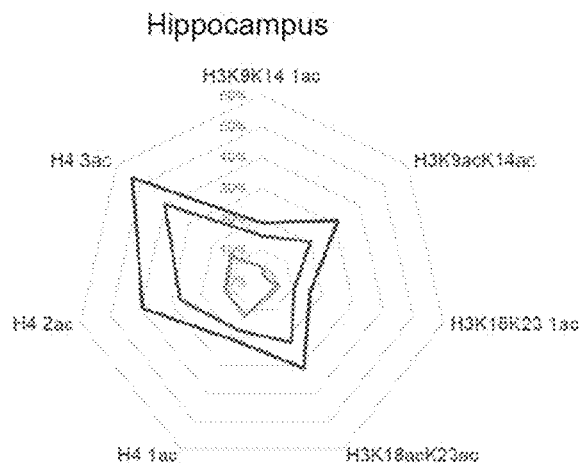
Figure 21C
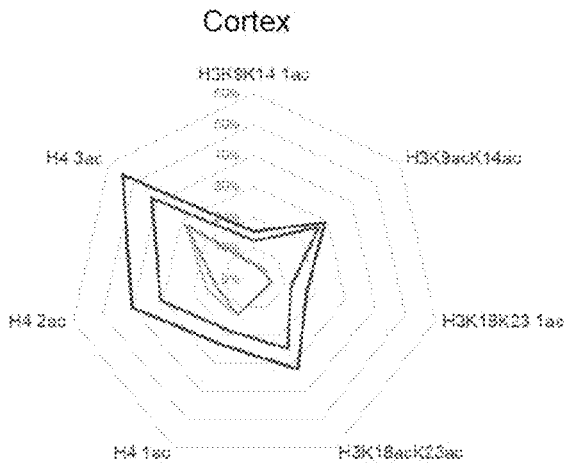
Figure 21D
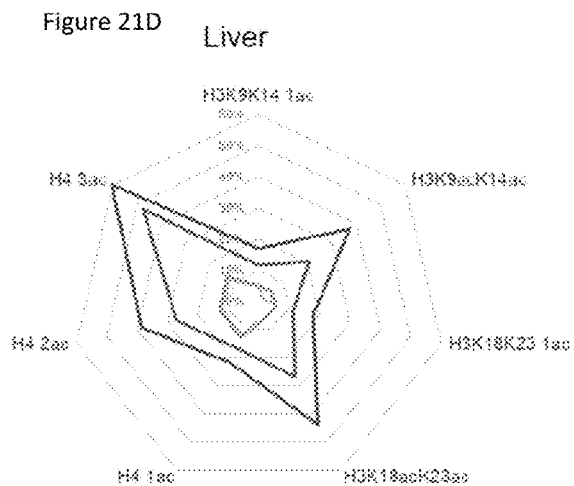
Figure 21E
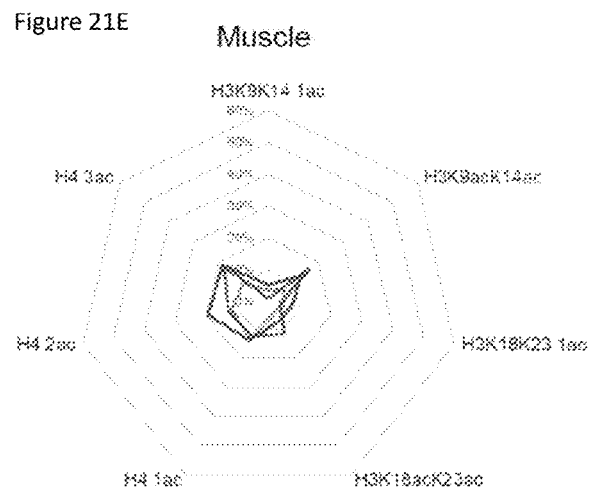
Figure 21 (continued)

Figure 22A
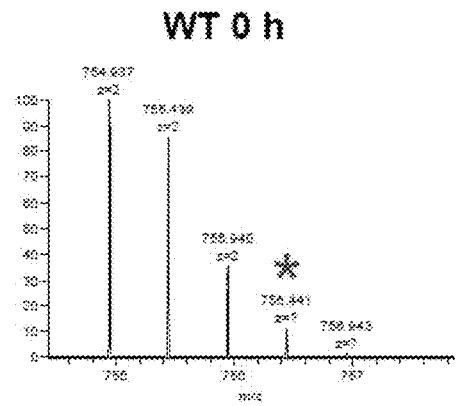
Figure 22B
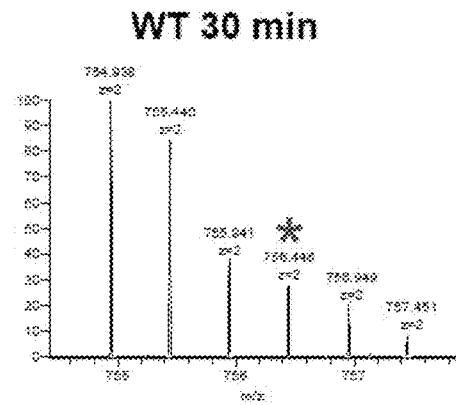
Figure 22C
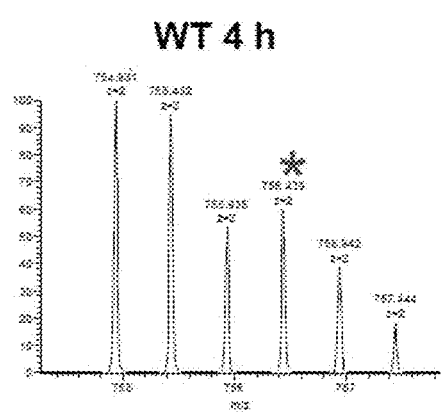
Figure 22D
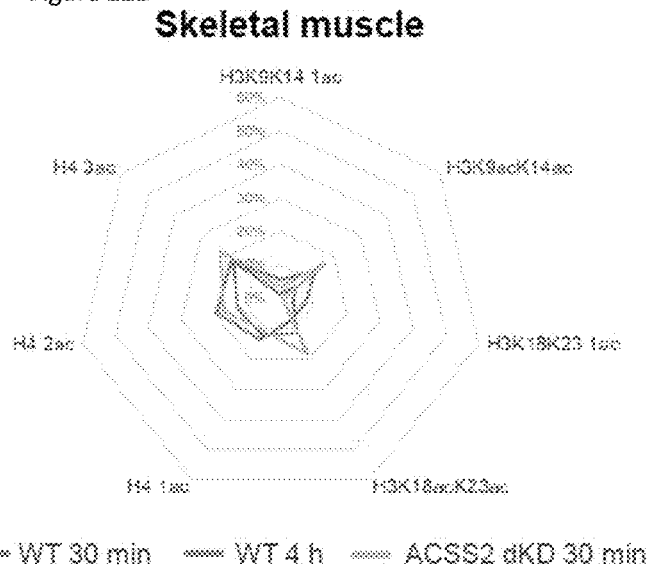
Figure 22

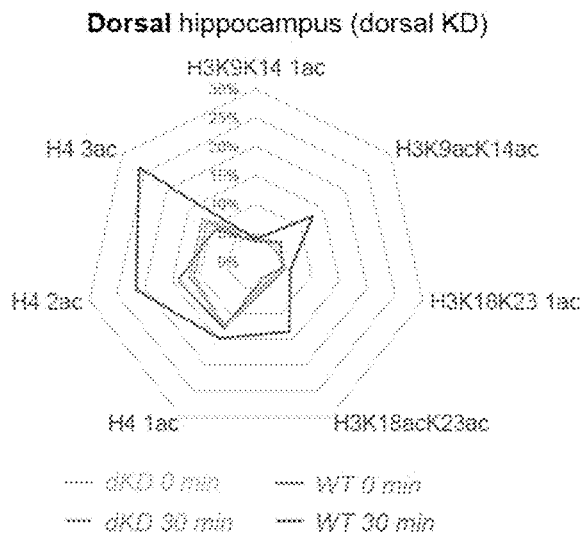
Figure 23A
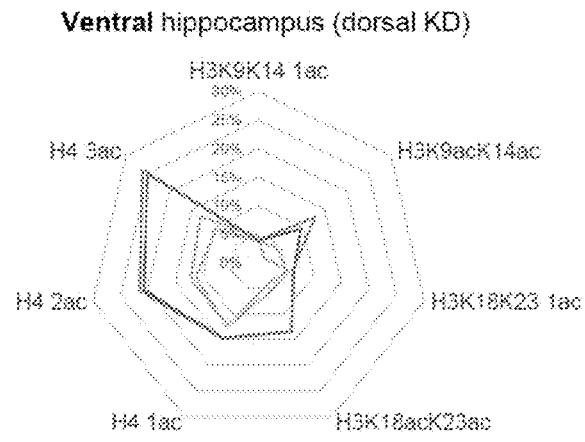
Figure 23B
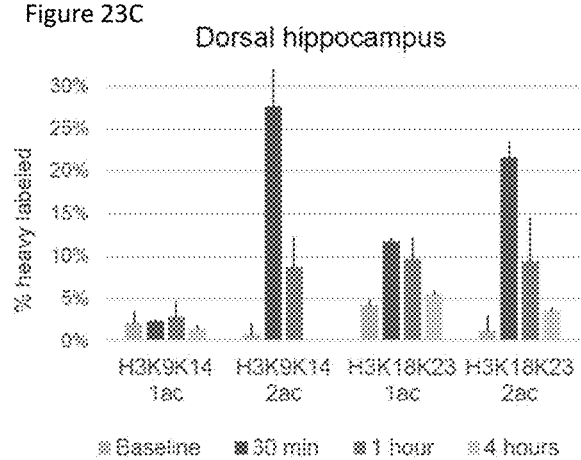
Figure 23C
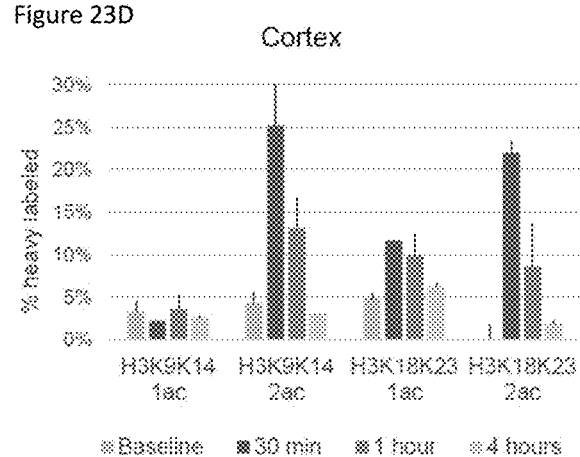
Figure 23D
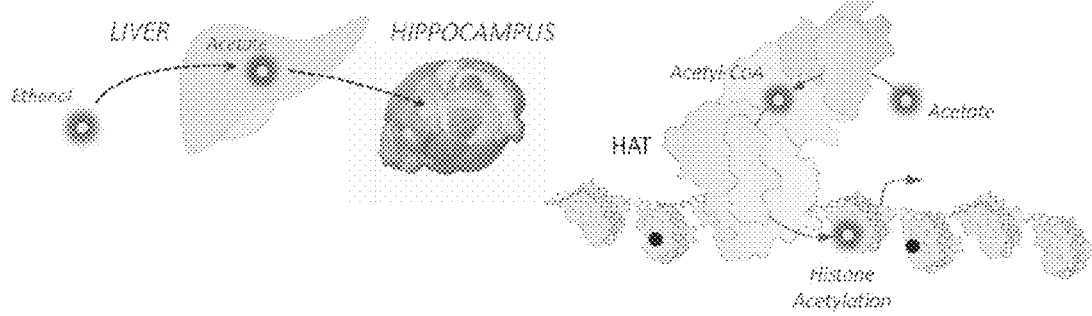
Figure 23E
Figure 23

Figure 24A
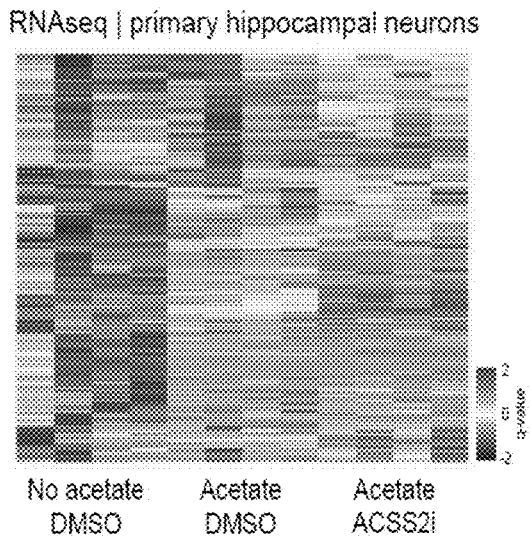
Figure 24C
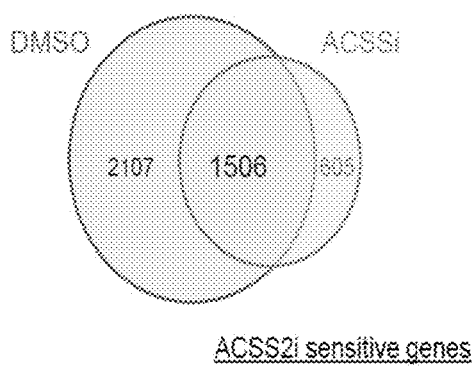
Figure 24B
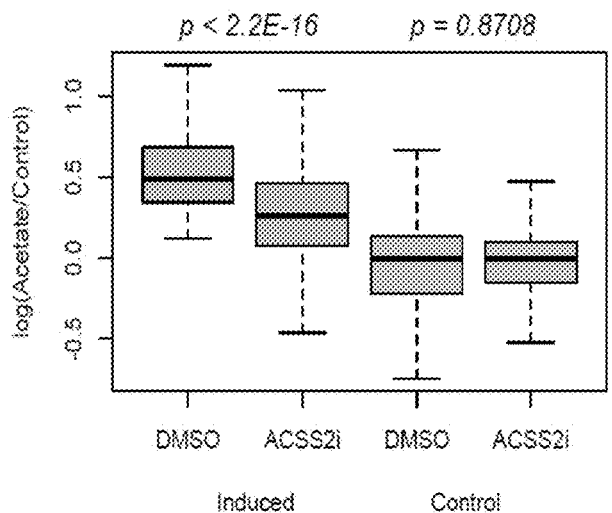
Figure 24D
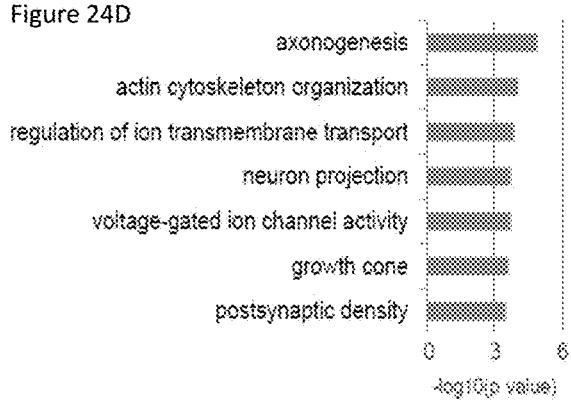
Figure 24E
| de novo Motif | P-value | Best Match |
|---|---|---|
| GAC C CTCT | 1E-18 | E2F3 |
| CACAG CAG | 1E-13 | Smad3 |
| TCC T CAA | 1E-13 | Arnt::Ahr |
| T TA TCC A | 1E-12 | RUNX2 |
| TC C AT | 1E-12 | SREBF |
| TCCTT A T | 1E-09 | Nr5a2 |
Figure 24

Figure 25A
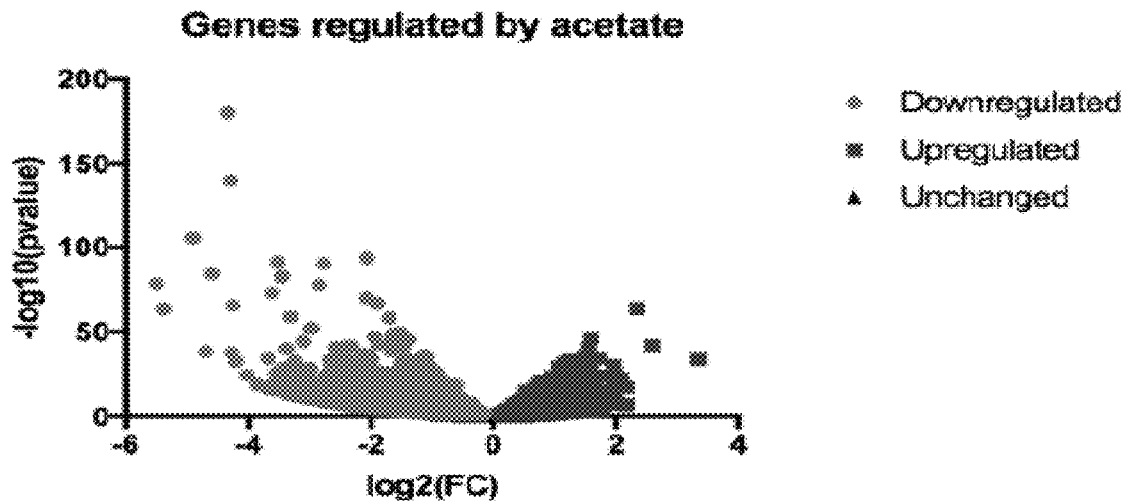
Figure 25B
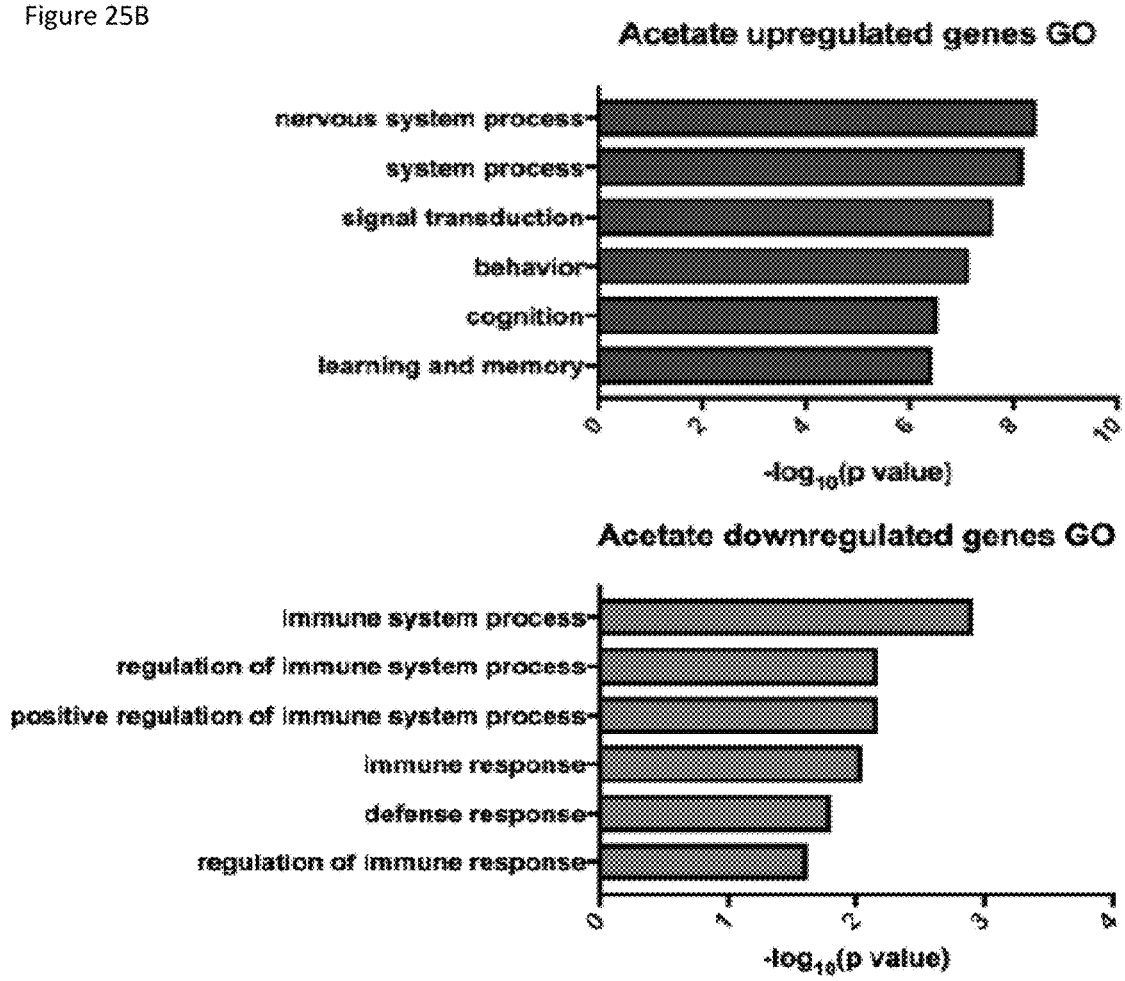
Figure 25

Figure 25C
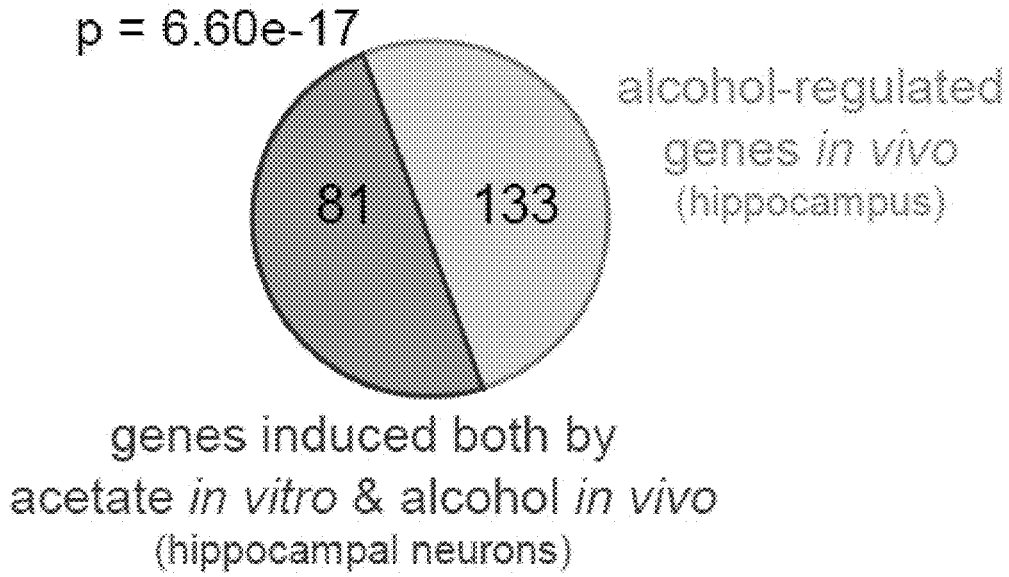
Figure 25D
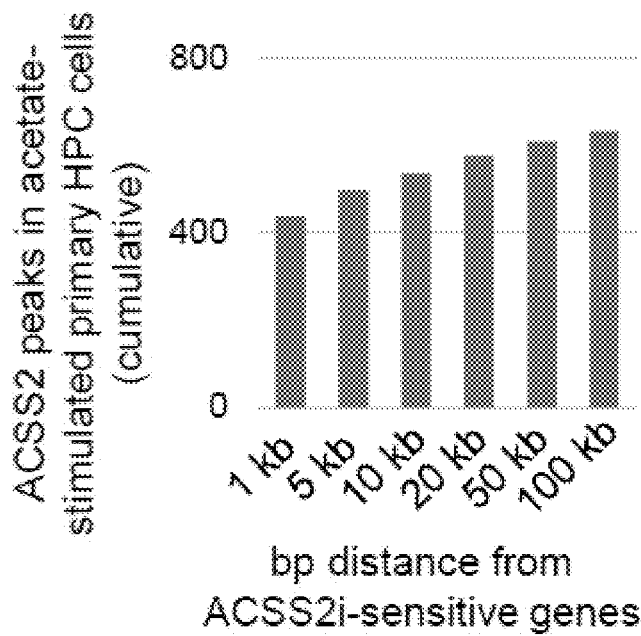
Figure 25 (continued)

Figure 26A
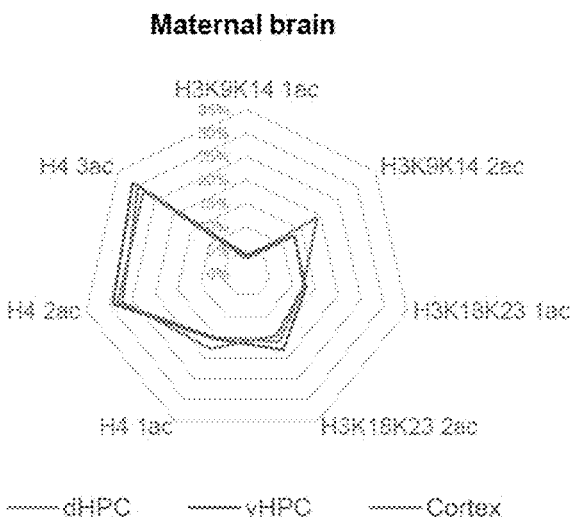
Figure 26B
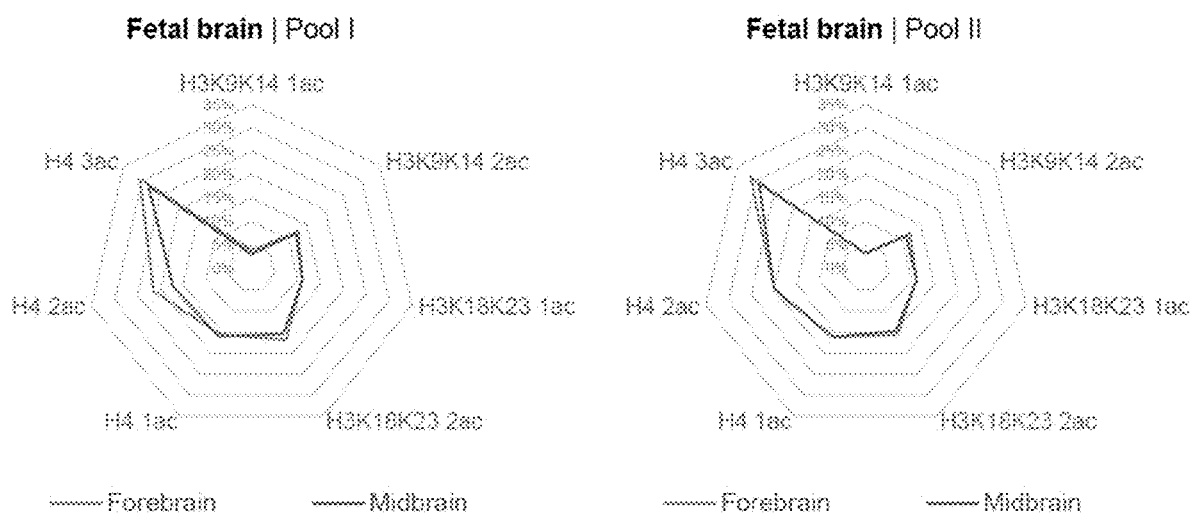
Figure 26

COMPOSITIONS AND METHODS FOR INHIBITING ACSS2

CROSS-REFERENCE TO RELATED APPLICATIONS

This application is a U.S. national phase application filed under 35 U.S.C. § 371 claiming benefit to International Patent Application No. PCT/US2018/052839, filed Sep. 26, 2018, which is entitled to priority under 35 U.S.C. § 119(e) to U.S. Provisional Patent Application No. 62/563,148, filed Sep. 26, 2017, each of which applications is hereby incorporated herein by reference in its entirety.

STATEMENT REGARDING FEDERALLY SPONSORED RESEARCH OR DEVELOPMENT

This invention was made with government support under AG031862 awarded by the National Institutes for Health. The government has certain rights in the invention.

STATEMENT OF GOVERNMENT SUPPORT

This invention was made with government support under grant numbers AG031862, AA027202 awarded by the National Institutes of Health. The government has certain rights in the invention.

BACKGROUND OF THE INVENTION

Memory formation involves synaptic restructuring and requires the coordinated expression of neuronal genes through poorly understood processes that modify chromatin (Kandel, E. R. et al., 2014, Cell, 157:163-186; Zovkic, I. B. et al., 2013, Learn. Mem., 20:61-74). Histone acetylation is a key regulator of memory storage and restructures chromatin in distinct brain regions that have been implicated in learning and memory, most prominently in the hippocampus (Graff, J. et al., 2013, Nat. Rev. Neurosci., 14:97-111). Hippocampal memory consolidation requires the transcription factor CREB and the coactivator CREB binding protein (CBP), specifically the histone acetyltransferase (HAT) activity of CBP (Wood, M. A. et al., 2005, Learn. Mem., 12:111-119; Korzus, E. et al., 2004, Neuron, 42:961-972). Furthermore, inhibitors of histone deacetylases enhance memory consolidation (Graff, J. et al., 2013, Nat. Rev. Neurosci., 14:97-111). However, the mechanisms that regulate neuronal histone acetylation in long-term memory remain incompletely understood.

Direct sensing of intermediary metabolites by chromatin-modifying enzymes such as acetyltransferases can dynamically adapt chromatin structure and gene expression (Kaelin, W. G. Jr. et al., 2013, Cell, 153:56-69; Katada, S., et al., 2012, Cell, 148:24-28). Alteration of pools of intracellular acetyl-CoA manipulates histone acetylation (Cai, L., et al., 2011, Mol. Cell, 42:426-437; Wellen, K. E. et al., 2009, Science, 324:1076-1080); thus, metabolic enzymes that generate nuclear acetyl-CoA might directly control histone acetylation and gene expression (Gut, P. et al., 2013, Nature, 502:489-498; Pietrocola, F. et al., 2015, Cell Metab., 21:805-821). In mammalian cells, there are two principal enzymes that generate acetyl-CoA for histone acetylation: acetate-dependent acetyl-CoA synthetase 2 (ACSS2) and citrate-dependent ATP-citrate lyase (ACL) (Pietrocola, F. et al., 2015, Cell Metab., 21:805-821). The relative importance of ACSS2 and ACL for nuclear histone acetylation differs by tissue type, developmental state, and disease (Wellen, K. E. et al., 2009, Science, 324:1076-1080; Pietrocola, F. et al., 2015, Cell Metab., 21:805-821), but the roles of these enzymes in post-mitotic neuronal cells are unknown.

Thus, there remains a need in the art for therapies to treat neurological and cognitive diseases and disorders. The present invention addresses this unmet need.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1A through FIG. 1G, depicts results from example experiments demonstrating nuclear ACSS2 supports neuronal gene expression. (FIG. 1A) ACSS2 localizes to the cytoplasm in undifferentiated CAD neurons. ACSS2 was imaged by immunofluorescence microscopy in CAD cells (4',6-diamidino-2-phenylindole (DAPI) and α-tubulin (α-Tub) immunostaining show nuclei and cytoplasm, respectively). (FIG. 1B) ACSS2 localizes to the nucleus in differentiated CAD neurons. (FIG. 1C) Western blot analysis of cytoplasmic (CE) and nuclear (NE) extracts from undifferentiated CAD cells (undiff.) and differentiated CAD neurons (diff.) for ACSS2, ACL and histone H3. Nuclear ACSS2 expression is higher in differentiated cells (p.d.u., procedure defined unit; t-test P=0.002, n=3, mean±s.d.). (FIG. 1D) ACSS2 knockdown reduces differentiation-linked upregulation of neuronal gene expression program. Scatter plot contrasts the fold-change fragments per kilobase of transcript per million mapped (FPKM) of induced genes (FIG. 6C) between wild-type (WT) and ACSS2 knockdown (KD) cells. Marginal distributions show histogram and kernel density estimation. Ordinary least squares linear regression is displayed with 95% confidence interval. (FIG. 1E) Western blot of lysates from differentiated CAD neurons that were infected with lentiviral control (WT) or ACSS2 knockdown vector (shACSS2) (quantification shown in FIG. 5G; n=3). (FIG. 1F) ACSS2 knockdown greatly reduces gene upregulation. Quintiles of upregulated genes (red dots in FIG. 6C) with the greatest fold-change increase in wild-type cells (grey). Corresponding gene quintiles depict fold-change FPKM in ACSS2 knockdown cells (green) (for each quintile, columns represent the mean induction value of genes; mean±s.e.m.). (FIG. 1G) ACSS2i treatment of differentiated CAD neurons results in reduced expression of differentiation-induced genes. All genes are plotted in order of fold-change in wild-type CAD differentiation, and z-scores were computed for ACSS2i treatment and control, representing upregulation as blue and downregulation as red (RNA-seq in 24-hour ACSS2i treated and DMSO-treated control neurons, genes removed with z-score <0.5). Scale bar, 10 m (FIG. 1A, FIG. 1B).

FIG. 2A through FIG. 2J, depicts results from example experiments demonstrating that ACSS2 is recruited to transcriptionally active chromatin and promotes neuronal histone acetylation. (FIG. 2A) Genome browser tracks showing ChIP-seq over the Camk2a locus show that increases in H4K5, H4K12, and H3K9 acetylation co-occur with proximate ACSS2 enrichment upon CAD neuron differentiation (chromosome 18: 60,920,000-60,990,000). (FIG. 2B) Gene ontology term enrichment analysis of top 5% genes that become ACSS2-bound during CAD neuron differentiation show neuronal pathways. (FIG. 2C) Violin-contour plots show that ChIP-seq enrichment of the indicated histone acetylation occurs with top-ranked ACSS2 enrichment during neuronal differentiation of CAD cells. (FIG. 2D) ChIP-seq enrichment of the 299 genes that are reduced upon ACSS2i treatment (see Example 1 Methods) shows high correlation ($P<2.2\times10^{-16}$ for all) with histone acetylation in the differentiated state (AUC, area under the curve; d, differentiated; u, undifferentiated). (FIG. 2E) Analysis of all genes previously linked to neuronal differentiation (ND genes, AmiGO annotation set of 1,315 genes), and the subset of known ND genes that are induced during differentiation of CAD cells (Induced), shows reduced expression in ACSS2i-treated CAD neurons (inh.) compared to DMSO-treated control neurons (con.). Inhibitor-treated versus control, $P<2.2\times10^{-16}$. (FIG. 2F) Nuclear acetyl-CoA levels are reduced in response to either knockdown of ACSS2 (shACSS2; mean $\Delta=-0.19\pm0.03$,  $P=0.003$) or application of the ACSS2 inhibitor (mean $\Delta=-0.25\pm0.05$,  $P=0.006$; n=3, mean+s.d.). (FIG. 2G) Western blot analysis of whole-cell lysates shows that lentiviral shRNA-mediated knockdown of ACSS2 lowers H3K9 and H3K27 acetylation (quantified in FIG. 10A). (FIG. 2H) Western blot analysis of immunoprecipitation eluates shows that CBP is co-immunoprecipitated with ACSS2 but not with control Ig. (FIG. 2I) Immunofluorescence in primary hippocampal neurons shows nuclear localization of ACSS2 (day 7 of in vitro differentiation culture, isolated from C57BL/6 embryos). Scale bar, 50 μm. (FIG. 2J) Western blots of lysates from primary hippocampal neurons (d7) treated for 24 hours with ACSS2i and probed with the indicated antibodies (quantified in FIG. 10C) show reduction of histone acetylation.

FIG. 3A through FIG. 3F, depicts results from example experiments demonstrating that ACSS2 ChIP-seq localization is linked to histone acetylation in vivo in mouse hippocampus. (FIG. 3A) ChIP-seq for ACSS2 and H3K9ac in mouse hippocampus. Track views show ACSS2 and H3K9ac for three neuronal genes involved in memory: Arc, Egr2 and Nr2f2 (chr15:74,496,025-74,506,488; chr10:66,991,018-67,006,804; and chr7: 77,488,549-77,516,626, respectively). (FIG. 3B) In vivo hippocampal ACSS2 and H3K9ac peaks co-localize with the nearest gene TSS (<1 kb from peak) among all RefSeq transcripts. (FIG. 3C) RNA-seq expression in dorsal hippocampus (dHPC) correlates with hippocampal ACSS2 binding and enrichment of H3K9 acetylation. (FIG. 3D) Expression profile of genes classified by their ACSS2 and H3K9ac enrichment state. (FIG. 3E) Overlap between ACSS2 targeted genes (hippocampus) and CBP and H3K27ac enrichment for entire set of peaks (ENCODE CBP and H3K27ac ChIP-seq in mouse forebrain and cortex). (FIG. 3F) Motif analysis at ACSS2 peaks from in vivo ChIP-seq in hippocampus showing top enrichment of NRF1, a neuronal transcription factor.

FIG. 4A through FIG. 4F, depicts results from example experiments demonstrating that ACSS2 knockdown in dorsal hippocampus impairs object location memory and upregulation of immediate early genes following training. (FIG. 4A) Stereotactic surgery was performed to deliver AAV9 knockdown vector into the dorsal hippocampus (AP, −2.0 mm; DV, −1.4 mm; ML, +1.5 mm from bregma); 4 weeks later, habituated mice were trained in object location memory (OLM; four 5-min training sessions in arena with three different objects). Twenty-four hours later the mice were given a retention test in which one object was moved to a novel location (n=10 per cohort). (FIG. 4B) Western blot analysis of hippocampal tissue removed from mice injected into the dorsal (d) or ventral (v) hippocampus with either eGFP control or ACSS2 knockdown vector shows specific reduction of ACSS2 in dorsal hippocampus. (FIG. 4C) ACSS2-knockdown mice are impaired in object location memory. eGFP control and shACSS2 AAV9 mice display no preference for any of three objects (O1-3) during the object location memory training session (TR). In the retention test 24 hours later, control mice show a preference for the novel object location (NL), whereas the knockdown mice display no such preference. *** $P<0.001$; n=10, mean±s.d. (FIG. 4D) The spatial memory defect in ACSS2-knockdown mice manifests in a lowered discrimination index (% DI=(t NL−t FL)/(t NL+t FL)) compared to control mice ($\Delta$ DI=−29.5±11.4, * $P=0.02$; n=10, mean±s.d.). (FIG. 4E) Training-induced expression of a cohort of immediate early genes (FIG. 12H) is greatly attenuated in ACSS2-knockdown mice (n=4 mice per group, 2 replicates for each condition, $P<0.0001$, paired t-test, mean±s.d.). (FIG. 4F) Model for function of ACSS2 as a chromatin-bound coactivator to provide acetyl-CoA locally to promote histone acetylation and activity-induced upregulation of immediate early genes.

FIG. 5A through FIG. 5G, depicts results from example experiments demonstrating that ACSS2 localizes to the nucleus of neurons. (FIG. 5A) Percentage of cells with nuclear staining in ACSS2 immunofluorescence experiments (undiff., undifferentiated CAD cells; diff., differentiated CAD neurons; hippocampal, primary hippocampal neurons day 7; a minimum of 50 cells were examined in three replicate immunofluorescence experiments; t-test undiff. vs diff. $P<0.0001$, undiff. vs hippocampal $P<0.0001$; error bars, s.e.m.). (FIG. 5B) Western blots of cytoplasmic (CE) and nuclear (NE) extracts from undifferentiated CAD cells and differentiated CAD neurons were probed with the indicated antibodies. (FIG. 5C, FIG. 5D) Immunofluorescence in primary cortical neurons isolated from C57BL/6 embryos, at day 7 (FIG. 5C) and day 14 (FIG. 5D) of in vitro differentiation culture. ACSS2 locates predominantly to nuclei in differentiated primary cortical neurons. All scale bars, 25 μm. (FIG. 5E) Immunofluorescence in primary hippocampal neurons isolated from C57BL/6 embryos at day 14 of in vitro differentiation culture. ACSS2 locates predominantly to nuclei in differentiated primary neurons. (FIG. 5F) Immunofluorescence in primary hippocampal neurons at day 7 shows that ACL is chiefly localized to the cytoplasm. (FIG. 5G) Neuronal differentiation markers decrease in ACSS2 knockdown cells. CAD cells were infected with lentiviral control (WT) or knockdown vector (shACSS2). Western blots of lysates from stably infected differentiated cells were probed with the indicated antibodies and quantified using ImageJ (n=3; error bars, s.e.m.).

FIG. 6A through FIG. 6O, depicts results from example experiments demonstrating that ACSS2 regulates neuronal gene expression. (FIG. 6A, FIG. 6B) Correlation plots of replicate RNA-seq in undifferentiated CAD cells (FIG. 6A) and differentiated CAD neurons (FIG. 6B) for scramble control. (FIG. 6C) Transcriptome analysis via RNA-seq, done in two highly correlated biological replicates, identified 894 genes that became upregulated in differentiated CAD neurons (red dots depict genes with >1.6-fold increase). (FIG. 6D) Pathway analysis of the 894 upregulated genes (red dots in FIG. 2A) using StringDB. The protein-protein interaction graph depicts a network of binding partners that centers on key players in activity-dependent signaling and synaptic plasticity: Itpr1, Grin1, Nefh, Dynclh1 and Calm1. (FIG. 2E) Gene ontology enrichment analysis shows upregulation of neuronal pathways. Gene ontology analysis was used on the 894 genes that become upregulated in differentiated CAD neurons (FIG. 6C; identified by RNA-seq, fold-enrichment (FE)>3.5, FDR<0.005). (FIG. 6F) Genome browser view of Nudt from RNA-seq and ChIP-seq (H4K12ac, H4K5ac, and H3K9ac: mm10 chr5: 140,327,500-140,339,000). (FIG. 6G) Relative gene enrichment of H3K9ac, H4K5ac, and H4K12ac at genes that are upregulated during CAD neuron differentiation (>1.6-fold, grey bars) versus all other genes (black bars). (FIG. 6H, FIG. 6I) Correlation plots of replicate RNA-seq in undifferentiated CAD cells for ACL knockdown (FIG. 6H), and ACSS2 knockdown (FIG. 6I). (FIG. 6J, FIG. 6K) Correlation plots of replicate RNA-seq in differentiated CAD neurons for ACL knockdown (FIG. 6J) and ACSS2 knockdown (FIG. 6K). (FIG. 6L) ACL knockdown has a much smaller effect on differentiation-linked upregulation of neuronal gene expression (compare to FIG. 1D). Scatter plot contrasts the fold-change FPKM of induced genes (FIG. 6C) between wild-type and ACL knockdown cells. Marginal distributions show histogram and kernel density estimation. Ordinary least squares linear regression is displayed with 95% confidence interval. (FIG. 6M) The corresponding quintiles of upregulated genes (red dots in FIG. 6C) with the greatest fold-change FPKM increase in wild-type cells. The ACL knockdown showed the same upward trend as the wild-type cells (red bars, compared to black bars in FIG. 1F), contrasting with the severe defect in ACSS2-knockdown cells (green bars; for each quintile, columns represent the mean induction value of genes and error bars represent s.e.m.). (FIG. 6N) Box plot of global mRNA transcript levels in undifferentiated and differentiated CAD neurons from RNA-seq in wild-type (scramble control knockdown; grey), ACSS2-knockdown (shACSS2 #25 knockdown; green), and ACL-knockdown (shACL #17 knockdown; red) cells. Genome-wide transcript levels are reduced in differentiated ACL-knockdown cells when compared to differentiated wild-type cells (error bars, s.e.m.), whereas the global reduction in differentiated ACSS2-knockdown cells is less significant when compared to differentiated wild-type cells (error bars, s.d.). (FIG. 6O) Genes sensitive to ACSS2 knockdown (top 20%) are also sensitive to ACSS2i treatment, which lowers their expression compared to all genes.

FIG. 7A through FIG. 7P, depicts results from example experiments demonstrating that ACSS2 is chromatin-bound in differentiated CAD neurons. (FIG. 7A) ChIP-seq in differentiated CAD neurons was performed in replicate with two different antibodies against ACSS2. Correlation plot displays relative enrichment over corresponding MACS peaks (default parameters with input as control, 1,598 peaks). (FIG. 7B) Correlation plot displays relative genome-wide ChIP-seq enrichment. (FIG. 7C) UCSC Genome Browser views of ChIP-seq tracks show that, upon CAD neuron differentiation, increases in H4K5, H4K12, and H3K9 acetylation over the Nudt1 locus co-occur with ACSS2 enrichment (chr5: 140,326,845-140,339, 655). (FIG. 7D) UCSC Genome Browser view of indicated ChIP-seq tracks in undifferentiated CAD cells and differentiated CAD neurons over Tab2 locus (chr10: 7,875,000-8, 004,000). (FIG. 7E) Gene ontology enrichment analysis of the genes most proximate to ACSS2 peaks demonstrates that neuron-specific genes are enriched. (FIG. 7F) Frequency of ACSS2 peaks (T antibody) located upstream of their target gene associated with histone acetylation. (FIG. 7G) Frequency of ACSS2 peaks (CS antibody) located upstream of their target gene associated with histone acetylation. (FIG. 7H) Table shows percent direct overlap of ACSS2 peaks with H3K9ac, H4K5ac, and H4K12ac broad MACS peaks. (FIG. 7I, FIG. 7J, FIG. 7K) Decile plots depict enrichment of H3K9ac (FIG. 7I), H4K5ac (FIG. 7J), and H4K12ac (FIG. 7K) over ranked deciles of ACSS2 peak enrichment (zeroes removed). (FIG. 7L, FIG. 7M, FIG. 7N) Differentiation-induced co-enrichment of ACSS2 and acetyl broad peaks (MACS). Peak enrichment correlation indicated for H3K9ac (FIG. 7L), H4K5ac (FIG. 7M), and H4K12ac (FIG. 7N). (FIG. 7O) Discovered de novo motifs for transcription factor binding sites predicted by HOMER from all ACSS2 ChIP-seq peaks called by MACS in differentiated CAD neurons. (FIG. 7P) ChIP-seq enrichment of differentiation-induced genes as a group shows correlation with histone acetylation in differentiated CAD neurons.

FIG. 8A and FIG. 8B, depicts results from example experiments demonstrating that ACSS2 enrichment co-occurs with histone acetylation at neuronal genes in differentiating CAD neurons. (FIG. 8A) UCSC Genome Browser views of ChIP-seq tracks demonstrate that increases in H4K5, H4K12, and H3K9 acetylation co-occur with ACSS2 enrichment over the Idua (α-1-iduronidase) locus upon CAD neuron differentiation (chr5: 108,649,457-108,687,261). (FIG. 8B) At the Slc19A1 (solute carrier family 19 member 1) gene, elevated histone H4K5, H4K12, and H3K9 acetylation levels correspond with increasing ACSS2 enrichment in differentiated CAD neurons (chr10: 76,761,141-77,170,455).

FIG. 9A through FIG. 9I, depicts results from example experiments demonstrating that genic ACSS2 enrichment upon CAD neuronal differentiation corresponds to increased histone acetylation. (FIG. 9A, FIG. 9B, FIG. 9C, FIG. 9D) Metagene enrichment analysis shows ChIP occupancy for ACSS2 (FIG. 9A), H3K9ac (FIG. 9B), H4K5ac (FIG. 9C) and H4K12ac (FIG. 9D) across the top 5% of genes enriched for ACSS2 in differentiated CAD neurons (Top 5% DE; red). The bottom 80% of genes (Bot 80% DE) is shown in blue, and the average signal across all genes (All genes DE) is shown in green. (FIG. 9E, FIG. 9F, FIG. 9G, FIG. 9H) Meta-gene enrichment analysis shows ChIP occupancy for ACSS2 (FIG. 9E), H3K9ac (FIG. 9F), H4K5ac (FIG. 9G) and H4K12ac (FIG. 9H) at the top 5% of genes that become dynamically bound by ACSS2 upon neuronal differentiation (Top 5% DE; red). The bottom 80% of genes (Bot 80% DE) is shown in blue, and the average signal across all genes (All genes DE) is shown in green. (FIG. 9I) Multiple linear regression analysis was implemented to model the interaction between genic ACSS2 enrichment and wild-type gene expression changes, and to visualize the interaction between differentiation-linked gene expression changes and ACSS2 recruitment to chromatin. The contour plot of this fitted regression model displays high levels of ACSS2 enrichment in red and low levels in blue, and is overlaid with the scatter plot of the independent gene expression variables. The visualized model demonstrates that high ACSS2 enrichment corresponds to increased gene expression in differentiated CAD neurons.

FIG. 10A through FIG. 10C, depicts results from example experiments demonstrating that ACSS2 functions in neuronal histone acetylation. (FIG. 10A) Western blot analysis of whole-cell lysates shows that lentiviral shRNA-mediated knockdown of ACSS2 lowers H3K9 and H3K27 acetylation (compare to FIG. 2G), quantified using ImageJ (n=3, error bars show s.e.m.). (FIG. 10B) Western blot analysis of eluates and supernatants of IgG control and ACSS2 co-immunoprecipitation experiments indicates that ACSS2 binds to acetylated chromatin. (FIG. 10C) Western blots of lysates from primary hippocampal neurons (day 7) treated for 24 hours with the ACSS2i, probed with the indicated antibodies (compare to FIG. 2J), and quantified using ImageJ (n=3, error bars show s.e.m.).

FIG. 11, comprising FIG. 11A through FIG. 11C, depicts results from example experiments demonstrating that ACSS2 chromatin association and H3K9ac in dorsal hippocampus corresponds to H3K27ac and CBP enrichment in neuronal tissue. (FIG. 11A) Genome-wide compartment analysis of in vivo hippocampal ChIP-seq of H3K9ac and mouse forebrain H3K9ac ChIP-seq from ENCODE, showing a similar peak distribution genome-wide: although they originate in different brain regions, the in vivo H3K9ac ChIP data are in strong agreement (Spearman R=0.67). (FIG. 11B) Overlap of RefSeq transcripts targeted by the indicated enzyme or modification (peaks for CBP (GSM1629373) and H3K27ac (GSM1629397) in mouse cortical neurons were called using MACS2 (narrow peaks, FDR 0.1%) with an input sonication efficiency control (GSM1629381); peaks were associated to the nearest TSS among all RefSeq transcripts). (FIG. 11C) Gene Ontology enrichment analysis performed on common CBP-ACSS2 targets, indicating that these enzymes co-target genes that modulate synapse biology and synaptic membrane potential.

FIG. 12A through FIG. 12H, depicts results from example experiments demonstrating that attenuation of ACSS2 expression in the dorsal hippocampus impairs object location memory. (FIG. 12A) ACSS2 RNA in situ hybridization on ACSS2 in sagittal section of hippocampal region CA1 (left, reference atlas adapted from Allen Mouse Brain Atlas12; right, in situ hybridization; HPC, hippocampus proper). (FIG. 12B) Weight of eGFPAAV9 control and shACSS2-AAV9 knockdown mice before intracranial surgery, and following recovery before object location memory (OLM) training (NS, n=10 per group, error bars show s.d.). (FIG. 12C, FIG. 12D) ACSS2 knockdown mice showed no defect in locomotion or thigmotaxis (tendency to remain close to vertical surfaces in an open field, a measure of anxiety), as quantified over 5 min in the open field test; (FIG. 12C) shows example heat map of tracking data (NS, n=10 per group, error bars show s.d.). (FIG. 12E) Exploration times by eGFP-AAV9 control and shACSS2-AAV9 knockdown mice recorded for the three objects (O1-3) during the first OLM training session (TR) and the 24-h retention test (NL, object in novel location; FL, objects in former location). (FIG. 12F) Compared to the control eGFPAVV9 mice, ACSS2-knockdown mice showed no defect in contextual fear memory. Freezing in chamber on day of contextual fear conditioning was recorded and quantified pre-shock (FC Training; NS, n=10 per cohort, error bars show s.d.). Fear memory was measured as the freezing response after re-exposure to the context 1 day after contextual fear conditioning (aversive stimulus: 1.5 mA electrical shock; NS, n=10 per cohort, error bars show s.d.). (FIG. 12G) RNA-seq was performed on the dorsal hippocampus of eGFP control and shACSS2-knockdown animals. Global transcript levels were not affected by ACSS2 knockdown (dHPC, dorsal hippocampus; four animals per group, two replicates for each condition; NS, paired t-test, error bars show s.d.). (FIG. 12H) Baseline expression of immediate-early genes in untrained animals was unaltered in ACSS2-knockdown mice. RNA-seq was performed on the dorsal hippocampus of eGFP control and shACSS2-knockdown mice (r=0.82, P<0.0001; HCC, homecage circadian control).

FIG. 13A through FIG. 13F, depicts results from example experiments demonstrating that ACSS2 regulates retrieval-induced upregulation of immediate-early genes in vivo. (FIG. 13A) Genome-wide RNA-seq was performed on the dorsal hippocampus of eGFP control and shACSS2-knockdown mice. The analysis was focused on the set of previously identified and validated genes that become upregulated during the sensitive period following memory retrieval. The baseline expression of immediate early genes in untrained animals was not changed in shACSS2-AAV9 mice when compared to eGFP-AAV9 control mice (CC, circadian control). (FIG. 13B) During the sensitive period following contextual memory retrieval (RT, 30 min post-exposure to conditioning chamber 24 hours after fear conditioning), immediate early genes were upregulated in the dorsal hippocampus of control injected mice. By contrast, the dynamic retrieval-induced expression of these early response genes is absent in ACSS2-knockdown mice (P=0.001, paired t-test). (FIG. 13C) Induction defect of immediate early genes in shACSS2-AAV9 injected animals (RT/CC). (FIG. 13D) The baseline expression of genes that were downregulated after contextual memory retrieval is not altered in ACSS2-knockdown mice. (FIG. 13E) Downregulation of retrieval-responsive genes occurs in both eGFP control and ACSS2-knockdown mice, except for Cldn5. (FIG. 13F) Retrieval-induced downregulation of retrieval-responsive genes in the dorsal hippocampus in eGFP control versus shACSS2-knockdown mice (RT/CC).

FIG. 21, comprising FIG. 21A through FIG. 21E, depicts that alcohol metabolites feed histone acetylation in the brain. FIG. 21A depicts an experimental outline of in vivo EtOH-$d_6$ mass spectrometry. FIG. 21B depicts experimental results demonstrating metabolized heavy EtOH-$d_6$ is incorporated into histone acetylation in hippocampus. The Arachne plot axis represents the % of the third isotope for the acetylated peptide, corresponding to the $D_3$ labeled form; the natural relative abundance of that isotope is apparent in the 'none' and 'saline 1 h' treatment groups. FIG. 21C depicts experimental results demonstrating label incorporation into cortical histone acetylation shows a similar pattern to the hippocampus. FIG. 21D depicts experimental results demonstrating label incorporation into histone acetylation occurs earlier in the liver, the principal site of alcohol metabolism. FIG. 21E depicts experimental results demonstrating histone acetylation is relatively independent of liver alcohol metabolism in skeletal muscle, a tissue with low expression of ACSS2.

FIG. 22, comprising FIG. 22A through FIG. 22D, depicts histone acetylation of wild-type mice. FIGS. 22A-22C depict mass spectra showing the relative abundance of deuterated histone H4-triacetyl peptide (aa 4-17) in dorsal hippocampus of wild-type mice. FIG. 22A depicts the mass spectrum at baseline. FIG. 22B depicts the mass spectrum at 30 minutes following d6-EtOH injection. FIG. 22C depicts the mass spectrum at 4 hours following d6-EtOH injection. FIG. 22D depicts experimental results demonstrating histone acetylation is relatively independent of liver alcohol metabolism in skeletal muscle. Relative abundance of deuterated histone acetylation in skeletal muscle tissue at 30 minutes and 4 hours in wild type (WT) mice, and 30 minutes in hippocampal ACSS2 KD mice (compare to FIG. 21E).

FIG. 23, comprising FIG. 23A through FIG. 23E, depicts mass spectrometry analysis of EtOH-$d_6$ in a dorsal hippocampus (dHPC) ACSS2 knockdown (KD). FIG. 23A depicts experimental results demonstrating knockdown of ACSS2 expression in dorsal hippocampus prevents incorporation of the heavy label into histone acetylation. FIG. 23B depicts experimental results demonstrating that, in the same animal, incorporation of the heavy label in the ventral hippocampus (where ACSS2 levels are normal) is not changed when compared to control mice. FIG. 23C depicts experimental results demonstrating heavy acetate introduced via intraperitoneal injection readily labels histone acetylation in the dorsal hippocampus. FIG. 23D depicts experimental results demonstrating heavy acetate introduced via intraperitoneal injection readily labels histone acetylation in the cortex. FIG. 23E depicts experimental results demonstrating acetate from hepatic alcohol breakdown is activated by neuronal ACSS2 in the brain and readily induces gene-regulatory histone acetylation.

FIG. 24, comprising FIG. 24A through FIG. 24E, depicts ACSS2 mediated acetate-induced transcription in primary hippocampal neurons. FIG. 24A and FIG. 24B depict RNA-seq in primary hippocampal neurons isolated from C57/Bl6 mouse embryos and treated with acetate (10 mM) in the presence or absence of a small molecular inhibitor of ACSS2 (ACSS2i). FIG. 24A depicts a heatmap showing 7,600 genes differentially expressed upon acetate treatment, and a third column showing the behavior of those genes under in the presence of the ACSS2 inhibitor. 2107 of the 3613 acetate-induced genes fail to be upregulated in the presence of ACSS2i (N=4 per group). FIG. 24B depicts experimental results demonstrating acetate-induced genes were not regulated by ACSS2i treatment in the absence of acetate. FIG. 24C depicts acetate-induced genes in primary hippocampal neurons in blue; shown below the Gene Ontology (GO) term analysis of ACSS2i sensitive genes (non-overlapping with yellow, acetate+ACSS2i). FIG. 24D depicts genes GO term analysis of genes that are both sensitive to acetate and directly bound by ACSS2 (from ACSS2 ChIP-seq). FIG. 24E depicts HOMER unsupervised de novo motif analysis of ACSS2 hippocampal binding sites targeting acetate-sensitive genes.

FIG. 25, comprising FIG. 25A through FIG. 25D, depicts genes regulated by acetate. FIG. 25A depicts RNAseq showing differentially regulated genes in primary hippocampal neurons treated with 10 mM acetate. FIG. 25B depicts gene ontology (GO) analysis of significantly upregulated (red) and significantly downregulated (blue) genes. FIG. 25C experimental results demonstrating 81 out of 214 genes upregulated in the hippocampus of ethanol-injected mice are also upregulated by acetate in primary hippocampal neurons in vitro (p=6.60e-17). FIG. 25D depicts experimental results demonstrating the cumulative number of ACSS2 peaks near the transcription start site (TSS) of acetylated ACSS2i sensitive genes, indicating that the majority ACSS2 binding events occurs over or proximal to the gene promoter.

FIG. 26, comprising FIG. 26A and FIG. 26B, depicts that alcohol metabolites feed histone acetylation in the fetal brain. FIG. 26A depicts experimental results demonstrating metabolized heavy d6-EtOH is incorporated into histone acetylation in the maternal brain. FIG. 26B depicts heavy label incorporation into histone acetylation in the fetal brain. Data represent two pools of four embryos from maternal d6-EtOH injection. The Arachne plot axes represent the percentage of the third isotope of the acetylated peptide, corresponding to the $D_3$ labeled form.

DETAILED DESCRIPTION

Figure 1:
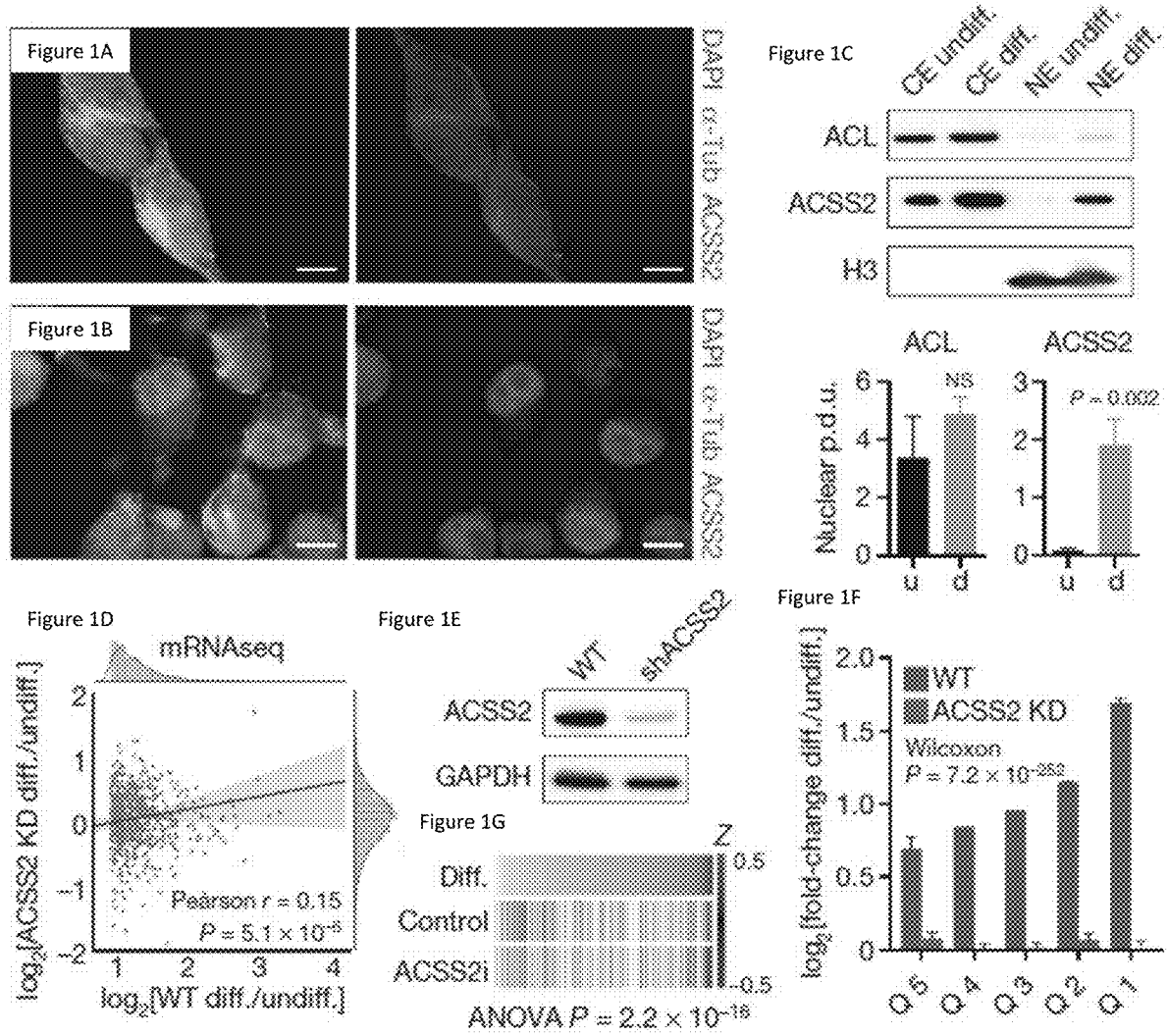
FIG. 1, comprising

The present invention relates to compositions and methods for treating neurological and cognitive diseases and disorders. In some embodiments, the invention provides compositions and methods for treating memory-related diseases and disorders. In various embodiments, the compositions and methods of the invention are useful in treating anxiety diseases and disorders such as phobias, panic disorders, psychosocial stress (e.g. as seen in disaster, catastrophe or violence victims), obsessive-compulsive disorder, generalized anxiety disorder and post-traumatic stress disorder (PTSD). In some embodiments, the compositions and methods of the invention are useful for regulating long term memory storage or consolidation.

The present invention also relates to compositions and methods for treating addiction and/or disease or disorders related to addiction. In various embodiments, the compositions and methods of the invention are useful for preventing or treating acute alcohol induced memory deficit and chronic alcohol induced memory deficit.

In some embodiments, the methods of the present invention comprise modulating chromatin acetylation. In one embodiment, the methods of the invention decrease chromatin acetylation. In one embodiment, the chromatin is neuronal chromatin. In one embodiment, the method comprises administering to a subject an effective amount of a composition comprising an inhibitor of ACSS2.

In certain instances, the compositions and methods described herein relate to inhibiting acetate-dependent acetyl-CoA synthetase 2 (ACSS2). In one embodiment, the composition of the present invention comprises an inhibitor of ACSS2. In one embodiment, the inhibitor of ACSS22 inhibits the expression, activity, or both, of ACSS2.

Definitions

Unless defined otherwise, all technical and scientific terms used herein have the same meaning as commonly understood by one of ordinary skill in the art to which this invention belongs. Any methods and materials similar or equivalent to those described herein can be used in the practice or testing of the present invention.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, NY, and Ausubel et al., 2002, Current Protocols in Molecular Biology, John Wiley & Sons, NY), which are provided throughout this document.

As used herein, each of the following terms has the meaning associated with it in this section.

The articles "a" and "an" are used herein to refer to one or to more than one (i.e., to at least one) of the grammatical object of the article. By way of example, "an element" means one element or more than one element. "About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of a compound which is sufficient to provide a beneficial effect to the subject to which the compound is administered.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The terms "patient," "subject," "individual," and the like are used interchangeably herein, and refer to any animal, or cells thereof whether in vitro or in vivo, amenable to the methods described herein. In certain non-limiting embodiments, the patient, subject or individual is a human.

A "therapeutic" treatment is a treatment administered to a subject who exhibits signs or symptoms of a disease or disorder, for the purpose of diminishing or eliminating those signs or symptoms.

As used herein, "treating a disease or disorder" means reducing the severity and/or frequency with which a sign or symptom of the disease or disorder is experienced by a patient.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprise a second portion, whereby, when the first and second portions are arranged in an antiparallel fashion, at least about 50% of the nucleotide residues of the first portion are capable of base pairing with nucleotide residues in the second portion. In one embodiment, at least about 75%, at least about 90%, or at least about 95% of the nucleotide residues of the first portion are capable of base pairing with nucleotide residues in the second portion. In one embodiment, all nucleotide residues of the first portion are capable of base pairing with nucleotide residues in the second portion.

The term "DNA" as used herein is defined as deoxyribonucleic acid.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "fusion polypeptide" refers to a chimeric protein containing a protein of interest (e.g., luciferase) joined to a heterologous sequence (e.g., a non-luciferase amino acid or protein).

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

An "inducible" promoter is a nucleotide sequence which, when operably linked with a polynucleotide which encodes or specifies a gene product, causes the gene product to be produced substantially only when an inducer which corresponds to the promoter is present.

A "constitutive" promoter is a nucleotide sequence which, when operably linked with a polynucleotide which encodes or specifies a gene product, causes the gene product to be produced in a cell under most or all physiological conditions of the cell.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, a "peptidomimetic" is a compound containing non-peptidic structural elements that is capable of mimicking the biological action of a parent peptide. A peptidomimetic may or may not comprise peptide bonds.

The term "RNA" as used herein is defined as ribonucleic acid.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods.

As used herein, "conjugated" refers to covalent attachment of one molecule to a second molecule.

As used herein, the term "transdominant negative mutant gene" refers to a gene encoding a polypeptide or protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e. $C_1$-6 means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —$NH_2$, amino, azido, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

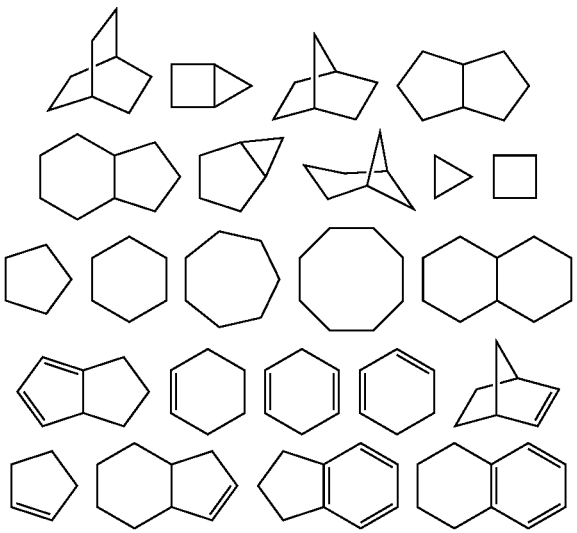

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

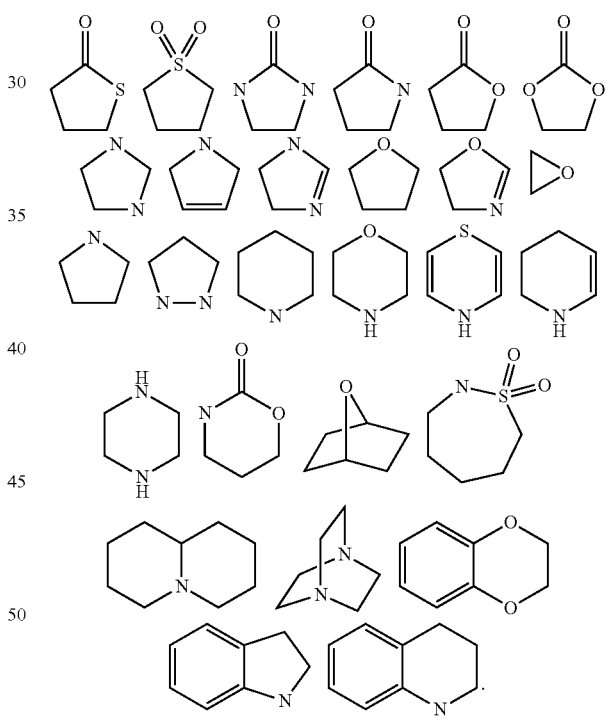

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. In one embodiment, aryl-($C_1$-$C_3$)alkyl is aryl-$CH_2$— or aryl-$CH(CH_3)$—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

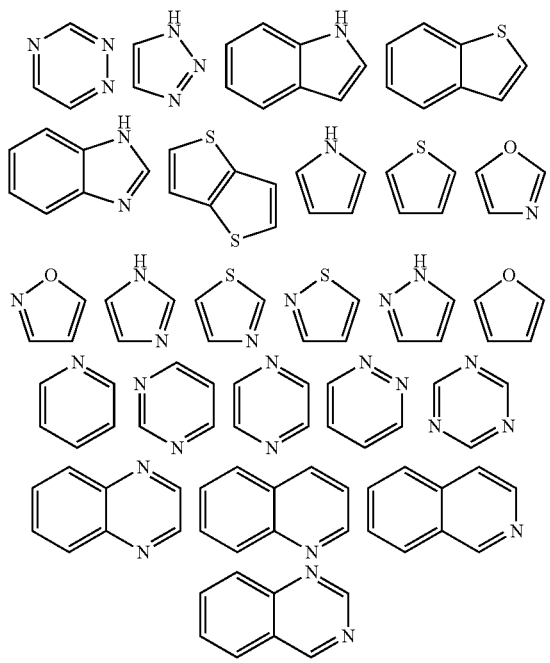

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S($=O$)$_2$alkyl, —C($=O$)NH[substituted or unsubstituted alkyl, or substituted or unsubstituted phenyl], —C($=O$)N[H or alkyl]$_2$, —OC($=O$)N[substituted or unsubstituted alkyl]$_2$, —NHC($=O$)NH [substituted or unsubstituted alkyl, or substituted or unsubstituted phenyl], —NHC($=O$)alkyl, —N[substituted or unsubstituted alkyl]C($=O$)[substituted or unsubstituted alkyl], —NHC($=O$)[substituted or unsubstituted alkyl], —C(OH)[substituted or unsubstituted alkyl]$_2$, and —C($NH_2$)[substituted or unsubstituted alkyl]$_2$. In another embodiment, by way of example, an optional substituent is selected from oxo, fluorine, chlorine, bromine, iodine, —CN, —$NH_2$, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —S($=O$)$_2$—$CH_3$, —C($=O$)$NH_2$, —C($=O$)—$NHCH_3$, —NHC($=O$)$NHCH_3$, —C($=O$)$CH_3$, —$ON(O)_2$, and —C($=O$)OH. In yet one embodiment, the substituents are independently selected from the group consisting of $C_{1-6}$ alkyl, —OH, $C_{1-6}$ alkoxy, halo, amino, acetamido, oxo and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods for treating or preventing a memory-related disease or disorder, such as, but not limited to, PTSD, addiction and addiction-related diseases or disorders. The present invention is based, in part, upon the finding that ACSS2 regulates histone acetylation and neuronal gene transcription. The inhibition of ACSS2 expression (such as by RNA interference) or ACSS2 activity (such as by a small molecule) decreases histone acetylation and impairs long-term spatial memory. Thus, the present invention relates to compositions and method to inhibit ACSS2 in order to inhibit histone acetylation and treat memory-related diseases or disorders.

In some embodiments, the composition of the present invention comprises an inhibitor of ACSS2 activity. In some embodiments, the composition comprises an inhibitor of ACSS2 expression. Thus, in various embodiments, the composition comprises an isolated nucleic acid (e.g., siRNA, miRNA, ribozyme, antisense RNA, etc.) that reduces the expression level of ACSS2 in a cell.

In some embodiments, the composition comprises an inhibitor of ACSS2 activity. Thus, in various embodiments, the composition comprises a small molecule, nucleic acid, peptide, antibody, antagonist, aptamer, or peptidomimetic that reduces the activity of ACSS2.

In some embodiments, the present invention provides a method for treating a neurological or cognitive disease or disorder in a subject. In one embodiment, the neurological or cognitive disease or disorder is a memory-related disease or disorder. In one embodiment, the method comprises administering to a subject an effective amount of a composition comprising an inhibitor of ACSS2. In one embodiment, the method is useful in treating PTSD.

In another embodiment, the present invention provides a method for treating addiction or an addiction related disease or disorder in a subject. In some embodiments, the methods of the invention are useful for treating acute alcohol induced memory deficit. In other embodiments, the methods of the invention are useful for treating chronic alcohol induced memory deficit. In some embodiments, the methods comprise administering to a subject an effective amount of a composition comprising an inhibitor of ACSS2.

Inhibitors

In some embodiments, the present invention provides compositions for treating a neurological or cognitive disease or disorder in a subject. In one embodiment, the neurological or cognitive disease or disorder is a memory-related disease or disorder. In one embodiment, the method comprises administering to a subject an effective amount of a composition comprising an inhibitor of ACSS2. In another embodiment, the present invention provides compositions for treating addiction or an addiction related disease or disorder in a subject. In some embodiments, the methods of the invention are useful for treating acute alcohol induced memory deficit. In other embodiments, the methods of the invention are useful for treating chronic alcohol induced memory deficit.

In certain embodiments, the composition inhibits the expression, activity, or both of ACSS2 in the subject.

In one embodiment, the composition of the invention comprises an inhibitor of ACSS2. In various embodiments, the inhibitor of ACSS2 is any compound, molecule, or agent that reduces, inhibits, or prevents the expression, activity, or function of ACSS2. Thus, an inhibitor of ACSS2 is any compound, molecule, or agent that reduces ACSS2 expression, activity, or both. In various embodiments, the inhibitor of ACSS2 is a nucleic acid, a peptide, a small molecule, a siRNA, a ribozyme, an antisense nucleic acid, an antagonist, an aptamer, a peptidomimetic, or any combination thereof.

Small Molecule Inhibitors

In some embodiments, the inhibitor is a small molecule. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analog or derivative of an inhibitor described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to treat an autoimmune disease or disorder.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

In one embodiment, the small molecule inhibitor is a compound of Formula (1)

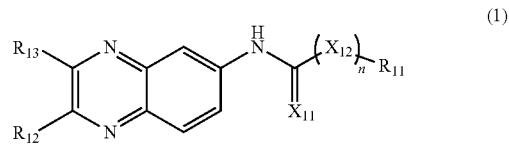

wherein, $X_{11}$ is selected from the group consisting of $C(R_{14})(R_{15})$, O, S and $NR_{15}$;
each occurrence of $X_{12}$ is selected from the group consisting of $C(R_{14})(R_{15})$, O, S and $NR_{15}$;
$R_{11}$ is selected from the group consisting of hydrogen, —$OR_{15}$, alkyl, cycloalkyl, heterocyclyl, aryl, and heteroaryl, wherein $R_{11}$ is optionally substituted;
$R_{12}$ and $R_{13}$ are each independently selected from the group consisting of hydrogen, alkyl, aryl, and heteroaryl, wherein $R_{12}$ and $R_{13}$ are optionally substituted;
each occurrence of $R_{14}$ and $R_{15}$ are independently selected from the group consisting of hydrogen, halogen, —OH, and alkyl; and
n is an integer from 0-8.

In one embodiment, n is 0. In one embodiment, n is 1. In one embodiment, n is 2. In one embodiment, n is 3.

In one embodiment, $R_{11}$ is $OR_{15}$. In one embodiment, $R_{15}$ is alkyl. In one embodiment, $R_{15}$ is methyl.

In one embodiment, $R_{11}$ is piperidinyl.
In one embodiment, $R_{11}$ is morpholinyl.
In one embodiment, $R_{11}$ is pyrrolidinyl.
In one embodiment, $R_{11}$ is furanyl.
In one embodiment, $R_{11}$ is substituted with a hydroxyl group.

In one embodiment, $R_{12}$ is alkyl. In one embodiment, $R_{12}$ is methyl.

In one embodiment, $R_{12}$ is aryl. In one embodiment, $R_{12}$ is phenyl.

In one embodiment, $R_{12}$ is a $C_5$-$C_6$ heteroaryl. In one embodiment, $R_{12}$ is furan. In one embodiment, $R_{12}$ is thiophenyl. In one embodiment, $R_{12}$ is pyridinyl.

In one embodiment, $R_{13}$ is alkyl. In one embodiment, $R_{13}$ is methyl.

In one embodiment, $R_{13}$ is aryl. In one embodiment, $R_{13}$ is phenyl.

In one embodiment, $R_{13}$ is a $C_5$-$C_6$ heteroaryl. In one embodiment, $R_{13}$ is furan. In one embodiment, $R_{13}$ is thiophenyl. In one embodiment, $R_{13}$ is pyridinyl.

In one embodiment, $R_{12}$ and $R_{13}$ are the same.

In one embodiment, the compound of Formula (1) includes, but is not limited to:

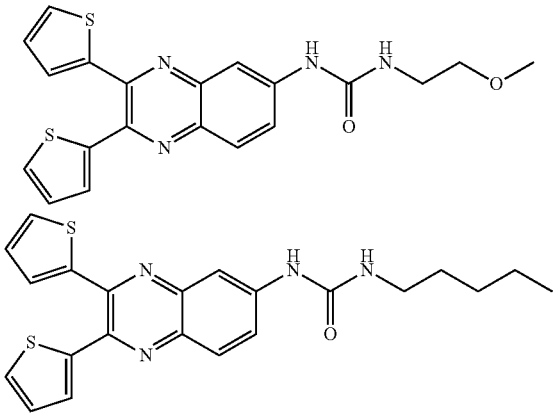

-continued
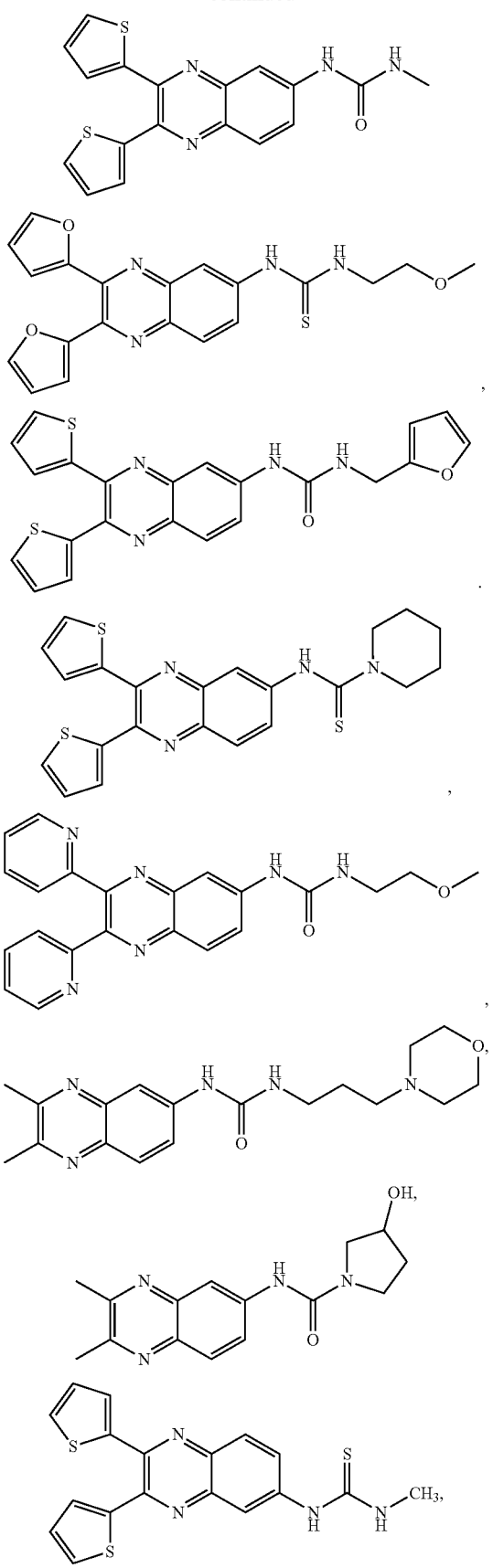
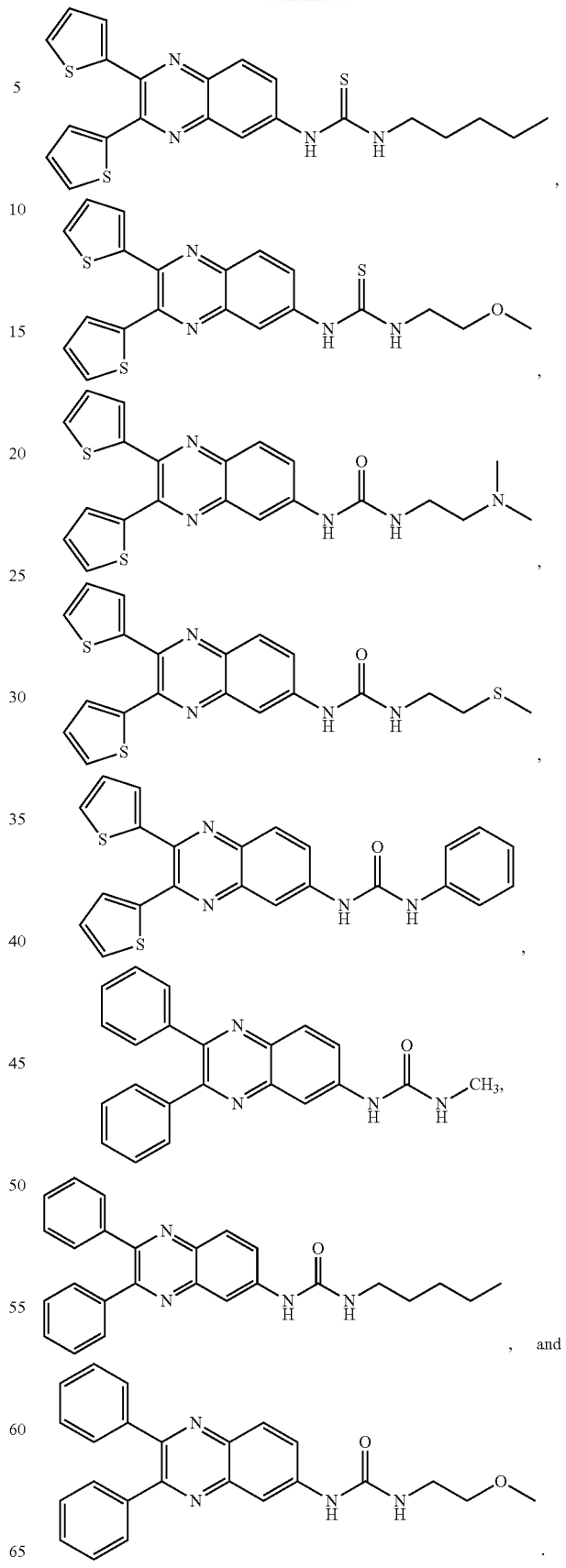

In one embodiment, the small molecule inhibitor is a compound of Formula (2):

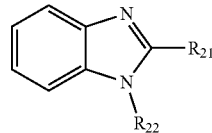
(2)

wherein,
$R_{21}$ is selected from the group consisting of —$C(R_{23})_m$, cycloalkyl, heterocycyl, cycloalkyl-one, and heterocycyl-one;
$R_{22}$ is selected from the group consisting of alkyl, aryl, heteroaryl, alkyl-aryl, and alkyl-heteroaryl;
each occurrence of $R_{23}$ is independently selected from the group consisting of hydrogen, alkyl, aryl, heteroaryl, cycloalkyl, heterocycyl, —OH, and —CN; and
m is an integer from 1 to 3.

In one embodiment, each occurrence of $R_{23}$ is independently selected from the group consisting of phenyl, —OH, methyl, ethyl, and —CN.

In one embodiment, where m is 3, two occurrences of $R_{23}$ are the same and one occurrence of $R_{23}$ is different. In one embodiment, where m is 3, each occurrence of $R_{23}$ is the same.

In one embodiment, $R_1$ is a group represented by Formula (2a)

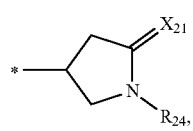
(2a)

wherein $X_{21}$ is selected from the group consisting of O, N or S; and
$R_{24}$ is selected from the group consisting of hydrogen, alkyl, aryl, heteroaryl, cycloalkyl, and heterocycyl.

In one embodiment, the compound of Formula (2) includes, but is not limited to:

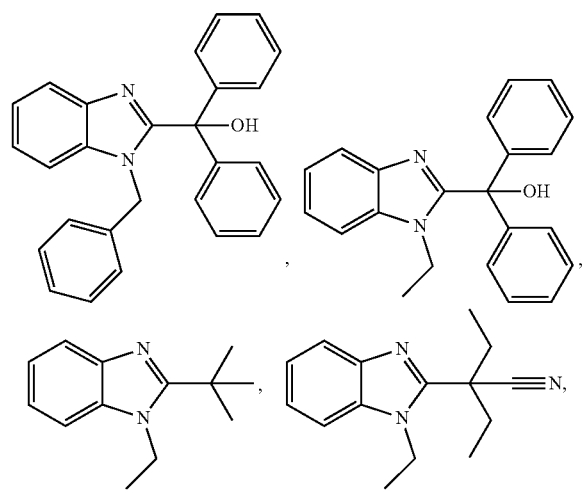

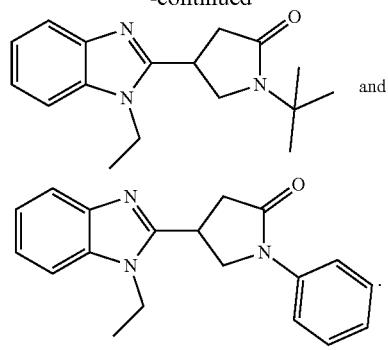

In one embodiment, the small molecule inhibitor is a compound of Formula (3)

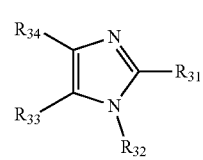
(3)

wherein $R_{31}$ is selected from the group consisting of —$C(R_{35})_p$, cycloalkyl, heterocycyl, cycloalkyl-one, heterocycyl-one;
$R_{32}$ is selected from the group consisting of alkyl, aryl, heteroaryl, —$C_1$-$C_3$ alkyl-($C_3$-$C_6$ aryl), and —$C_1$-$C_3$ alkyl-($C_3$-$C_6$ heteroaryl);
$R_{33}$ and $R_{34}$ are each independently selected from the group consisting of hydrogen, halogen, alkyl, aryl, heteroaryl;
each occurrence of $R_{35}$ is independently selected from the group consisting of hydrogen, alkyl, aryl, heteroaryl, cycloalkyl, heterocycyl, —OH, and —CN; and
p is an integer from 1 to 3.

In one embodiment, $R_{32}$ is ethyl.

In one embodiment, $R_{33}$ and $R_{34}$ are each independently selected from the group consisting of hydrogen and —Cl.

In one embodiment $R_{33}$ and $R_{34}$ are the same.

In one embodiment, each occurrence of $R_{35}$ is independently selected from the group consisting of phenyl, —OH, methyl, ethyl, and —CN.

In one embodiment, where p is 3, two occurrences of $R_{35}$ are the same and one occurrence of $R_{35}$ is different. In one embodiment, where p is 3, each occurrence of $R_{35}$ is the same.

In one embodiment, the compound of Formula (3) includes, but is not limited to:

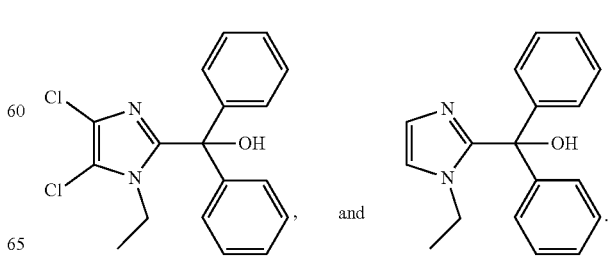

In one embodiment, the small molecule inhibitor is a compound of Formula (4):

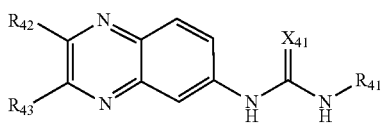

wherein, $X_{41}$ is selected from the group consisting of O and S;

$R_{41}$ is selected from the group consisting of alkyl, cycloalkyl, heterocyclyl, aryl, heteroaryl, and combinations thereof, wherein $R_{41}$ may be optionally substituted; and $R_{42}$ and $R_{43}$ are each independently selected from the group consisting of phenyl, thiophenyl and furanyl.

In one embodiment, $R_{42}$ and $R_{43}$ are the same.

In one embodiment, $R_{41}$ is adamantyl.

In one embodiment, $R_{41}$ is piperidinyl.

In one embodiment, $R_{41}$ is morpholinyl.

In one embodiment, $R_{41}$ is pyrrolidinyl.

In one embodiment, $R_{41}$ is furanyl.

In one embodiment, $R_{41}$ is alkyl. In one embodiment, $R_{41}$ is $C_1$-$C_{25}$ alkyl. In one embodiment, the alkyl is a branched chain alkyl. In one embodiment, the alkyl is a straight chain alkyl.

In one embodiment, $R_{21}$ is —$C_3$-$C_{10}$ cycloalkyl, which may be optionally substituted. In one embodiment, the cycloalkyl group is substituted. In one embodiment, the cycloalkyl group is unsubstituted. In one embodiment, the cycloalkyl group is monocyclic. Non-limiting examples of monocyclic cycloalkyl groups include cyclopropyl, cyclobutyl, cyclopentyl, cyclohexyl, cycloheptyl, cyclooctyl, cyclononyl, cyclodecyl, and the like. In another embodiment, the cycloalkyl group is polycyclic. For example, a polycyclic cycloalkyl group may be formed by joining two or more —$C_3$-$C_{10}$ cycloalkyl groups. Non-limiting examples of polycyclic cycloalkyl groups include adamantane and norbornane. In one embodiment, the cycloalkyl group is adamantane, which may be optionally substituted. Cycloalkyl groups may also be dicyclic including, but not limited to, tetrahydronaphthyl, indanyl, and tetrahydropentalene. In one embodiment, the cycloalkyl group is saturated or partially unsaturated. Non-limiting examples of saturated or partially unsaturated cycloalkyl groups include cyclopentenyl, cyclopentadienyl, cyclohexenyl, cyclohexadienyl, cycloheptenyl, cycloheptadienyl, cycloheptatrienyl, cyclooctenyl, cycloocta-dienyl, cyclooctatrienyl, cycloocta-tetraenyl, cyclononenyl, cyclononadienyl, cyclodecenyl, cyclodekadienyl, cyclooctynyl, cyclononynyl, cyclodecynyl, and the like. In one embodiment, the cycloalkyl group is fused with an aromatic ring In one embodiment, the compound of formula (4) is selected from the group consisting of

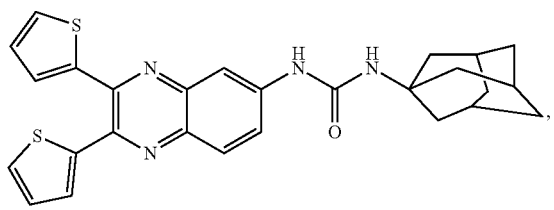

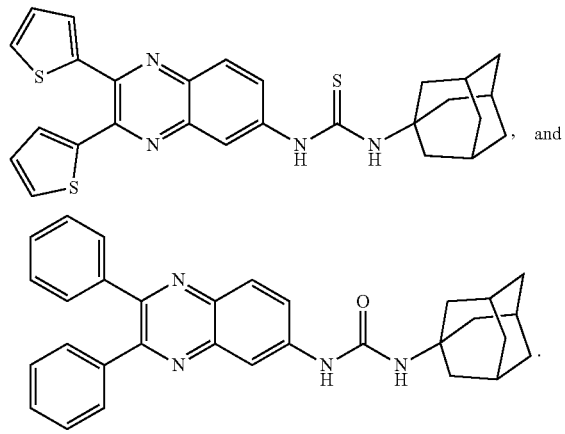

Preparation of the Small Molecule Inhibitors of the Invention

Compounds of Formulae (1)-(4) may be prepared by the general schemes described herein, using the synthetic method known by those skilled in the art. The following examples illustrate non-limiting embodiments of the invention.

In a non-limiting embodiment, the synthesis of compounds of Formulae (1) and (4) is accomplished by treating 4-nitro-o-phenylenediamine (a) with a diketone (b) to form a 6-nitroquinoxaline (c), which is subsequently reduced via Pd/C-catalyzed hydrogenation to produce a 6-aminoquinoxaline (d). A diketone (a) can be produced using a method known in the art (Tet. Lett., 1995, 36:7305-7308, which is incorporated herein by reference in its entirety.

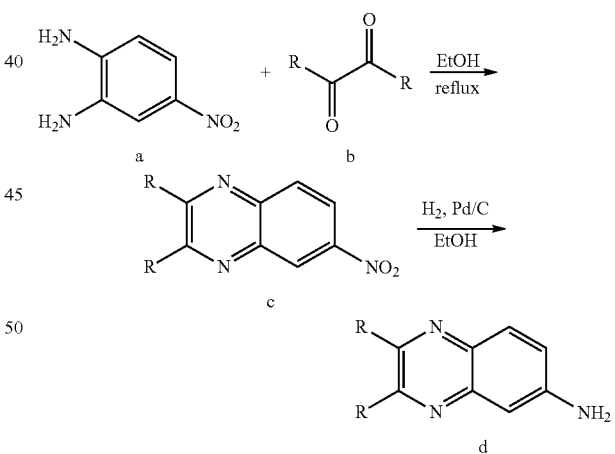

Quinoxaline d is then treated with an isocyanate to form a compound of Formulae (1) or (4).

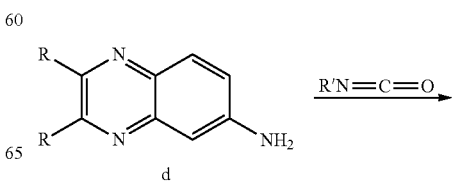

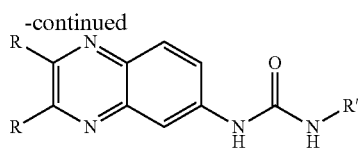

In another non-limiting embodiment, quinoxaline d is first treated with triphosgene, followed by the addition of an amine, to form a compound of Formulae (1) or (4).

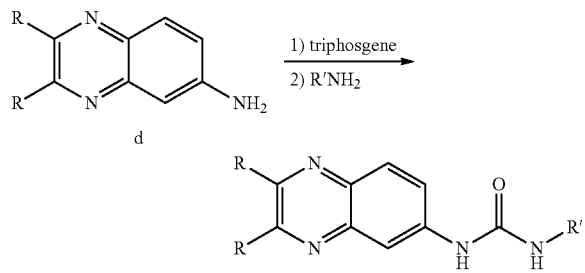

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomers is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water and ethanol. In another embodiment, the compounds described herein exist in unsolvated form.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}$H, $^{3}$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

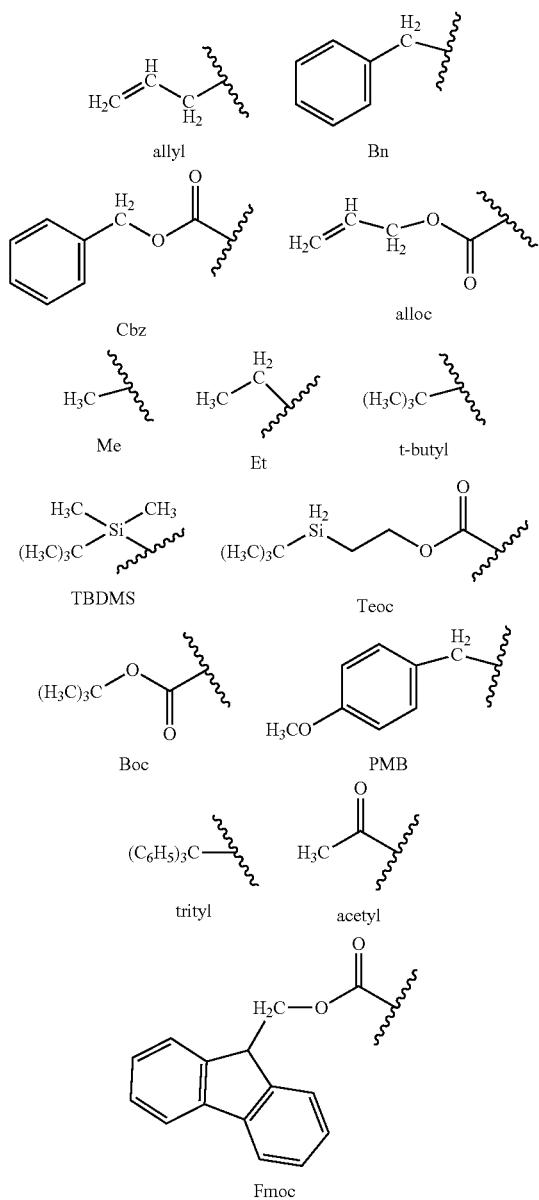

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Nucleic Acid Inhibitors

In some embodiments, the inhibitor is nucleic acid. In various embodiments, the inhibitor is an siRNA, miRNA, shRNA, or an antisense molecule, which inhibits ACSS2. In one embodiment, the nucleic acid comprises a promoter/regulatory sequence such that the nucleic acid is capable of directing expression of the inhibitor nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In another aspect of the invention, ACSS2, can be inhibited by way of inactivating and/or sequestering ACSS2. As such, inhibiting the activity of ACSS2 can be accomplished by using a transdominant negative mutant.

In one embodiment, siRNA is used to decrease the level of ACSS2 protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, NY (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of ACSS2 using RNAi technology.

In another aspect, the invention includes a vector comprising an siRNA or antisense nucleic acid. In one embodiment, the siRNA or antisense polynucleotide is capable of inhibiting the expression of a target polypeptide, wherein the target polypeptide is ACSS2. The incorporation of a desired polynucleotide into a vector and the choice of vectors is well-known in the art as described in, for example, Sambrook et al. (2012), and in Ausubel et al. (1997), and elsewhere herein.

In certain embodiments, the expression vectors described herein encode a short hairpin RNA (shRNA) inhibitor. shRNA inhibitors are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense nucleic acid can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense nucleic, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

By way of illustration, the vector in which the nucleic acid sequence is introduced can be a plasmid, which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2012). In a particular embodiment, the vector is a vector useful for transforming animal cells.

In one embodiment, the recombinant expression vectors may also contain nucleic acid molecules, which encode a peptide or peptidomimetic inhibitor of invention, described elsewhere herein.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene, which facilitates the selection of transformed or transfected host cells. Suitable selectable marker genes are genes encoding proteins such as G418 and hygromycin, which confer resistance to certain drugs, 0-galactosidase, chloramphenicol acetyltransferase, firefly luciferase, or an immunoglobulin or portion thereof such as the Fc portion of an immunoglobulin, for example, IgG. The selectable markers may be introduced on a separate vector from the nucleic acid of interest.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

In one embodiment of the invention, an antisense nucleic acid sequence, which is expressed by a plasmid vector is used to inhibit ACSS2 protein expression. The antisense expressing vector is used to transfect a mammalian cell or the mammal itself, thereby causing reduced endogenous expression of ACSS2.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. In one embodiment, the antisense oligomers are between about 10 to about 30 nucleotides. In one embodiment, the antisense oligomers are about 15 nucleotides. In one embodiment, antisense oligomers of about 10 to about 30 nucleotides are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used to inhibit ACSS2 protein expression. Ribozymes useful for inhibiting the expression of a target molecule may be designed by incorporating target sequences into the basic ribozyme structure, which are complementary, for example, to the mRNA sequence encoding ACSS2. Ribozymes targeting ACSS2, may be synthesized using commercially available reagents (Applied Biosystems, Inc., Foster City, CA) or they may be genetically expressed from DNA encoding them.

In one embodiment, the inhibitor of ACSS2 may comprise one or more components of a CRISPR-Cas system. CRISPR methodologies employ a nuclease, CRISPR-associated (Cas), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas and guide RNA (gRNA) may be synthesized by known methods. Cas/guide-RNA (gRNA) uses a non-specific DNA cleavage protein Cas, and an RNA oligo to hybridize to target and recruit the Cas/gRNA complex. In one embodiment, a guide RNA (gRNA) targeted to a gene encoding ACSS2, and a CRISPR-associated (Cas) peptide form a complex to induce mutations within the targeted gene. In one embodiment, the inhibitor comprises a gRNA or a nucleic acid molecule encoding a gRNA. In one embodiment, the inhibitor comprises a Cas peptide or a nucleic acid molecule encoding a Cas peptide.

Polypeptide Inhibitors

In some embodiments, the inhibitor is a peptide or polypeptide inhibitor that inhibits ACSS2. For example, in one embodiment, the peptide inhibitor of the invention inhibits ACSS2 directly by binding to ACSS2 thereby preventing the normal functional activity of ACSS2. In another embodiment, the peptide inhibitor of the invention inhibits ACSS2 by competing with endogenous ACSS2. In yet another embodiment, the peptide inhibitor of the invention inhibits the activity of ACSS2 by acting as a transdominant negative mutant.

Variants of the peptides and polypeptides according to the present invention may be (i) one in which one or more of the amino acid residues are substituted with a conserved or non-conserved amino acid residue and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Antibody Inhibitors

In some embodiments, the inhibitor is an antibody, or antibody fragment. In some embodiments, the inhibitor is an antibody, or antibody fragment, that specifically binds to ACSS2. That is, the antibody can inhibit ACSS2 to provide a beneficial effect.

The antibodies may be intact monoclonal or polyclonal antibodies, and immunologically active fragments (e.g., a Fab or (Fab)$_2$ fragment), an antibody heavy chain, an antibody light chain, humanized antibodies, a genetically engineered single chain Fv molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, humanized antibodies, fragments and chimeras, may be prepared using methods known to those skilled in the art.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker. Bispecific antibodies can comprise a first antigen-binding site that specifically binds to a first target and a second antigen-binding site that specifically binds to a second target, with particularly advantageous properties such as producibility, stability, binding affinity, biological activity, specific targeting of certain T cells, targeting efficiency and reduced toxicity. In some instances, there are bispecific antibodies, wherein the bispecific antibody binds to the first target with high affinity and to the second target with low affinity. In other instances, there are bispecific antibodies, wherein the bispecific antibody binds to the first target with low affinity and to the second target with high affinity. In other instances, there are bispecific antibodies, wherein the bispecific antibody binds to the first target with a desired affinity and to the second target with a desired affinity.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Combinations

In some embodiments, the compositions of the present invention comprise a combination of ACSS2 inhibitors described herein. In certain embodiments, a composition comprising a combination of inhibitors described herein has an additive effect, wherein the overall effect of the combination is approximately equal to the sum of the effects of each individual inhibitor. In other embodiments, a composition comprising a combination of inhibitors described herein has a synergistic effect, wherein the overall effect of the combination is greater than the sum of the effects of each individual inhibitor.

In some embodiments, the composition of the present invention comprises a combination of an ACSS2 inhibitor and second therapeutic agent. For example, in one embodiment the second therapeutic agents include, but are not limited to, a PTSD treatment, an anxiety treatment, and a substance abuse treatment.

In some embodiments, the second therapeutic is a PTSD treatment. Exemplary therapeutics include, but are not limited to, anti-anxiety treatments, antidepressants, and adrenergic agents. In one embodiment, the PTSD treatment is a therapy treatment. For example, in one embodiment the PTSD treatment includes, psychotherapy, behavioral or cognitive behavioral therapy, eye movement desensitization and reprocessing (EMDR) group therapy, transcranial magnetic stimulation, deep brain stimulation and neurofeedback techniques, and medications including ketamine and d-cycloserine.

In one embodiment, administration of the ACSS2 inhibitor in the emergency room or in intensive care units can be used for PTSD prophylaxis. In the peritraumatic phase, reactivated memory traces are vulnerable to disruption, thus ACSS2 inhibition offers the potential to affect reconsolidation of trauma memories.

In some embodiments, the second therapeutic is a substance abuse treatment. For example, in one embodiment the substance abuse treatment includes, but is not limited to, naltrexone, disulfiram, acamprosate, topiramate, nicotine replacement therapy, nicotinic receptor antagonists, nicotinic receptor partial agonists, suboxone, levomethadyl acetate, dihydrocodeine, buprenorphine, ketamine, methadone, and dihydroetorphine.

A composition comprising a combination of inhibitors comprises individual inhibitors in any suitable ratio. For example, in one embodiment, the composition comprises a 1:1 ratio of two individual inhibitors. However, the combination is not limited to any particular ratio. Rather any ratio that is shown to be effective is encompassed.

Methods

In some embodiments, the invention provides methods of inhibiting the ACSS2 in a subject in need thereof. In one embodiment, the method comprises administering to the subject an effective amount of a composition comprising an ACSS2 inhibitor.

In one embodiment, the invention provides a method for modulating chromatin acetylation in a subject. In one embodiment, the chromatin acetylation is histone acetylation. In one embodiment, the chromatin is neural chromatin. In one embodiment, methods of the invention modulate neuronal plasticity in a subject. In one embodiment, the method comprises administering to a subject an effective amount of a composition comprising an inhibitor of ACSS2. In one embodiment, the inhibitor of ACSS2 decreases histone acetylation.

In one aspect, the present invention provides a method for treating neurological or cognitive disease or disorder in a subject. In one embodiment, the neurological or cognitive disease or disorder is a memory-related disease or disorder. In one embodiment, the neurological or cognitive disease or disorder is a neuropsychiatric disorder. For example, in one embodiment the neuropsychiatric disorder includes, but is not limited to, anxiety disorders, psychotic disorders, mood disorders and somatoform disorders.

Exemplary neurological or cognitive diseases or disorders include, but are not limited to, post-traumatic stress disorder (PTSD), bipolar disorder, depression, Tourette's Syndrome, schizophrenia, obsessive-compulsive disorder, generalized anxiety disorder, panic disorders, phobias, personality disorders, including antisocial personality disorder, and other disorders involving troubling memories. In one embodiment, the neurological or cognitive diseases or disorders is PTSD.

In another embodiment, the present invention provides a method for treating addiction or an addiction related disease or disorder in a subject. In one embodiment, the addiction includes, but is not limited to, addiction to: alcohol, tobacco, opioids, sedatives, hypnotics, anxiolytics, cocaine, cannabis, amphetamines, hallucinogens, inhalants, phencyclidine, impulse control disorders and behavioral addictions.

In one embodiment, the addiction is an alcohol addiction. In one embodiment, the method of the invention treats acute and/or chronic alcohol induced memory deficit.

In one embodiment, the invention provides a method for treating alcohol-related memory and cue-induced craving in augmented psychotherapy. In one embodiment, the method comprises administering to a subject an effective amount of a composition comprising an inhibitor of ACSS2. In one embodiment, the inhibitor of ACSS2 decreases histone acetylation.

In one embodiment, the method comprises administering to the subject an effective amount of a composition that reduces or inhibits the expression or activity of ACSS2.

One of skill in the art will appreciate that the inhibitors of the invention can be administered singly or in any combination. Further, the inhibitors of the invention can be administered singly or in any combination in a temporal sense, in that they may be administered concurrently, or before, and/or after each other. One of ordinary skill in the art will appreciate, based on the disclosure provided herein, that the inhibitor compositions of the invention can be used to prevent or to treat an autoimmune disease or disorder, and that an inhibitor composition can be used alone or in any combination with another modulator to affect a therapeutic result. In various embodiments, any of the inhibitor compositions of the invention described herein can be administered alone or in combination with other modulators of other molecules associated with autoimmune diseases.

In one embodiment, the invention includes a method comprising administering a combination of inhibitors described herein. In certain embodiments, the method has an additive effect, wherein the overall effect of the administering a combination of inhibitors is approximately equal to the sum of the effects of administering each individual inhibitor. In other embodiments, the method has a synergistic effect, wherein the overall effect of administering a combination of inhibitors is greater than the sum of the effects of administering each individual inhibitor.

The method comprises administering a combination of inhibitors in any suitable ratio. For example, in one embodiment, the method comprises administering two individual inhibitors at a 1:1 ratio. However, the method is not limited to any particular ratio. Rather any ratio that is shown to be effective is encompassed.

Pharmaceutical Compositions and Formulations

The invention also encompasses the use of pharmaceutical compositions of the invention or salts thereof to practice the methods of the invention. Such a pharmaceutical composition may consist of at least one modulator (e.g., inhibitor) composition of the invention or a salt thereof in a form suitable for administration to a subject, or the pharmaceutical composition may comprise at least one modulator (e.g., inhibitor) composition of the invention or a salt thereof, and one or more pharmaceutically acceptable carriers, one or more additional ingredients, or some combination of these. The compound of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. An exemplary preservative is a combination of about 0.5% to 2.0% benzyl alcohol and 0.05% to 0.5% sorbic acid.

In one embodiment, the composition includes an antioxidant and a chelating agent that inhibits the degradation of the compound. Exemplary antioxidants for some compounds include BHT, BHA, alpha-tocopherol and ascorbic acid in the preferred range of about 0.01% to 0.3%. In one embodiment, the antioxidant is BHT in the range of 0.03% to 0.1% by weight by total weight of the composition. In one embodiment, the chelating agent is present in an amount of from 0.01% to 0.5% by weight by total weight of the composition. Exemplary chelating agents include edetate salts (e.g. disodium edetate) and citric acid in the weight range of about 0.01% to 0.20%. In one embodiment, the chelating agent is in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agents, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, for example, a mammal, including a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Routes of administration of any of the compositions of the invention include oral, nasal, parenteral, sublingual, transdermal, transmucosal (e.g., sublingual, lingual, (trans)buccal, and (intra)nasal,), intravesical, intraduodenal, intragastrical, rectal, intra-peritoneal, subcutaneous, intramuscular, intradermal, intra-arterial, intravenous, or administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Acetyl-CoA Synthetase Regulates Histone Acetylation and Hippocampal Memory Metabolic production of acetyl coenzyme A (acetyl-CoA) is linked to histone acetylation and gene regulation, but the precise mechanisms of this process are largely unknown. The data presented herein demonstrates that the metabolic enzyme acetyl-CoA synthetase 2 (ACSS2) directly regulates histone acetylation in neurons and spatial memory in mammals. In a neuronal cell culture model, ACSS2 increases in the nuclei of differentiating neurons and localizes to upregulated neuronal genes near sites of elevated histone acetylation. A decrease in ACSS2 lowers nuclear acetyl-CoA levels, histone acetylation, and responsive expression of the cohort of neuronal genes. In adult mice, attenuation of hippocampal ACSS2 expression impairs long-term spatial memory, a cognitive process that relies on histone acetylation. A decrease in ACSS2 in the hippocampus also leads to defective upregulation of memory-related neuronal genes that are pre-bound by ACSS2. These results reveal a connection between cellular metabolism, gene regulation, and neural plasticity and establish a link between acetyl-CoA generation 'on-site' at chromatin for histone acetylation and the transcription of key neuronal genes.

The observation that ACSS2 is highly expressed in the mouse hippocampus (Lein, E. S. et al., 2007, Nature, 445: 168-176) led us to investigate the role of ACSS2 in neuronal histone acetylation and gene expression. These findings support the hypothesis that neuronal ACSS2 has a critical function in linking acetate metabolism to neuronal gene regulation through direct binding of chromatin by ACSS2, and identify a prominent role of this mechanism in hippocampal memory consolidation.

The materials and methods employed in these experiments are now described.

Mouse Experiments.

No Statistical Methods were Used to Predetermine Sample Size; Prior experiments using the relevant behavioral assays with pharmacological or genetic manipulations determined that effects are achieved when group sizes are at least 7-9 animals. The experiments were randomized and the investigators were blinded to allocation during experiments and outcome assessment.

Cell Culture

CAD cells (Cath.-a-differentiated) were grown in Dulbecco's modified Eagle's medium (DMEM):Ham's F12 (1:1), supplemented with 2 mM glutamine, 1% penicillin/streptomycin, and 10% fetal bovine serum (FBS). To induce neuronal differentiation, sub-confluent CAD cell cultures (50-60%) were transferred to serum-free medium (DMEM: Ham's F12 (1:1) supplemented with 2 mM glutamine) and maintained in 15-cm$^2$ culture dishes for 5 days. Upon differentiation, CAD neurons exhibit morphological changes that are characteristic of neurons. For knockdown experiments, CAD cells were infected with lentiviral hairpin constructs (TRC collection) designed against ACL (#TRCN0000055217) or ACSS2 (#TRCN0000076124, #TRCN0000076125) in medium containing 8 mg/mL polybrene and 10% FBS for 24 hours. Cells then underwent selection in culture medium supplemented with 0.5 mg/mL puromycin for 5 days to obtain a stably infected population. Cell treatment with ACSS2i (1-(2,3-di(thiophen-2-yl)quinoxalin-6-yl)-3-(2-methoxyethyl)urea (DMSO)) was carried out for 24 hours at a final concentration of 20 µM (treatment with DMSO alone served as control).

RNA-Seq

To generate libraries for RNA-seq, poly(A)$^+$ RNA was extracted using the Dynabeads mRNA Direct kit (Ambion) according to the manufacturer's instructions. RNA-seq libraries for scrambled control (referred to as wild-type), shACL, and shACSS2 were made using a ScriptSeq v2 RNA-seq Library Preparation Kit (Illumina). The quantity and quality of the libraries were assessed by BioAnalyzer (Agilent) and qPCR (Kapa Biosystems). The multiplexed libraries were pooled and sequenced on a single lane on the Illumina NextSeq 500 platform (50 bp, single-end reads). All RNA-seq data were prepared for analysis as follows: NextSeq sequencing data was demultiplexed using bcl2fastq2-v02.14.01.07. Demultiplexed FASTQs were aligned by RNA-STAR 2.3.0.e using the genome index mm10 generated from iGenome UCSC mm10 FASTQ genome sequence. The aligned reads were mapped to genomic features using cufflinks-2.2.1, (-G parameter to quantify only known features), and iGenomes mm10 UCSC genomic transcript loci. The rRNA, mRNA, and tRNA of the mouse genome were downloaded from the goldenPath UCSC FTP and were masked from the transcript quantification. After quantification, all data processing was done using python pandas library v.0.14.0. Differential expression in CAD neurons was defined as the top 10% of genes by fold-change, corresponding roughly to 1.6-fold upregulation or higher. Differential expression in the inhibitor and the hippocampal ACSS2 knockdown in vivo were defined using Cuffdiff. The relationship between CAD cell differentiation and inhibitor function (FIG. 1G) was inferred by assessing standardized scores over two RNA-seq replicates each of untreated and ACSS2i-treated cells. These were averaged and genes with |z|<0.5 in either condition were dropped. Scores for remaining genes were plotted in order of increasing CAD differentiation fold-change. The statistical significance of the trend and reproducibility were assessed by taking the top 20% of genes by loss of expression in the knockdown and comparing the expression of these genes in inhibitor-treated cells to a random sample of genes outside this set (Mann-Whitney test).

ChIP-Seq

Figure 3:
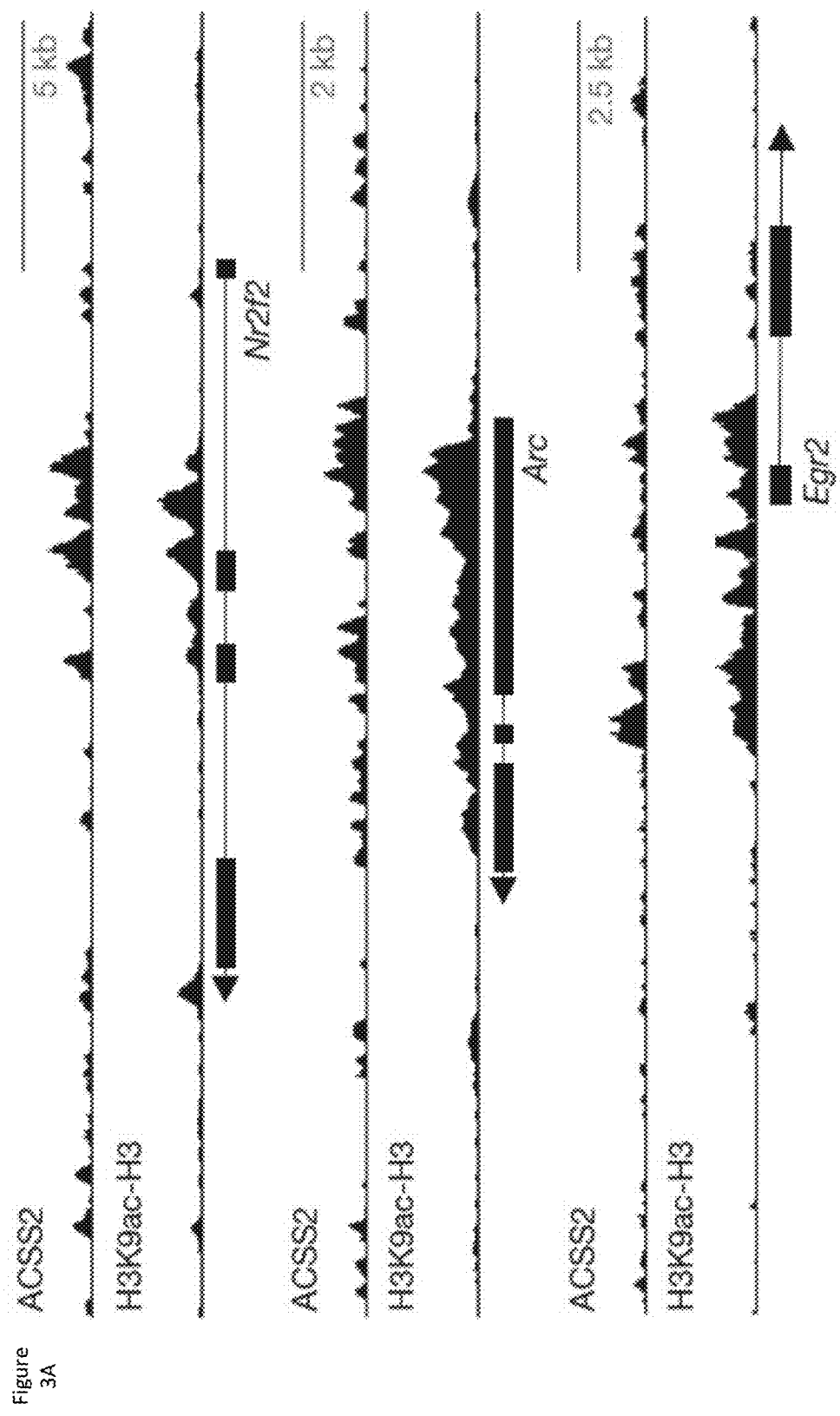
FIG. 3, comprising
Figure 3:
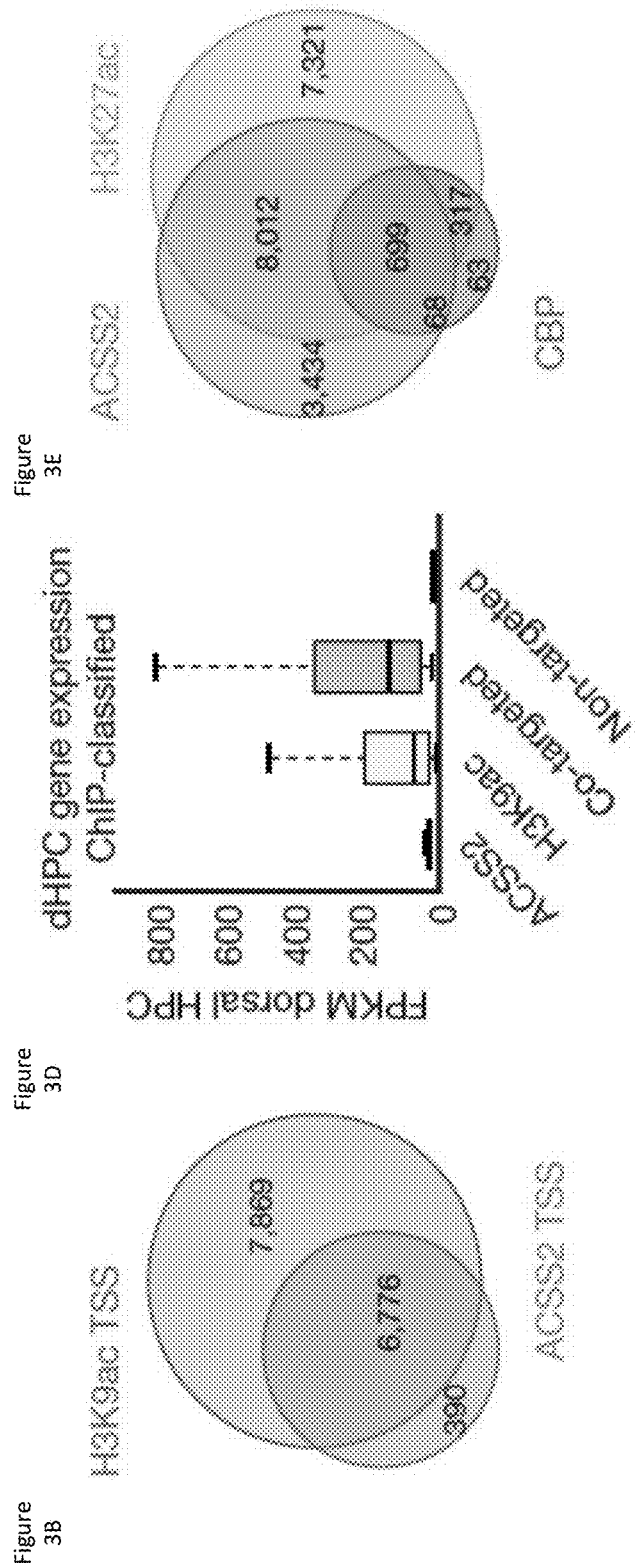
Figure 3:
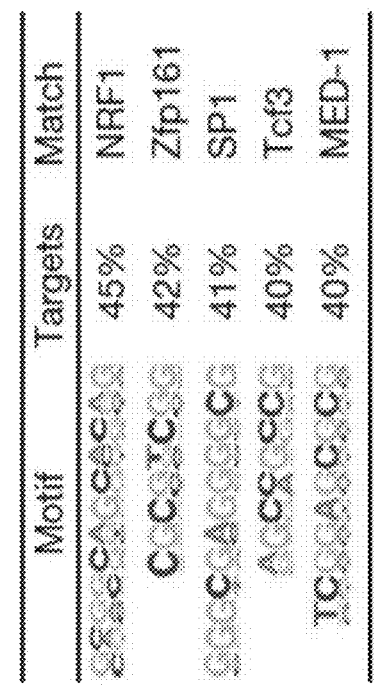
Figure 3:
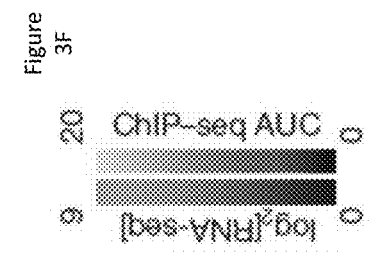
Figure 3:
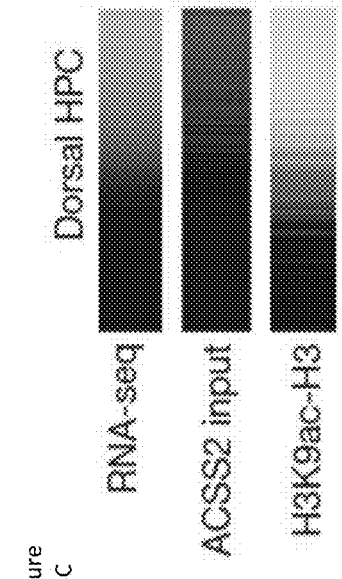
Figure 9:
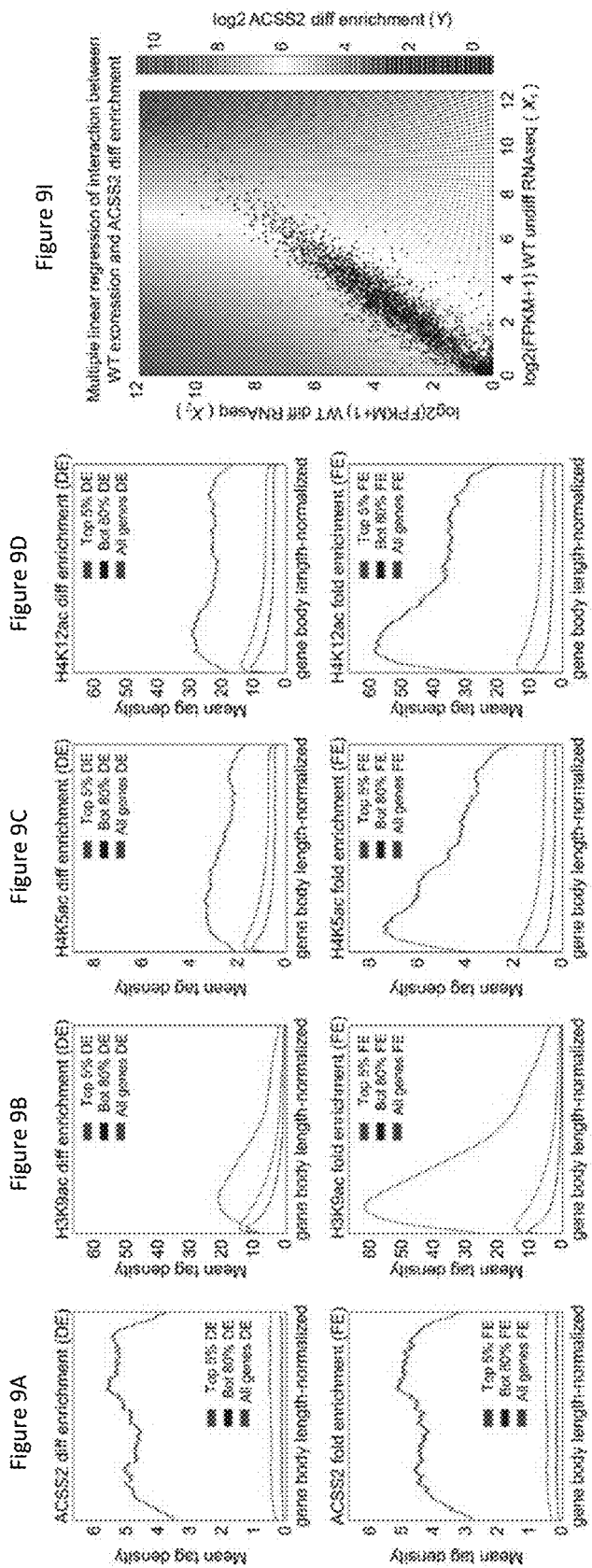
FIG. 9, comprising

CAD cells were fixed in 1% formaldehyde for 10 min and fixation was quenched with the addition of glycine to 125 mM for an additional 5 min. Cells were harvested by scraping from plates, and washed twice in 1×PBS before storage at −80° C. ChIP was performed as previously described (Shah, P. P. et al., 2013, Genes Dev., 27:1787-1799), except that chromatin was sheared to an average size of <500 bp using the Covaris S220 Ultrasonicator. Equal aliquots of sonicated chromatin from undifferentiated and differentiated CAD neurons were used for each immunoprecipitation reaction, and 10% of the amount was saved as input. ACSS2 ChIPs were performed using 2,000 µg extract and 4 µg antibody per sample; all other ChIPs were performed using 500 µg extract and 4 µg antibody per sample. Immunoprecipitation was performed using protein A Dynabeads (Life Technologies). Sequencing libraries were prepared using NEBNext Ultra library preparation procedure, and then assessed for quality and quantity by BioAnalyzer (Agilent) and qPCR (Kapa Biosystems). Sequencing was performed on the Illumina NextSeq 500 platform. All ChIP-seq data were prepared for analysis as follows: NextSeq sequencing data was demultiplexed using bcl2fastq. All reads were aligned to the mm9 or the mm10 reference genome using bowtie2.2.1. One alignment was allowed per read and one mismatch was allowed in the seed region (-N1-k1). Reads were tabulated in fixed windows or to genes provided in the iGenome mm10 UCSC annotations using featureCounts from the subread 1.4.6 software package. CAD cell ACSS2 ChIP-seq data were normalized to input controls, while all histone acetylation ChIP-seq data were H3-subtracted. The plot in FIG. 9I is the result of performing a multiple linear regression to determine the relationship between expression in undifferentiated and differentiated CAD cells (regressors) and enrichment of ACSS2 in differentiated CAD cells (target). The relationship was used to color the negative space in the plot by propensity for ACSS2 binding. For the in vivo ChIP, hippocampal tissue pooled from two animals was finely minced and cross-linked with formaldehyde (1% final concentration) for 15 min at room temperature, followed by glycine quenching for an additional 10 min at 4° C. To create a single-cell suspension, samples were washed once with ice-cold PBS and homogenized by passing through a 22 G needle 10 times. Subsequent steps were performed in the same way as described for the in vitro ChIP. In vivo ChIP peaks (ACSS2 (T), H3K9ac, CBP-GSM1629373, and H3K27ac-GSM1629397) were called using MACS v2.1.0 with the false discover rate (FDR) controlled at 1%. Peak scores were assessed by adjusting to millions of aligned tags and subtracting background. Tracks were similarly normalized and are visualized using the UCSC genome browser with a maximum value windowing function and smoothing at 5 pixels (in vitro ChIP-seq) or using default parameters (in vivo ChIP-seq). The Venn diagram in FIG. 3B shows overlap of genes (official gene symbol) that feature ChIP-seq peaks within 1 kb of their nearest TSS. Venn diagrams in FIG. 3E and FIG. 11B display overlapping target gene sets (RefSeq transcripts) that were assigned to the entire set of ChIP-seq peaks, because CBP binds to few genes within 1 kb of the TSS. The in vivo mRNA expression versus ChIP analysis (FIG. 3C) was created by sorting genes on log 2-transformed expression values (DESeq library-size adjusted, replicate-averaged values) in home cage control mice then displaying ChIP-seq AUCs (RPM-adjusted ChIP minus RPM-adjusted background, length adjusted) for each gene for the peak closest to its TSS within a distance of 1 kb (all genes with more distant peaks were rendered as having a score of zero). Gene targets were inferred by the presence of peaks proximal to the TSS (within 1 kb). To identify enriched motifs (FIG. 3F), in vivo ACSS2 peaks targeting genes that were upregulated in differentiated CAD cells (without respect for distance to the nearest TSS) were compared to a background set of equal-sized regions selected from gene-rich regions using HOMER (peak sizes were fixed at 300 bp). Discovered motifs were filtered for those present at one-third or more of the targeting peaks and with a tenfold or higher enrichment over the gene-rich background. To assess the overlap of ACSS2 and histone acetylation (FIG. 7F, FIG. 7G), ACSS2 peaks were filtered to include only those upstream of their nearest target genes. Downstream acetylation was assessed for similarly filtered peaks of H3K9ac, H4K5ac, and H4K12ac from the same cells, as well as cortical H3K27ac. For the in vivo analysis (FIG. 3B), gene targets of ACSS2 or H3K9ac peaks within 1 kb of their nearest TSS were examined for overlap. The acetylation pattern due to differentiation at induced or inhibitor-sensitive genes (FIG. 3D, FIG. 7P) was assessed by taking a 20-kb window around the TSS and measuring the input-adjusted ChIP-seq signal. H3K9ac data were validated (FIG. 11A) by comparing to ENCODE's common-replicate peaks for H3K9ac in mouse forebrain (accession ENCSR369RBO) using CEAS (default parameters, with a 1-10 kb window around the TSS and TES). Additional comparisons were made to H3K9ac (NCBI GEO: GSE82643) and H3K27ac (GSE82428), contrasting to input (GSE82659) to control for sonication efficiency. Cortical H3K27ac (NCBI GEO: GSM1629397) and CBP (GSM1629373) were aligned along with the corresponding input (GSM1629381) using bowtie2 (parameters-k 1-N 1-local) and peaks were called using MACS2 (input control, FDR controlled at 1%) (FIG. 3E, FIG. 11B). The combined effect of ACSS2 and histone acetylation targeting on gene expression in vivo (FIG. 3D) was demonstrated by box-plotting expression in home cage control mice at genes targeted by ACSS2 by itself, H3K9ac by itself, ACSS2+H3K9ac, or neither. Only genes bound at the promoter (1 kb distance) by ACSS2 were considered.

Acetyl-CoA Quantification

To extract and quantify acetyl-CoA from differentiated CAD neurons, $4 \times 10^6$ cells were washed and incubated in lysis buffer for 30 min (10 mM Tris pH 8, 1 mM KCl, 1.5 mM $MgCl_2$, 1 mM DTT). The nuclei were pelleted at 3,000 g for 5 min, and immediately re-suspended in Acetyl CoA Assay Buffer provided in the PicoProbe Acetyl CoA Assay Kit (Abcam, ab87546). The acetyl-CoA assay, including the deproteinization step, was prepared according to the manufacturer's instructions. The PicoProbe assay was performed in 96-well clear-bottom plates, and the resulting fluorescence was quantified using the Synergy HTX Multi-Mode Microplate Reader (BioTek Instruments).

Western Blots

Figure 14:
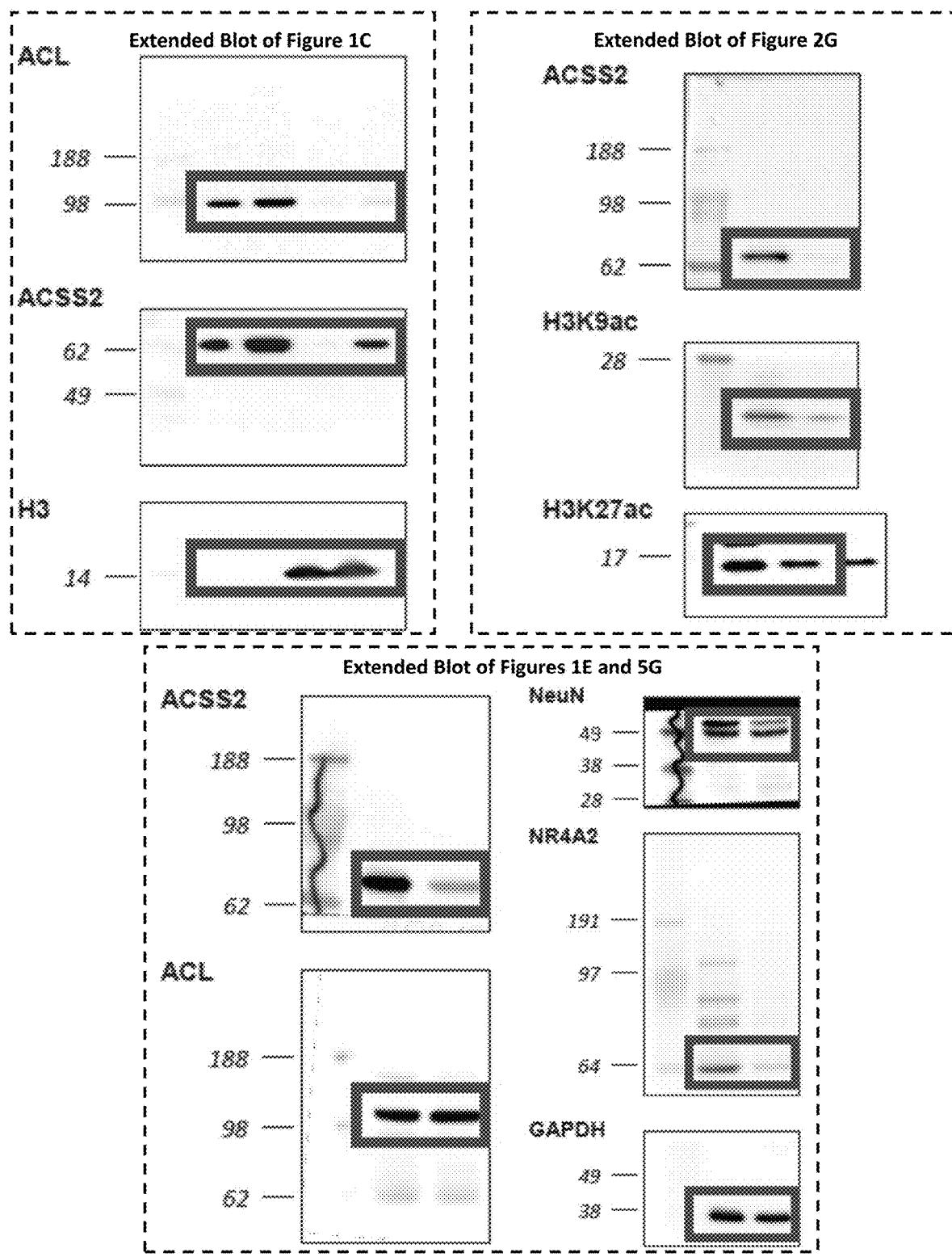
FIG. 14 depicts the original gel blots of the western blots depicted in FIGS. 1C, 2G, 1E and 5G. Boxes depict the cropped area shown in FIGS. 1C, 2G, 1E and 5G.
Figure 15:
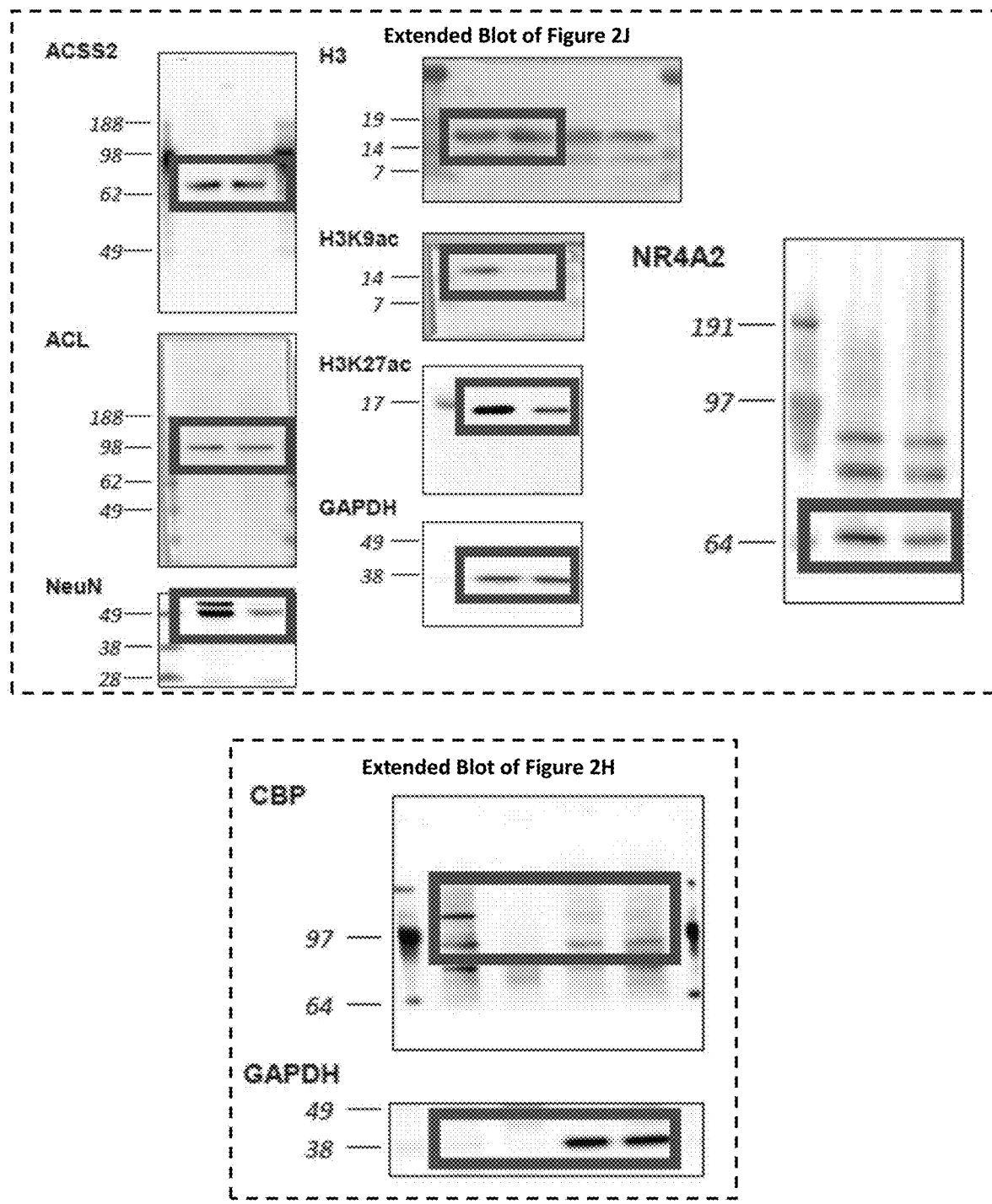
FIG. 15 depicts the original gel blots of the western blots depicted in FIGS. 2H and 2J. Boxes depict the cropped area shown in FIGS. 2H and 2J.
Figure 16:
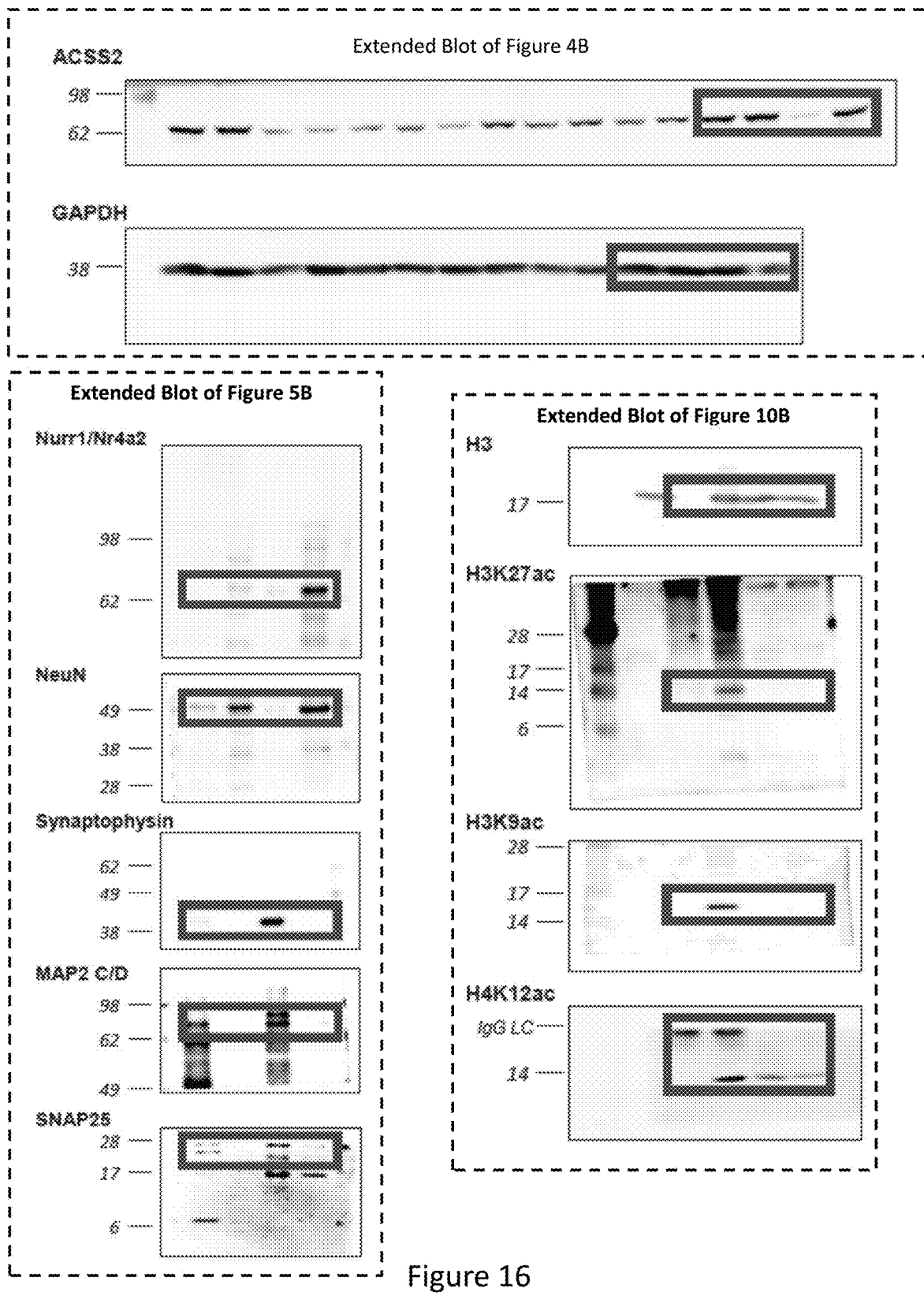
FIG. 16 depicts the original gel blots of the western blots depicted in FIGS. 4B, 5B and 10B. Boxes depict the cropped area shown in FIGS. 4B, 5B and 10B.

Cells were lysed in buffer containing 50 mM Tris pH 8.0, 0.5 mM EDTA, 150 mM NaCl, 1% NP40, 1% SDS, supplemented with protease inhibitor cocktail (Life Technologies, number 78446). For subcellular fractionation experiments, the cells were processed using the subcellular fractionation kit for cultured cells (Thermo Scientific, number 78840) according to the manufacturer's instructions. Protein concentration was determined by BCA protein assay (Life Technologies, number 23227), and equal amounts of protein were used in co-immunoprecipitation experiments or directly loaded onto polyacrylamide gels. The endogenous co-immunoprecipitation experiments were performed using antibody-conjugated protein A Dynabeads (Life Technologies) in buffer containing: 20 mM Tris, pH 8.0, 137 mM NaCl, 1 mM $MgCl_2$, 1 mM $CaCl_2$, 1% NP-40, 10% glycerol, with protease and phosphatase inhibitors, and 12.5 U/mL benzonase (Novagen, 70746). Proteins or co-immunoprecipitation eluates were loaded and separated on 4-12% Bis-Tris polyacrylamide gels (NuPAGE). After transfer to nitrocellulose membrane, 3% BSA in TBS supplemented with 0.1% Tween 20 (TBST) was used to block the membrane at room temperature for 1 hour. Primary antibodies were diluted in TBST, and incubated at 4° C. overnight. Primary antibodies are listed below. The membrane was washed three times with TBST, each for 10 min, followed by incubation with HRP-conjugated secondary antibodies at room temperature for 1 hour, in TBST. The membrane was washed again three times, and imaged with a Fujifilm LAS-4000 imager. Original gel blots are provided as FIGS. 14-16.

Immunofluorescence

Cells were fixed in 4% PFA in PBS for 20 min at room temperature. Cells were washed twice with PBS and permeabilized with 0.5% Triton X-100 in PBS for 10 min. After being washed twice, cells were blocked in 10% BSA in PBS for 1 hour at room temperature. Cells were incubated with primary antibodies in 5% BSA in PBS supplemented with 0.1% Tween 20 (PBST) overnight at 4° C. Antibodies are listed below. Then cells were washed four times with PBST, each for 10 min, followed by incubation with fluorophore-conjugated secondary antibody in 5% BSA in PBST for 1 hour at room temperature. F-actin was labelled using Alexa Fluor 488 Phalloidin (Thermo A12379). Cells were then washed three times in PBST, once with PBS, and incubated with 1 μg/mL DAPI for 5 min. The cells were then washed twice with PBS and mounted with ProLong Gold (Invitrogen). The slides were observed and imaged using a Nikon Eclipse microscope. Microscopy settings were unchanged between samples.

Antibodies

The antibodies used were anti-H3 (Abcam ab1791), anti-H3K9ac (Abcam ab4441), anti-H3K27ac (Abcam ab4729), anti-H3K122ac (Abcam ab33308), anti-H4 (Millipore 05-858), anti-H4K5ac (Millipore 39-584), anti-H4K12ac (Abcam ab1761), anti-ACSS2 (T) (Thermo MA5-145810), anti-ACSS2 (CS) (Cell Signaling 3658), anti-ACL (Proteintech 15421-1-AP), anti-α-tubulin (Sigma T8328), anti-GAPDH (Fitzgerald Industries 10R-G109A), anti-KAT3A/CBP (Abcam ab2832), anti-SNAP25 (Abcam ab5666), anti-synaptophysin (Millipore MAB368), anti-MAP2 C/D (Cell Signaling 8707), anti-NR4A2 (Santa Cruz sc-991) and anti-NeuN (Millipore ABN78).

Intracranial Injection of Viral Vector

Adult mice (8+ weeks of age) were anaesthetized with isoflurane gas (1-5% to maintain surgical plane) and placed in a sterile field within a stereotaxic device. Animals received an injection of bupivacaine (2.5 mg/kg) for local anaesthesia before the skin was disinfected with betadine solution and the skull exposed with a short incision using sterile surgical equipment. Artificial tears were applied to eyes to ensure sufficient lubrication. A small hole (about 0.5 mm) was drilled in the skull over the target area using a stereotax and a stereotactic drill. A micro-syringe filled with viral vector was inserted into the dorsal hippocampus and slowly removed following injection (AP, −2.0 mm; DV, −1.4 mm; ML, +1.5 mm from bregma). ACSS2 knockdown vector, AAV2/9.U6.shACSS2.CMV.EGFP; eGFP control vector, AAV2/9.CMV.EGFP.polyA. All animals received a single dose of subcutaneous meloxicam (5 mg/kg) as analgesia at induction and one dose per day for two days postoperatively as needed.

Object Location Memory Task

The object location memory procedure is used to test spatial memory. The procedure consists of a training phase and a testing phase. Prior to training, each mouse was handled for 3 min a day for 3 days. On the training day, mice are placed in an arena (approx. 1 square foot) containing three different objects. The objects used were a glass bottle, a metal tower (h×w×l, 5×2×2 inches), and a plastic cylinder. Mice were habituated to an empty arena with a black and white striped spatial cue on the wall, followed by object exposure in three 6-min trials with an interval of 3 min. The arena and objects were cleaned with 70% EtOH between trials. To diminish biases, the memory test was performed on control and knockdown mice on the same day in the same arena, using every combination of object location (n=10 mice per study group). After 24 hours, the individual mice were placed back in the arena used in the testing phase. For testing, one of the objects was moved to different location in the arena. Mice were allowed to explore freely for 5 min. Each session was recorded using a video camera and time spent exploring (approaches and sniffing) each object was assessed offline. All animals were randomized and preassigned to arena and object the day before testing to ensure that every treatment group explored every object configuration.

Contextual Fear Conditioning

The mouse was placed in the conditioning chamber (Med Associates) for 5 min before the onset of the unconditioned stimulus (US), a 1.5-mA continuous foot shock. A mild 2-sec, 1.5-mA foot shock is used as an aversive stimulus; this does not injure the mice but provides the transient, yet startling and aversive, stimulus that is necessary for conditioning. After an additional 30 sec in the chamber, the mouse was returned to its home cage. Twenty-four hours later, the mouse was tested for a freezing response to the chamber (contextual) where training occurred. Time spent freezing in the chamber (motionless except for respiratory movements) was assessed for 5 consecutive minutes.

Data Availability

The ChIP-seq and RNA-seq data have been made available at the Gene Expression Omnibus (GEO) repository under the SuperSeries accession code GSE76854.

The results of the experiments are now described.

ACSS2 Regulates Neuronal Gene Expression

Figure 5:
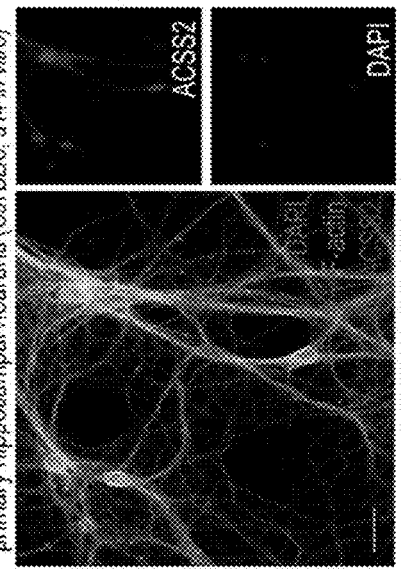
FIG. 5, comprising
Figure 5:
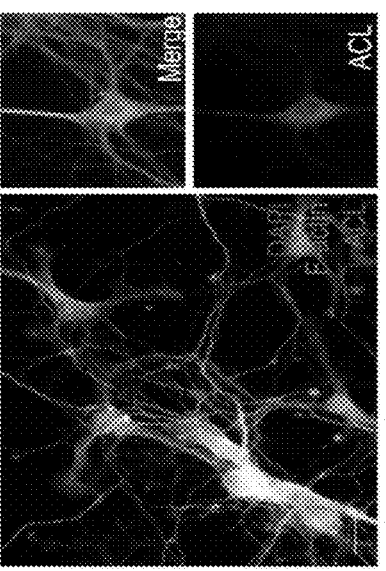
Figure 5:
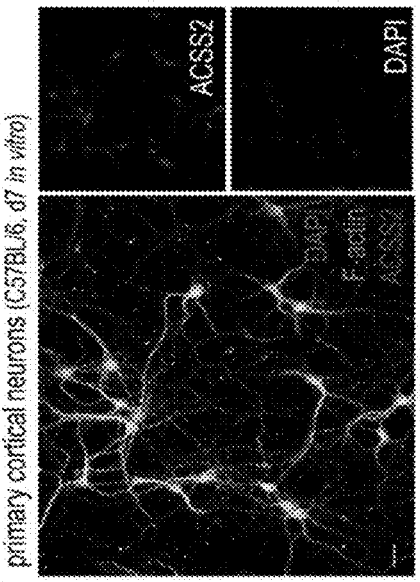
Figure 5:
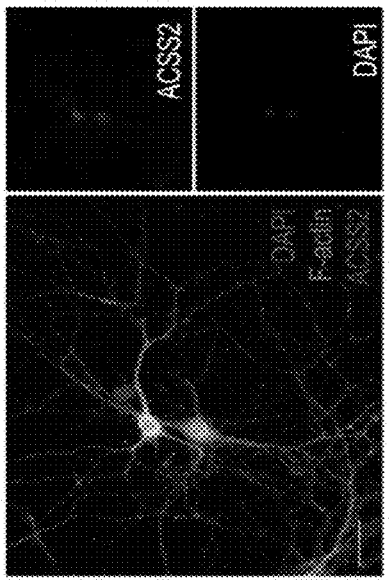
Figure 5:
Figure 5:
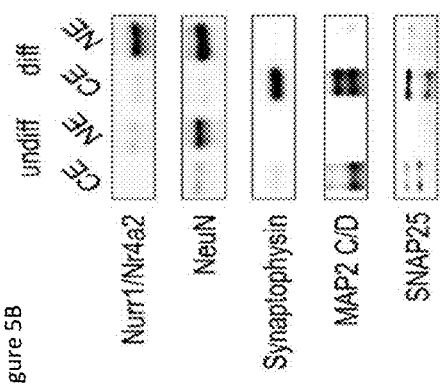
Figure 5:
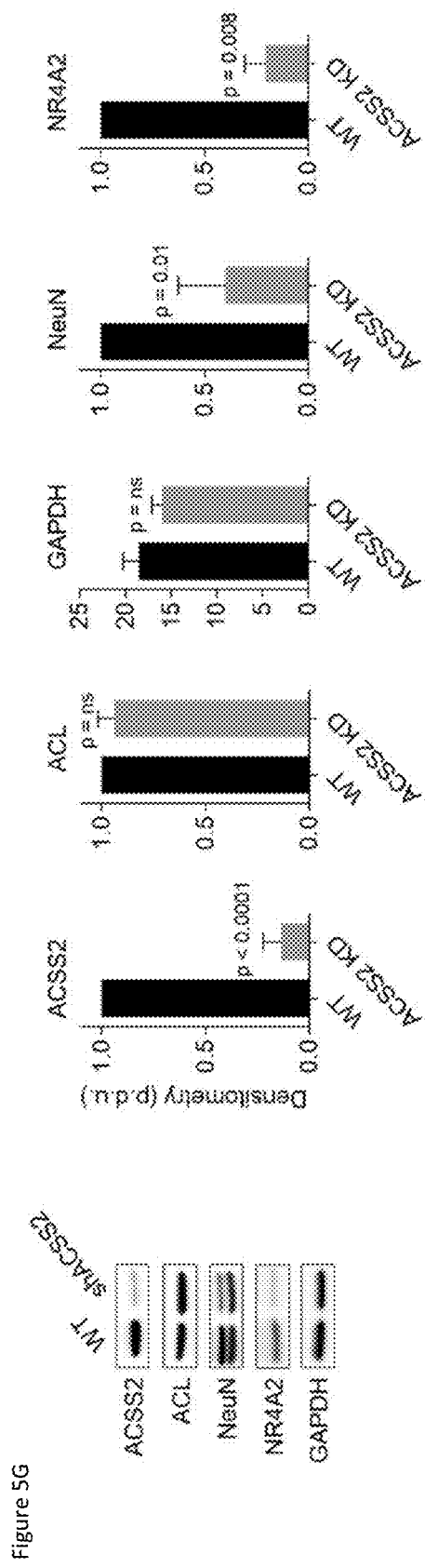

The function of ACSS2 in neurons was investigated using the Cath.-a-differentiated (CAD) cell line derived from mouse catecholaminergic cells. Upon serum deprivation, CAD cells differentiate to form neuronal processes and become excitable, similar to functional neurons (Qi, Y. et al., 1997, J. Neurosci., 17:1217-1225). Immunofluorescence showed that endogenous ACSS2 was primarily cytoplasmic in undifferentiated CAD cells (FIG. 1A), but shifted primarily to the nucleus upon differentiation (FIG. 1B, FIG. 5A). Whole-cell and nuclear levels of ACSS2 increased upon differentiation of CAD cells into neurons, whereas cytoplasmic ACL expression remained constant (FIG. 1C). In primary hippocampal and cortical neurons from mouse brain, even 14 days after isolation, ACSS2 was chiefly nuclear and ACL was primarily cytoplasmic (FIG. 5C, FIG. 5D, FIG. 5E, FIG. 5F). It was concluded that ACSS2, unlike ACL, is localized to nuclei during neuronal differentiation.

The role of ACSS2 in upregulation of canonical neuron-specific protein markers in differentiated CAD neurons was investigated. Pre-differentiation knockdown of ACSS2 reduced differentiation-linked expression of nuclear NeuN, activity-regulated Nr4a2, and the cytoplasmic markers synaptophysin, Map2 and Snap25, without an associated decrease in ACL (FIG. 5G), indicating that ACSS2 has a key role in neuronal differentiation.

Figure 7:
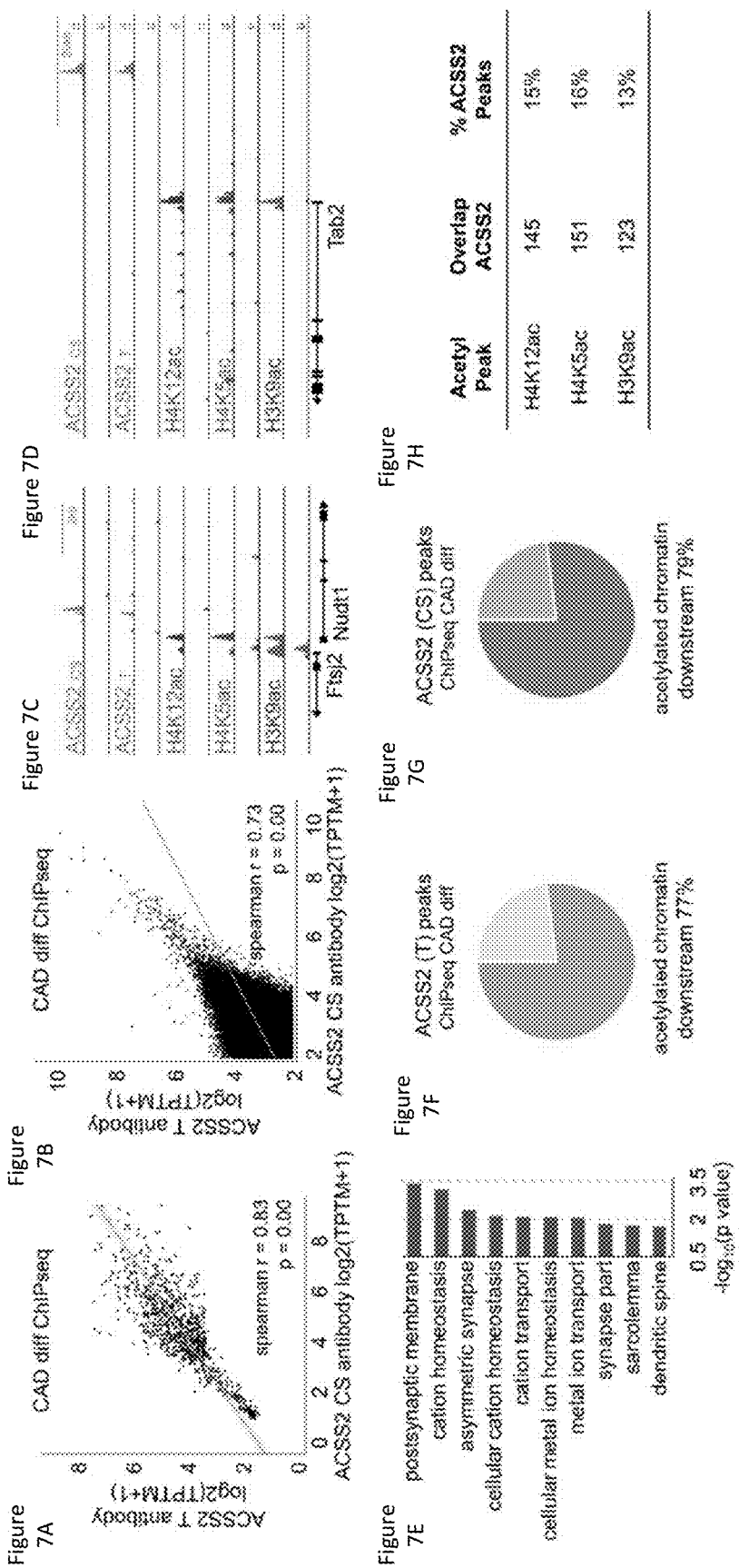
FIG. 7, comprising
Figure 7:
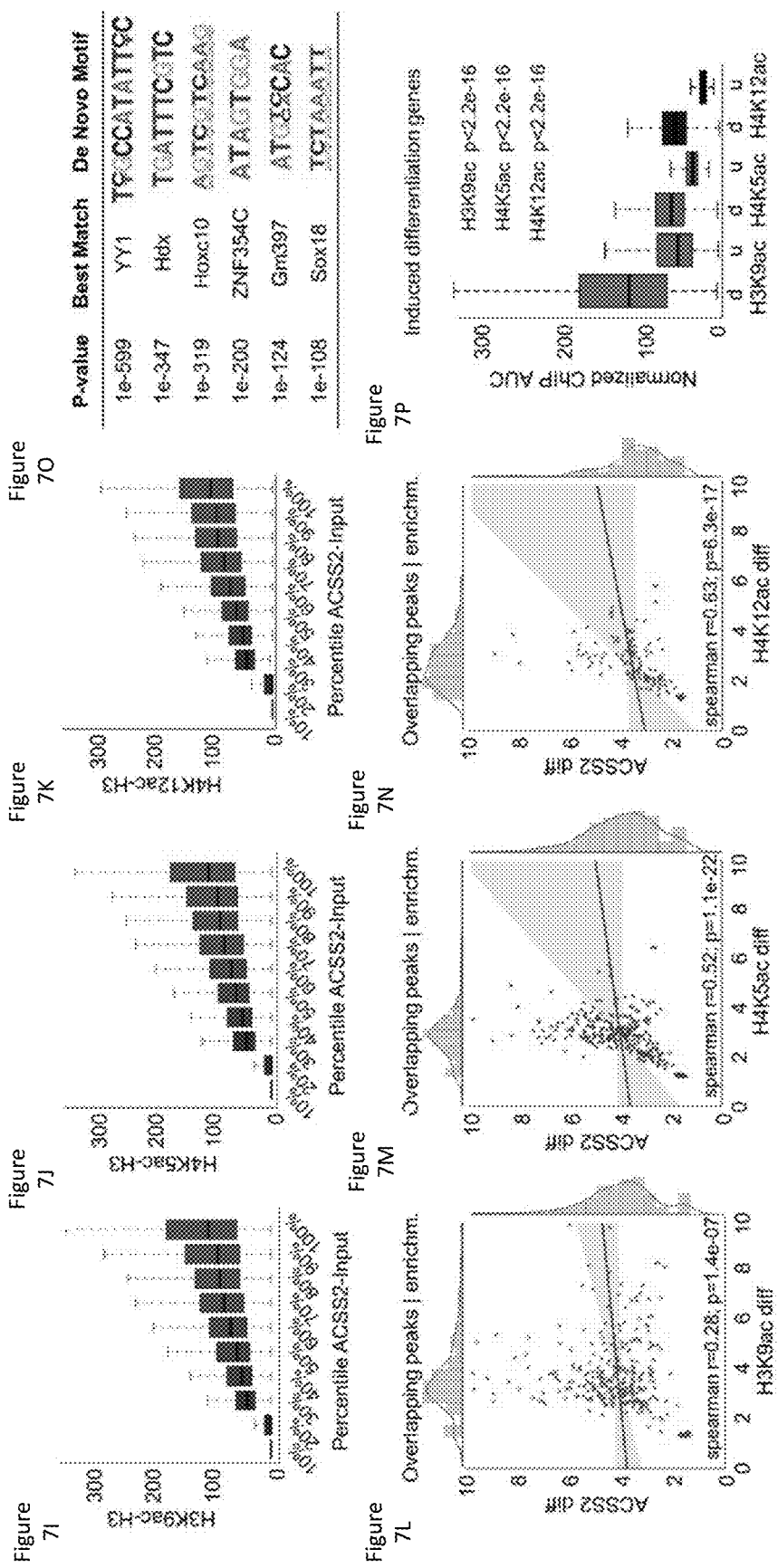

Transcriptome analysis by mRNA sequencing (mRNA-seq) upon CAD neuronal differentiation identified 894 upregulated genes (FIG. 7A, FIG. 7B, FIG. 7C; Table 1). Gene ontology analysis revealed that these differentiation-linked genes were neuron-specific; gene ontology terms included neuron differentiation, synaptic transmission, ion transport, and neuron projection morphogenesis (FIG. 7E). A protein interaction framework that produced a neuronal network centered on activity-dependent signaling and synaptic plasticity was developed: calmodulin 1 (Calm1), glutamate ionotropic receptor NMDA type subunit 1 (Grin1), and inositol 1,4,5-trisphosphate receptor type 1 (Itpr1) (FIG. 7D). Calm1 mediates the control of neuronal proteins by $Ca^{2+}$ during synaptic plasticity, including $Ca^{2+}$/calmodulin-dependent protein kinase II (CaMKII). Such $Ca^{2+}$ signaling is regulated by Grin1, an NMDA receptor subtype of glutamate-gated ion channels, and also by the ion channel Itpr1, which mobilizes intracellular $Ca^{2+}$ stores, an important process in activity-dependent signaling that underlies synaptic plasticity during learning.

TABLE 1

A list of genes upregulated 1.6-fold or higher upon CAD neuronal differentiation, corresponding to the top 10% of upregulated genes by fold-change diff vs undiff.

| Gene | Fold-change | Gene | Fold-change | Gene | Fold-change |
| --- | --- | --- | --- | --- | --- |
| Gm1821 | 175.6579238 | Cd3eap | 2.170133884 | Eme2 | 1.823970526 |
| Bc1 | 18.89222241 | B3galt6 | 2.169981093 | Abcb10 | 1.823927603 |
| Chgb | 17.14357199 | Pxylp1 | 2.166764625 | Coa3 | 1.822527659 |
| Gm15127 | 15.51766099 | Plxncl | 2.160531802 | Dnajb12 | 1.82210436 |
| Rnaset2b | 12.75361823 | Camk1d | 2.158710733 | Mad1l1 | 1.821858573 |
| Tcte3 | 9.952430312 | Myt1l | 2.155525888 | Nagpa | 1.821421835 |
| Slc7a14 | 8.513220194 | 2310040G24Rik | 2.154691887 | Bag5 | 1.820414157 |
| Syt4 | 7.711544335 | Nagk | 2.15371853 | Scg5 | 1.820055865 |
| Chga | 6.960140476 | Zfp646 | 2.153449442 | Cyb561d2 | 1.819353638 |
| Tcte3 | 6.787934727 | Clcn5 | 2.153194258 | Slc7a1 | 1.818877568 |
| St18 | 6.154430487 | D430020J02Rik | 2.152743565 | Dmrtc1c1 | 1.81721542 |
| Lrrn3 | 5.678039797 | Ptprr | 2.152060138 | Dusp16 | 1.816831604 |
| Nefh | 5.663029385 | Neurl3 | 2.151224453 | Tfpi | 1.815801097 |
| Sv2c | 5.604691346 | Rtn3 | 2.149814381 | Smarcad1 | 1.815095829 |
| St8sia3 | 5.516463854 | Coro2a | 2.148771712 | Kidins220 | 1.815049028 |
| Tfrc | 5.330857918 | Syne2 | 2.146800723 | Tex261 | 1.81297524 |
| C7 | 5.088574779 | Kcnq2 | 2.146167325 | Itga6 | 1.812508999 |
| Ina | 5.036193249 | Cd151 | 2.145739959 | Jph3 | 1.812352364 |
| 6030419C18Rik | 5.000233138 | Trmt5 | 2.145499 | Gm14139 | 1.810377573 |
| Lix1 | 4.924417409 | Opcml | 2.142896705 | Asphd1 | 1.810011841 |
| F2rl2 | 4.868341078 | Ptpn13 | 2.142246807 | Smarce1 | 1.807946088 |
| Bex2 | 4.733589022 | Vegfc | 2.140464179 | Rrp7a | 1.807062004 |
| Srp54b | 4.688634976 | Gm13154 | 2.140261646 | Myh3 | 1.806367241 |
| Chrna3 | 4.611736933 | Gm9833 | 2.140118183 | Lin28b | 1.805854386 |
| Bend7 | 4.585426322 | Tmem158 | 2.138968007 | Nup85 | 1.804665858 |
| Cplx1 | 4.444224944 | Fscn1 | 2.137050753 | Scrt1 | 1.803337363 |

TABLE 1-continued

A list of genes upregulated 1.6-fold or higher upon CAD neuronal differentiation, corresponding to the top 10% of upregulated genes by fold-change diff vs undiff.

| Gene | Fold-change | Gene | Fold-change | Gene | Fold-change |
|---|---|---|---|---|---|
| Scg2 | 4.356337617 | Rundc3a | 2.13434778 | Atf2 | 1.80172488 |
| Syp | 4.327573468 | Spint1 | 2.133736983 | Serpina1d | 1.801250346 |
| Itga1 | 4.278299803 | Gng4 | 2.129537408 | Dbn1 | 1.80099271 |
| Hmgb3 | 4.1862105 | Ms1312 | 2.128923538 | Ankrd49 | 1.80079943 |
| Gpr22 | 4.1674996 | Dnajc6 | 2.128248925 | Celf5 | 1.799789076 |
| Gm6644 | 4.106399081 | Arxes2 | 2.124711148 | Pam | 1.799761546 |
| Ngfrap1 | 4.090845268 | Hexim1 | 2.124625821 | Zbtb10 | 1.799707942 |
| 11-Mar | 4.082591127 | Cstf2 | 2.123424958 | Magea8 | 1.799361507 |
| Lrp11 | 4.046236641 | Apol10b | 2.123145491 | Kcnb1 | 1.798921382 |
| Syne1 | 3.991300602 | Garem | 2.121754047 | Agpat9 | 1.797386751 |
| Grb14 | 3.945690545 | Mmp24 | 2.116395802 | Dfna5 | 1.796745137 |
| Myb | 3.90824467 | Siah1b | 2.113360374 | Gnao1 | 1.795924972 |
| S1c26a4 | 3.870330962 | 9330182L06Rik | 2.113260274 | Onecut2 | 1.795915729 |
| Gap43 | 3.845523746 | Klf11 | 2.111304581 | Nop2 | 1.795704394 |
| Tubb3 | 3.839461152 | Nrxn2 | 2.108670556 | Cxx1c | 1.795202843 |
| Agtr1a | 3.787641152 | Ttyh3 | 2.106168371 | Tbkbp1 | 1.795132889 |
| Cobll1 | 3.776724233 | Tmem63c | 2.104274635 | Lamp1 | 1.793429305 |
| Manea1 | 3.74209634 | Ppfia2 | 2.104105162 | Uros | 1.792154061 |
| Ablim1 | 3.696297385 | Calm1 | 2.101694438 | Olfml3 | 1.791288679 |
| Pyg1 | 3.66431466 | Act16b | 2.100910703 | Immt | 1.79036382 |
| Ogfod3 | 3.623862166 | Stmn3 | 2.100007128 | N1rp4c | 1.789285052 |
| Zdbf2 | 3.595183027 | Efna5 | 2.098388029 | Tmod2 | 1.789055398 |
| Tcte3 | 3.563270202 | Rhbdd2 | 2.097503081 | Gsg2 | 1.788260344 |
| Zcchc12 | 3.555338395 | 5730409E04Rik | 2.096839768 | Brpf3 | 1.788146652 |
| Insm1 | 3.51414208 | A330076H08Rik | 2.09651456 | Psme3 | 1.787606977 |
| Rtl1 | 3.445197877 | Celf4 | 2.093422103 | B230217O12Rik | 1.787068322 |
| Bhlhb9 | 3.427368454 | Chst11 | 2.091694127 | Dhrs7b | 1.786833183 |
| Rpl26 | 3.403059425 | Trmt6 | 2.091481094 | Mfn2 | 1.786829419 |
| Fmn12 | 3.390037903 | Tle4 | 2.091242414 | Clu | 1.786603419 |
| Diras2 | 3.344496731 | Mid2 | 2.090168909 | Mdn1 | 1.784727192 |
| Syt7 | 3.305395031 | Lrif1 | 2.083927045 | Crlf1 | 1.782967462 |
| Nrp1 | 3.254754196 | Aplp2 | 2.080116197 | Dusp1 | 1.78268785 |
| Crmp1 | 3.252645244 | C1ql1 | 2.076261716 | Il23a | 1.782195797 |
| Trp53i11 | 3.241772978 | Ets2 | 2.076132879 | Zfp60 | 1.780426997 |
| Elfn2 | 3.238729769 | Gde1 | 2.07447251 | Mcts1 | 1.779483364 |
| Acyp2 | 3.234343027 | Mras | 2.074382859 | Shq1 | 1.779248886 |
| Snap91 | 3.230834555 | Nt5c2 | 2.073514495 | Grhl2 | 1.7791477 |
| Cpt1a | 3.229336895 | Acsl5 | 2.072620341 | Trappc2 | 1.778257911 |
| Gpatch4 | 3.222172569 | Chrm4 | 2.072223233 | Cd9 | 1.777982221 |
| Tceal8 | 3.217666679 | Rom1 | 2.07126501 | Ppp2r3d | 1.777014646 |
| Bex1 | 3.188074487 | Kcnn2 | 2.068794964 | 3300005D01Rik | 1.776683404 |
| 4933432K03Rik | 3.183007869 | Dusp22 | 2.0667913 | Trappc21 | 1.775573052 |
| Ubxn8 | 3.180294016 | Serinc1 | 2.065964409 | Atp6v1h | 1.774994978 |
| Nme1 | 3.179596125 | Grin1 | 2.063481712 | BC005624 | 1.774906486 |
| Gm3448 | 3.176047756 | Ccdc40 | 2.061884422 | Nipa2 | 1.773384434 |
| Eid2 | 3.163737628 | Imp4 | 2.059494693 | Armcx4 | 1.772224038 |
| Rgs7 | 3.140441667 | Sync | 2.058561575 | Sptbn1 | 1.771756217 |
| Sez6l2 | 3.138031104 | Itpr1 | 2.058179448 | Acs16 | 1.771288672 |
| Nudt1 | 3.131824273 | Dlg2 | 2.057014709 | Exoc8 | 1.770448693 |
| Ttc8 | 3.127218279 | Laptm4a | 2.055520048 | Tmx2 | 1.770238878 |
| Ccdc64 | 3.113624626 | Tmx4 | 2.054452 | Apmap | 1.769567355 |
| Soga3 | 3.106573768 | Ccdc711 | 2.053367712 | Dpcd | 1.76832124 |
| Dynlt1f | 3.075927839 | Tex13 | 2.052406599 | Lactb | 1.767193082 |
| Kcnab1 | 3.075671599 | Ccdc106 | 2.049420856 | BC048403 | 1.766450957 |
| Myt1 | 3.070224982 | Ofd1 | 2.049383373 | Mcm10 | 1.766240198 |
| Rpp25 | 3.069442261 | Atrnl1 | 2.048809708 | Hipk3 | 1.766048616 |
| Capn6 | 3.06860951 | Fbxl16 | 2.047921237 | Gnaz | 1.765435041 |
| Rps6ka6 | 3.051147613 | Mia2 | 2.04777355 | Tnik | 1.765229777 |
| Moap1 | 3.050801905 | Hs3st2 | 2.047395008 | Ywhah | 1.765199109 |
| Sult4a1 | 3.050032271 | Scamp5 | 2.04672811 | Gm4944 | 1.764668491 |
| Thsd7a | 3.042155585 | Cd248 | 2.042574215 | Pik3r1 | 1.764390036 |
| Syt1 | 3.035831847 | Myo1b | 2.042361194 | Mcm2 | 1.763793482 |
| Dppa2 | 3.025823893 | Kbtbd8 | 2.039844229 | Pgbd5 | 1.763785993 |
| Sobp | 3.016460969 | Dscaml1 | 2.035957043 | Ahnak | 1.762687909 |
| Glcci1 | 3.005342056 | Arsb | 2.034675917 | Tubg1 | 1.762408455 |
| Lin28a | 2.983923999 | Glipr1 | 2.027994233 | Upf3b | 1.761898167 |
| Usp51 | 2.975360783 | Smarcc1 | 2.026414744 | Vav2 | 1.761024602 |
| Enol1 | 2.97263557 | Dscc1 | 2.026254958 | Cmpk2 | 1.760528848 |
| Ubqln2 | 2.956614456 | Atp6v1c1 | 2.024670168 | Flrt3 | 1.759648874 |
| Arrdc3 | 2.955284729 | Tub | 2.024311372 | 2900009J06Rik | 1.7594006 |
| Isg15 | 2.933241785 | Ctxn1 | 2.021976572 | Apon | 1.758839365 |
| Pde4dip | 2.906021486 | Nudc | 2.021960351 | A330040F15Rik | 1.756818568 |
| Shisa3 | 2.881691875 | Eif3b | 2.020017253 | Dpysl3 | 1.756580466 |
| Dync1h1 | 2.873386193 | Napb | 2.017401664 | Wdr6 | 1.756565798 |

TABLE 1-continued

A list of genes upregulated 1.6-fold or higher upon CAD neuronal differentiation,
corresponding to the top 10% of upregulated genes by fold-change diff vs undiff.

| Gene | Fold-change | Gene | Fold-change | Gene | Fold-change |
|---|---|---|---|---|---|
| Cpeb2 | 2.854892675 | Cdc6 | 2.016230466 | Zfp345 | 1.756041804 |
| Syt6 | 2.84753409 | Gprasp1 | 2.015850089 | Gm5801 | 1.755666178 |
| Clvs1 | 2.822978842 | Nfasc | 2.015721892 | Vipas39 | 1.755094357 |
| Kcnk3 | 2.817797535 | Nxf3 | 2.014974572 | Pih1d2 | 1.753692794 |
| Gm5868 | 2.812232401 | Zhx1 | 2.012540964 | Abcc3 | 1.752792921 |
| Arxes1 | 2.811860001 | B3galt1 | 2.010886035 | Mki67 | 1.751856644 |
| Stox2 | 2.780799101 | Gba | 2.006904267 | 5033406O09Rik | 1.751135413 |
| Nmnat2 | 2.779691083 | Mafb | 2.005616568 | Sema6d | 1.750218169 |
| Basp1 | 2.776507236 | Icam2 | 2.005565245 | Mapkap1 | 1.748722597 |
| Nxt2 | 2.765596658 | Csrnp3 | 2.004149481 | Rmdn3 | 1.748669909 |
| Slco3a1 | 2.761274885 | G530011O06Rik | 2.003834543 | Fut11 | 1.747886156 |
| 9330159F19Rik | 2.759766806 | Ispd | 2.00357033 | Rufy3 | 1.747069267 |
| Bscl2 | 2.752674021 | Trmt61a | 1.999997328 | Fam21 | 1.746467678 |
| Zbtb1 | 2.750343915 | Ccpg1 | 1.998744702 | Angptl7 | 1.74568611 |
| Slc25a20 | 2.732767312 | Sox11 | 1.997046172 | Ptgr2 | 1.744488542 |
| Lrr1 | 2.724323049 | Upf3a | 1.992047853 | Parp8 | 1.741931597 |
| H2afy2 | 2.714935834 | Dst | 1.991416813 | Rims4 | 1.74001918 |
| Ccdc101 | 2.688893985 | Slc35g2 | 1.991032922 | Mex3b | 1.739919034 |
| Prps2 | 2.688066633 | Dusp10 | 1.990296185 | Hmha1 | 1.739634453 |
| Slit2 | 2.680804093 | Zfp672 | 1.989832275 | Sh3kbp1 | 1.739580052 |
| Fam73a | 2.680489857 | Tmem56 | 1.98880423 | Cbll1 | 1.738638987 |
| Spock2 | 2.668728711 | Xkr5 | 1.988679099 | Tspan14 | 1.738560062 |
| Id4 | 2.663294856 | Chrnb2 | 1.988324031 | Fam136a | 1.736003183 |
| Elavl3 | 2.661848056 | Alg2 | 1.984414687 | Ampd3 | 1.735262497 |
| Gprin1 | 2.659163353 | Abcb6 | 1.979958221 | Cdk5r2 | 1.733761696 |
| Zfp941 | 2.653595168 | Arpp21 | 1.979082597 | Phox2b | 1.7326033 |
| Arhgef28 | 2.652052288 | Eml6 | 1.97800923 | Utp20 | 1.732574299 |
| Pcdhac2 | 2.645536483 | Pvrl1 | 1.977863127 | Pigt | 1.732092573 |
| Cited2 | 2.635020506 | Ccne2 | 1.976366942 | Rab11b | 1.73169755 |
| Gabrb3 | 2.630267867 | Hist2h3c1 | 1.975040976 | Bdh1 | 1.731670577 |
| Mmd | 2.630198806 | Hist2h3c1 | 1.975040506 | Lrrc2 | 1.731121108 |
| Trpc7 | 2.62761764 | Hist2h3c1 | 1.97439534 | Mettl24 | 1.730670243 |
| Tmem164 | 2.622650194 | Hist2h3c1 | 1.974394871 | 9130023H24Rik | 1.730622105 |
| Astn1 | 2.619175631 | Pelo | 1.973649509 | Slc35f3 | 1.730212207 |
| Lmo2 | 2.613888268 | Pmpca | 1.971199074 | Cyb5r4 | 1.728975276 |
| Kpnb1 | 2.612082447 | D14Ertd670e | 1.966194908 | 4933409K07Rik | 1.728946459 |
| Ywhag | 2.611362467 | Acap3 | 1.964633963 | Fbll1 | 1.728705387 |
| Pcdha9 | 2.609047858 | Naa40 | 1.96318494 | Iba57 | 1.728152072 |
| 4930412O13Rik | 2.59954161 | Odc1 | 1.962296385 | Abhd16a | 1.724790788 |
| Sez6 | 2.594545132 | Nsf | 1.962079336 | C230052I12Rik | 1.724519072 |
| Mthfd1 | 2.594534783 | Ric3 | 1.957504324 | Cep290 | 1.723738934 |
| Cygb | 2.594202918 | Cyb561 | 1.956983455 | Disp2 | 1.721375855 |
| Mapk8ip2 | 2.586130338 | Prpf31 | 1.950424024 | Ccdc86 | 1.7206313 |
| Rims2 | 2.582500994 | Atp1a3 | 1.949704023 | Slc24a2 | 1.718144872 |
| Zfp105 | 2.57834921 | Asic1 | 1.949220769 | Naaa | 1.716002932 |
| Rab3c | 2.56905558 | Prkar2a | 1.947217244 | Myef2 | 1.71556509 |
| Tcerg1l | 2.560508109 | Gm10516 | 1.94574251 | Marcksl1 | 1.714941564 |
| Lgr5 | 2.559906391 | Gdap1l1 | 1.945511639 | As1 | 1.712968358 |
| Ank2 | 2.557088209 | Shisa4 | 1.944591761 | Pmm2 | 1.712746409 |
| AA414768 | 2.556426952 | Jph1 | 1.943999212 | Rtn4rl1 | 1.712680069 |
| Fen1 | 2.552951046 | 2410076I21Rik | 1.942669169 | Rltpr | 1.712475563 |
| Atp2b3 | 2.552525124 | Zfhx4 | 1.942750871 | Rbm3 | 1.711669169 |
| Plxcd3 | 2.547915161 | B230216N24Rik | 1.942106125 | Ccdc137 | 1.711399973 |
| Map1b | 2.546432223 | Pomt2 | 1.941883342 | Tubb2a | 1.710451318 |
| Cnga3 | 2.54463692 | Ak1 | 1.940188779 | Cers6 | 1.71012081 |
| Prima1 | 2.540015798 | Hmgn2 | 1.939312621 | Rc3h2 | 1.70930883 |
| Tceal1 | 2.536928591 | Crb2 | 1.938608613 | Wfikkn2 | 1.709206434 |
| Ptprn | 2.530300281 | Sncb | 1.938186969 | D6Wsu163e | 1.708994488 |
| Gm14124 | 2.528627525 | Mcm7 | 1.938141062 | Fam171a2 | 1.708684719 |
| Nsg1 | 2.527832329 | Nav3 | 1.937091743 | Slc8a3 | 1.708154517 |
| Peg13 | 2.526460165 | Celsr3 | 1.937008133 | Tubb2b | 1.707297903 |
| Chrna7 | 2.521656827 | Nomo1 | 1.936027801 | Psmc1 | 1.706891691 |
| Frmpd1 | 2.513212694 | Ppip5k2 | 1.935223601 | Chd4 | 1.706378216 |
| Scg3 | 2.507811675 | Fads6 | 1.934377481 | Zdhhc24 | 1.7057495 |
| Map7d2 | 2.497575084 | Zdhhc2 | 1.933684461 | Kifap3 | 1.705719758 |
| Cltb | 2.497372532 | Prep | 1.932286093 | Cadm1 | 1.705546607 |
| Podxl | 2.496009524 | Pfdn2 | 1.929900656 | Fdxacb1 | 1.705207276 |
| Gpr68 | 2.495164795 | Aox4 | 1.927911942 | Dcun1d2 | 1.704817808 |
| Syn1 | 2.492408986 | 2010320M18Rik | 1.926539948 | Gpr19 | 1.704379411 |
| Peg3os | 2.485925677 | Rrp12 | 1.926113939 | Atl1 | 1.704121204 |
| Stac | 2.485547115 | Tnfsf13b | 1.92507446 | Zfp37 | 1.702563195 |
| 1700008J07Rik | 2.484043438 | Pdss1 | 1.922389127 | Galc | 1.70230816 |
| Tmtc1 | 2.482449248 | Ddx25 | 1.92174518 | Klh17 | 1.701799864 |
| Akap12 | 2.481981855 | | | Coro1c | 1.701663394 |

TABLE 1-continued

A list of genes upregulated 1.6-fold or higher upon CAD neuronal differentiation, corresponding to the top 10% of upregulated genes by fold-change diff vs undiff.

Figure 4:
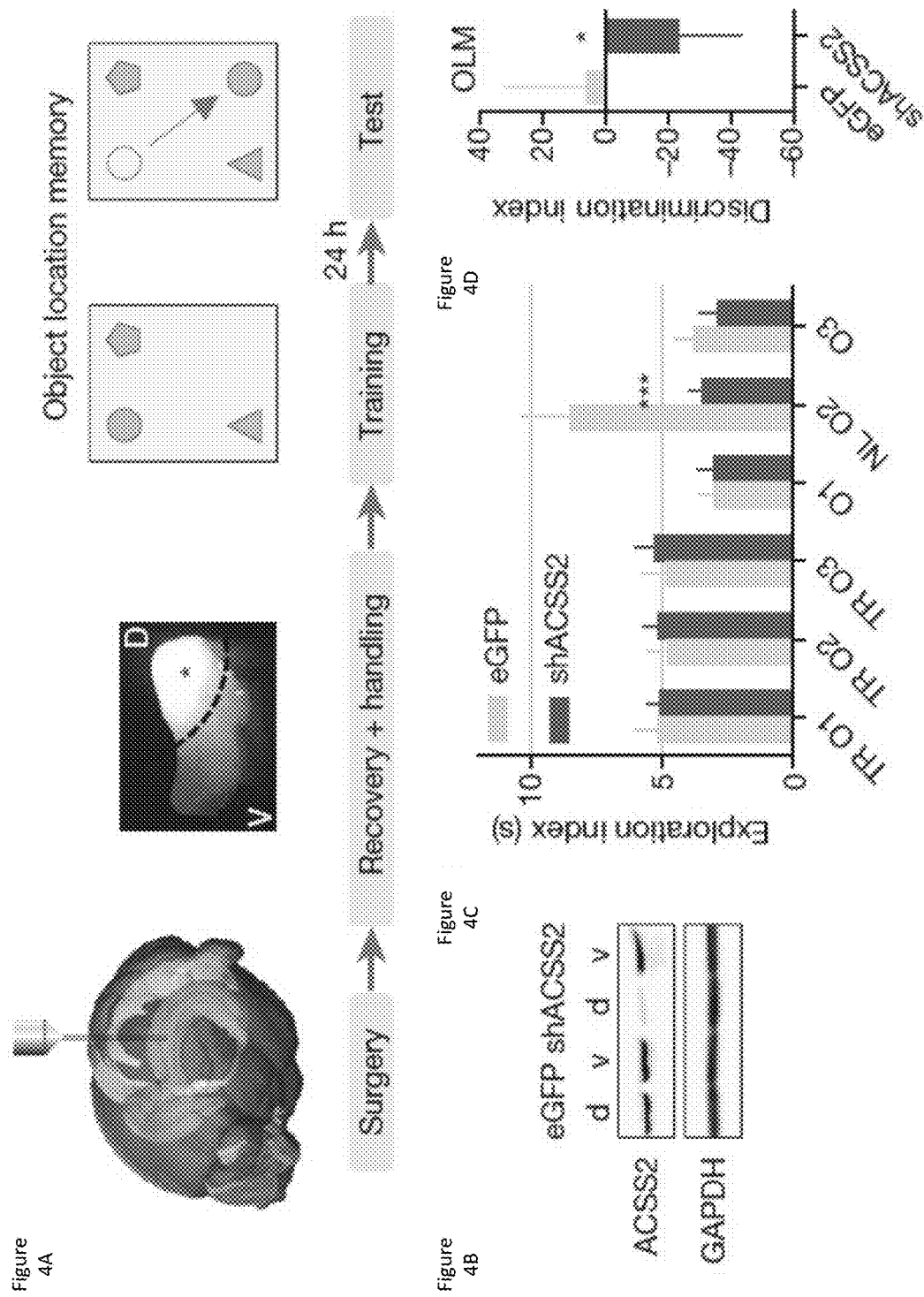
FIG. 4, comprising
Figure 4:
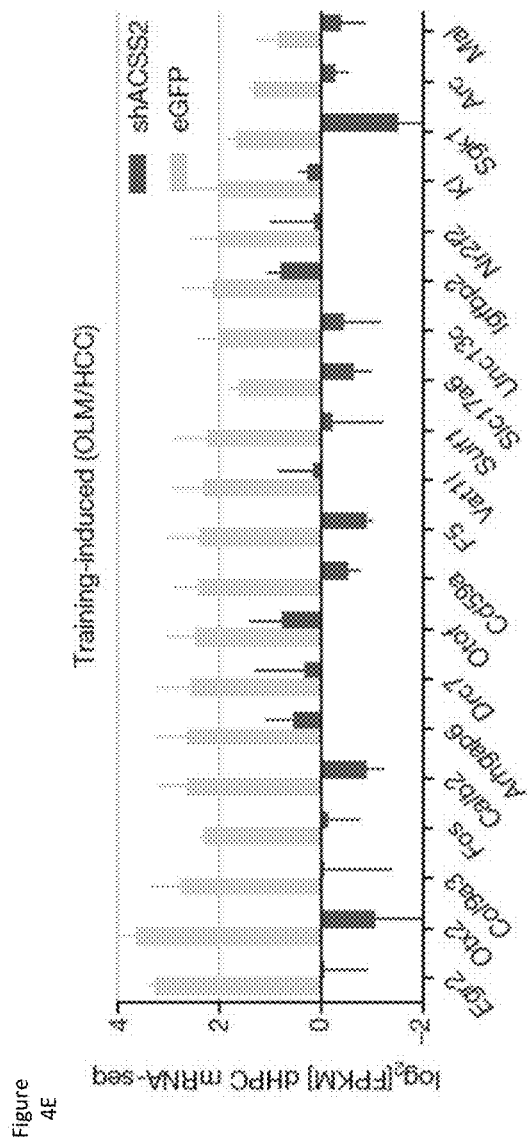
Figure 4:
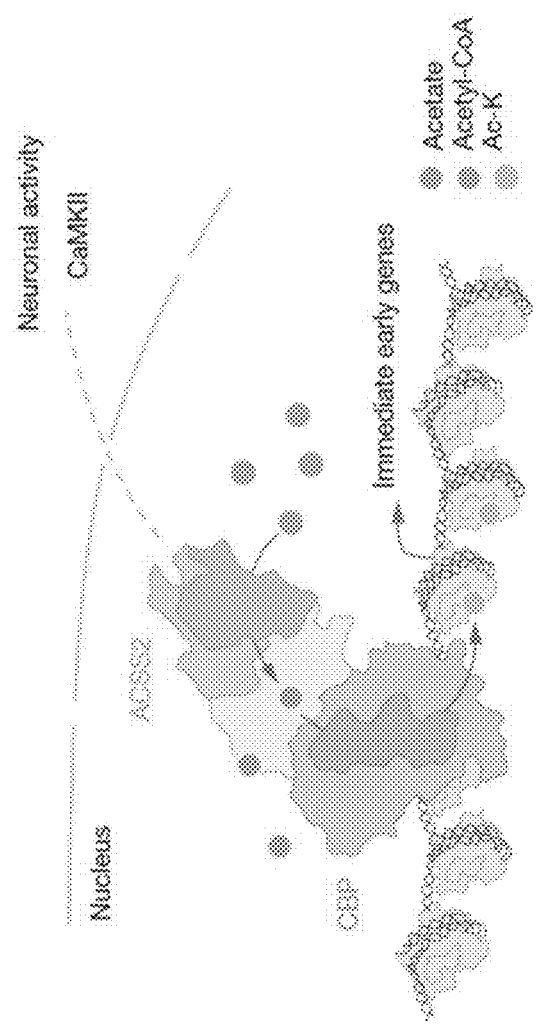

| Gene | Fold-change | Gene | Fold-change | Gene | Fold-change |
|---|---|---|---|---|---|
| Gm13889 | 2.473754193 | Ppat | 1.920879419 | N4bp2 | 1.70137242 |
| Aig1 | 2.471662617 | Rad51 | 1.920722212 | Cyth3 | 1.700454504 |
| Nap1l5 | 2.469349003 | A430035B10Rik | 1.920377197 | Gria2 | 1.699598134 |
| Ptprn2 | 2.467641397 | Rimkla | 1.920131006 | Rnf103 | 1.699576595 |
| Il1b | 2.467520516 | Fkrp | 1.918435117 | Rybp | 1.699136669 |
| Fstl4 | 2.461319176 | Gng2 | 1.914720195 | Mgat2 | 1.698388185 |
| Gdap1 | 2.459324502 | Zbtb6 | 1.913889619 | Cacng3 | 1.698216152 |
| Hist1h2bc | 2.458592095 | Cacna1b | 1.91297449 | Pou4f2 | 1.698190252 |
| Rgs4 | 2.456820051 | Sfxn1 | 1.912605475 | Slc25a16 | 1.697489578 |
| Rtn2 | 2.456045107 | Ddx24 | 1.910286019 | Tmem5 | 1.697359997 |
| Qsox2 | 2.443479002 | Dapk1 | 1.909272865 | Ankrd45 | 1.69578789 |
| Slc10a4 | 2.443317686 | Mfsd1 | 1.90858969 | Med1 | 1.695016446 |
| Npc1 | 2.442844829 | Kcnma1 | 1.906252243 | Scn3a | 1.693976545 |
| Psmc5 | 2.43852755 | Gnl3l | 1.905404777 | Knop1 | 1.693141571 |
| Spire2 | 2.43817828 | Dapp1 | 1.905280655 | Letm2 | 1.692996703 |
| Ppp2r2b | 2.436623889 | Fig4 | 1.904074862 | Pcna | 1.692987099 |
| Rab27a | 2.431185467 | Akr1c13 | 1.903698431 | Srm | 1.692546245 |
| Tcte3 | 2.430285346 | Eef1a2 | 1.902891155 | H3f3b | 1.692540018 |
| Unc79 | 2.42896397 | Epb4.1l3 | 1.902831138 | Rhov | 1.692258256 |
| Rere | 2.420946998 | Ovca2 | 1.901183855 | Cinp | 1.692148625 |
| Nkrf | 2.418071053 | Ssh2 | 1.900453866 | Nek3 | 1.690663139 |
| Tshz2 | 2.41642778 | Prnp | 1.899301236 | Nol9 | 1.690524211 |
| Lhfpl4 | 2.410185371 | Mrps2 | 1.899212746 | Gm8801 | 1.690275316 |
| Isl1 | 2.409248695 | Tmtc4 | 1.898938507 | Setbp1 | 1.690128797 |
| Srrm3 | 2.403958838 | Taf3 | 1.897880465 | Mtss1 | 1.689835118 |
| Slc29a4 | 2.396866695 | Ddx6 | 1.897322975 | Champ1 | 1.689414384 |
| Hsp90aa1 | 2.394800411 | Bex4 | 1.896950555 | Secisbp2 | 1.688464915 |
| Galnt3 | 2.387693032 | Rpp38 | 1.896133169 | Fus | 1.687897894 |
| Fam46a | 2.386772798 | Mmp15 | 1.896113253 | Zfp936 | 1.687393579 |
| Akap6 | 2.385151202 | Dnajb9 | 1.896089418 | Umps | 1.687287148 |
| Unc5a | 2.385077118 | 6430548M08Rik | 1.893669196 | Erlin2 | 1.686403998 |
| Spa17 | 2.381932467 | Gusb | 1.893273972 | Ncs1 | 1.68635252 |
| Armcx1 | 2.381036751 | Ptprj | 1.892506369 | Trim67 | 1.685742571 |
| Rundc3b | 2.377774829 | Tro | 1.890403492 | Ckmt1 | 1.685073896 |
| Kif5c | 2.374822358 | Nos1 | 1.889456863 | Arhgap39 | 1.684943724 |
| Polr1a | 2.37006057 | Ulbp1 | 1.889367146 | Syn2 | 1.684313334 |
| Dhrs4 | 2.365368437 | Atp11c | 1.888641934 | Zdhhc6 | 1.683756464 |
| Smarca2 | 2.365086661 | H60b | 1.886035789 | Morc2a | 1.683594931 |
| Sdc3 | 2.364573718 | Lrrc4b | 1.885291767 | 5830444B04Rik | 1.683180352 |
| Impact | 2.358940049 | Runx3 | 1.885204635 | Nol10 | 1.683138348 |
| Syt14 | 2.3576276 | Tmed1 | 1.884337236 | Cacng4 | 1.683101168 |
| Akr1c12 | 2.35170279 | Cpsf2 | 1.883974673 | Dnajc7 | 1.682611037 |
| Rsph1 | 2.351486036 | Tmem57 | 1.882975491 | Pdzd2 | 1.682587463 |
| Pmp22 | 2.350035976 | 2310033P09Rik | 1.882250099 | Pak6 | 1.682545384 |
| Wbp5 | 2.346786732 | Rabl2 | 1.882158882 | Ptplad1 | 1.679458325 |
| Prkca | 2.344303821 | Pitpna | 1.881932453 | Lipo1 | 1.679354818 |
| Rnf113a2 | 2.34299707 | Cdc123 | 1.881701502 | Clcn4-2 | 1.679179827 |
| Rtn4 | 2.341355269 | Psmd1 | 1.881543038 | 2210014F16Rik | 1.678795515 |
| Dusp3 | 2.336914633 | Gpatch3 | 1.881016859 | Fgd6 | 1.677856945 |
| Vgf | 2.333281785 | Gabarapl1 | 1.879939416 | Bend3 | 1.676649255 |
| Pja1 | 2.332545789 | Lhfpl5 | 1.878997447 | Pomgnt2 | 1.676509151 |
| Lrch2 | 2.327787274 | Zfp386 | 1.87838411 | Stk32c | 1.676286848 |
| Xkr7 | 2.323195789 | Ppp1r13b | 1.877446456 | Kif3b | 1.675950473 |
| Msrb2 | 2.321774461 | Akap1 | 1.876716578 | Tug1 | 1.675280054 |
| Resp18 | 2.320094281 | Clec21 | 1.876692332 | Dcakd | 1.675043345 |
| Ftsj3 | 2.319925457 | Fam3c | 1.87512747 | Hnrnpu | 1.674090524 |
| Rrm2 | 2.318816915 | Gla | 1.874879429 | 6530402F18Rik | 1.673841373 |
| 3-Sep | 2.317901491 | Fancm | 1.872317503 | AI507597 | 1.67311856 |
| Dusp26 | 2.315217495 | Isoc1 | 1.87105305 | Lrrc3 | 1.673042164 |
| Atp6v0a1 | 2.314441552 | Palld | 1.870884616 | Osbpl10 | 1.673029921 |
| Mfsd11 | 2.306371316 | Jph4 | 1.869670861 | 6330409D20Rik | 1.672704362 |
| Sstr2 | 2.305792842 | Cnrip1 | 1.869633707 | Fam222a | 1.672294928 |
| Grip1 | 2.303010673 | Dars | 1.868613783 | 4930474H20Rik | 1.671611988 |
| Hnrnph2 | 2.301444559 | Ddx21 | 1.867198424 | Mast1 | 1.671433547 |
| Nipal2 | 2.298812802 | Hcn4 | 1.865788038 | Trp53bp1 | 1.671138201 |
| Ston2 | 2.295055047 | Fam43a | 1.864011078 | Baz2b | 1.67075683 |
| Vps53 | 2.289633653 | Vwa5b1 | 1.863969349 | Gm1140 | 1.669835745 |
| Gipc2 | 2.289236832 | Arhgdig | 1.862404417 | Dcaf5 | 1.669626713 |
| Lhx5 | 2.287726502 | Trmt2b | 1.862269161 | Iscu | 1.669593253 |
| Dclk1 | 2.284738254 | Meis3 | 1.861831561 | Thumpd1 | 1.669127846 |
| Snap25 | 2.282197664 | Gemin6 | 1.861333656 | Fam171a1 | 1.668887754 |
| Bcap29 | 2.282122018 | Gm5512 | 1.861333198 | Tmed10 | 1.668819621 |
| Syt11 | 2.281088449 | Ppp1r10 | 1.861029556 | Pi4ka | 1.66870687 |
| Tanc2 | 2.278569711 | Sox4 | 1.86083136 | Ccar1 | 1.668501964 |

TABLE 1-continued

A list of genes upregulated 1.6-fold or higher upon CAD neuronal differentiation, corresponding to the top 10% of upregulated genes by fold-change diff vs undiff.

| Gene | Fold-change | Gene | Fold-change | Gene | Fold-change |
|---|---|---|---|---|---|
| Prkar1b | 2.277882216 | Rnf149 | 1.859016185 | Usp31 | 1.668019551 |
| Ttll7 | 2.276918784 | Gm10451 | 1.858282261 | D3Ertd751e | 1.667496489 |
| Ppp2r2c | 2.276658072 | Stmn4 | 1.856774327 | Pdap1 | 1.667488844 |
| Armcx2 | 2.268644676 | Unc13a | 1.85671842 | Leo1 | 1.667471581 |
| Wdr35 | 2.265314142 | Aven | 1.853946127 | Dut | 1.666931066 |
| Lgals3bp | 2.265115028 | Stau2 | 1.85156307 | Slc39a6 | 1.665602627 |
| Eif4e3 | 2.264987807 | Gamt | 1.851189856 | Grwd1 | 1.665476983 |
| Map2 | 2.264668982 | 1700052K11Rik | 1.850918723 | Bop1 | 1.665146841 |
| Rgl1 | 2.264094249 | Wasf1 | 1.85029807 | Baz1a | 1.664496169 |
| Tmx1 | 2.260736628 | Klc1 | 1.84994572 | Ncapg2 | 1.664133825 |
| Rhox5 | 2.260459126 | Mapt | 1.849853184 | Ptpn1 | 1.663963745 |
| 2010204K13Rik | 2.256574437 | Sdc1 | 1.849803409 | Dhx9 | 1.661797652 |
| Hcn2 | 2.253035203 | Zfp428 | 1.849336547 | A330050F15Rik | 1.661663284 |
| Gm7120 | 2.249641702 | Pigw | 1.848547815 | Tmem131 | 1.661052736 |
| Dynll2 | 2.247730864 | Garnl3 | 1.848497313 | Exosc9 | 1.661033821 |
| Nrip1 | 2.236297154 | Mrpl20 | 1.846810463 | Agfg1 | 1.661002122 |
| Panx1 | 2.235271455 | Smarca4 | 1.846436526 | Ahsa1 | 1.660962974 |
| Slc16a6 | 2.233992923 | Efhc2 | 1.846083405 | Lgmn | 1.660328735 |
| Mt3 | 2.2331597 | Pcdhgb1 | 1.845930958 | Pacsin1 | 1.660310806 |
| Celf3 | 2.233013864 | Mycbpap | 1.845365822 | Gm6787 | 1.659350326 |
| Dnajc11 | 2.219751251 | Wdfy3 | 1.845013089 | Gstm7 | 1.658970823 |
| Pkia | 2.219406778 | Nceh1 | 1.84493714 | Fmnl1 | 1.658654117 |
| Commd9 | 2.219393748 | Fam134b | 1.844817405 | Rnf112 | 1.657680566 |
| 4930526I15Rik | 2.218644904 | Pstpip1 | 1.844427603 | Ptcd3 | 1.657152744 |
| Se1l3 | 2.217920637 | Elavl4 | 1.843902306 | Hhex | 1.656754506 |
| 4930550L24Rik | 2.210086462 | Tuba8 | 1.843254105 | Ufm1 | 1.656676294 |
| Foxp1 | 2.208954244 | Rapgef2 | 1.842648206 | Smarcd1 | 1.656415594 |
| LOC100503496 | 2.208155647 | Mcm6 | 1.842531069 | Dyrk3 | 1.656199454 |
| Fam111a | 2.206805703 | Dmrtc1c2 | 1.842393283 | Bid | 1.656100175 |
| Tmie | 2.205900235 | Sgsh | 1.842238312 | Dync2li1 | 1.656027888 |
| Unc80 | 2.203512779 | Dph6 | 1.84038813 | Zfp11 | 1.654777396 |
| Tha1 | 2.19982455 | Meis2 | 1.839755932 | Smoc1 | 1.654537223 |
| Prps1l3 | 2.199715007 | 0610040B10Rik | 1.839304618 | Nfe2l2 | 1.654021972 |
| Stmn2 | 2.199601839 | Mllt11 | 1.838902842 | Atl3 | 1.652987408 |
| Ap4s1 | 2.198216557 | Pnmal1 | 1.838598117 | Ubl3 | 1.652814032 |
| Smpd3 | 2.197857241 | BC039966 | 1.836049546 | Tmem33 | 1.651936589 |
| Smarca1 | 2.197803474 | Nin | 1.83534734 | Slc4a3 | 1.651755144 |
| Tspan7 | 2.196692952 | Tmem74 | 1.834876695 | Tenm3 | 1.650505091 |
| Pctp | 2.195340118 | Ccdc92 | 1.833747074 | Ap1s2 | 1.650381217 |
| Mapk10 | 2.193496445 | Plxna4 | 1.832242996 | Vma21 | 1.650080813 |
| Ap3b2 | 2.189548862 | Nkain1 | 1.82998511 | Fbxl19 | 1.648861973 |
| Gpm6b | 2.188414017 | Timm8a1 | 1.82935184 | Hist3h2a | 1.648031868 |
| Sumf1 | 2.184806171 | Srrm4 | 1.828687427 | Gm15663 | 1.647544686 |
| Kif1b | 2.181037857 | Atp6v0d1 | 1.828497312 | Apbb1 | 1.64735093 |
| Tmem42 | 2.179489111 | Ube4a | 1.828181709 | Psmc3 | 1.647297037 |
| Apex1 | 2.175711582 | Eif4g2 | 1.828117898 | Naip2 | 1.646832206 |
| Mblac2 | 2.174911584 | Coq7 | 1.827888701 | Fbxo47 | 1.646673454 |
| Cask | 2.173206274 | Tusc3 | 1.826480198 | Gemin4 | 1.644644567 |
| Brsk2 | 2.172446145 | Gtf2a1 | 1.826336279 | Naip6 | 1.643373664 |
| Cdkl2 | 2.171509052 | Nolc1 | 1.82454386 | Hk1 | 1.643066226 |

Figure 6:
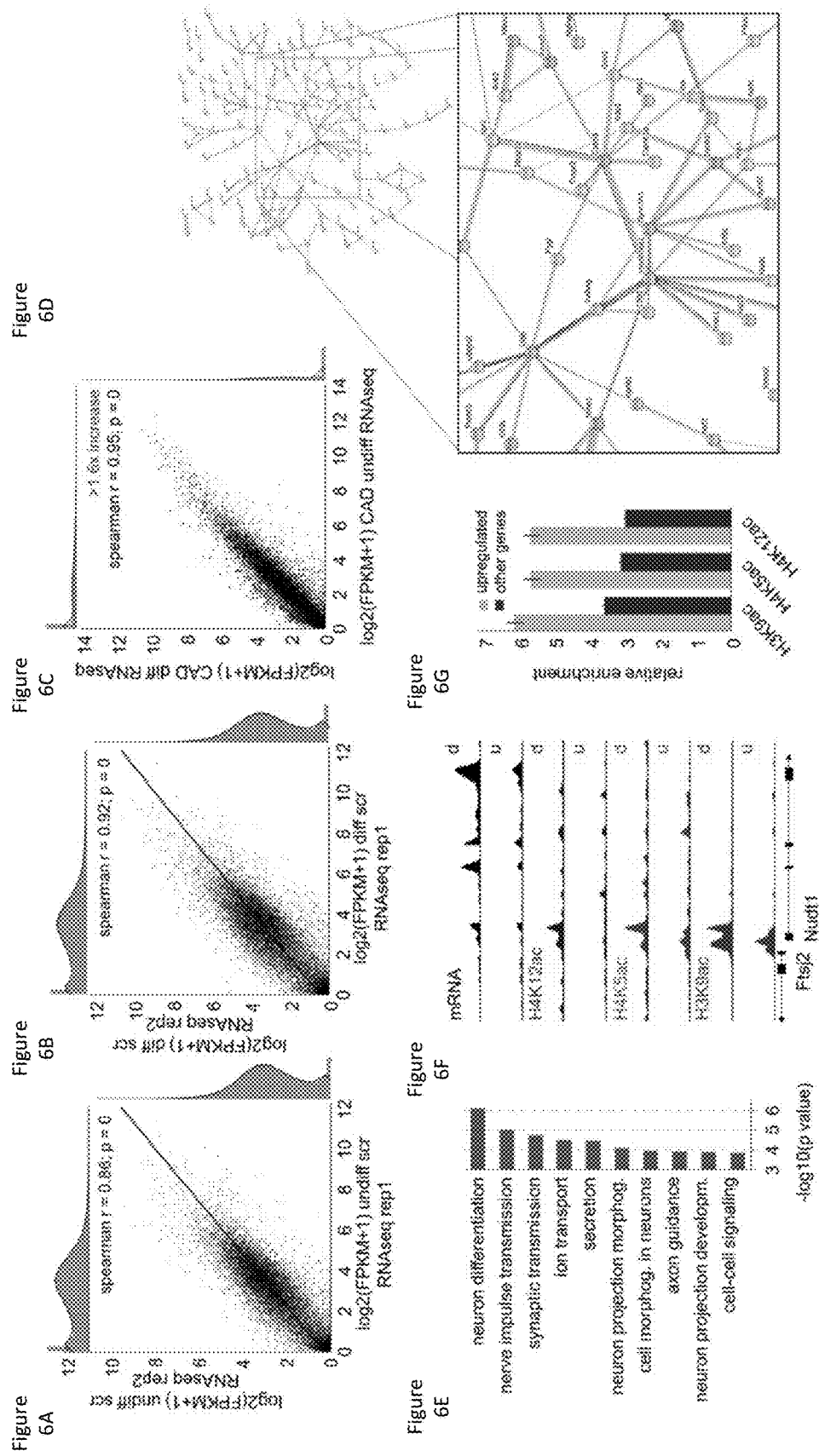
FIG. 6, comprising
Figure 6:
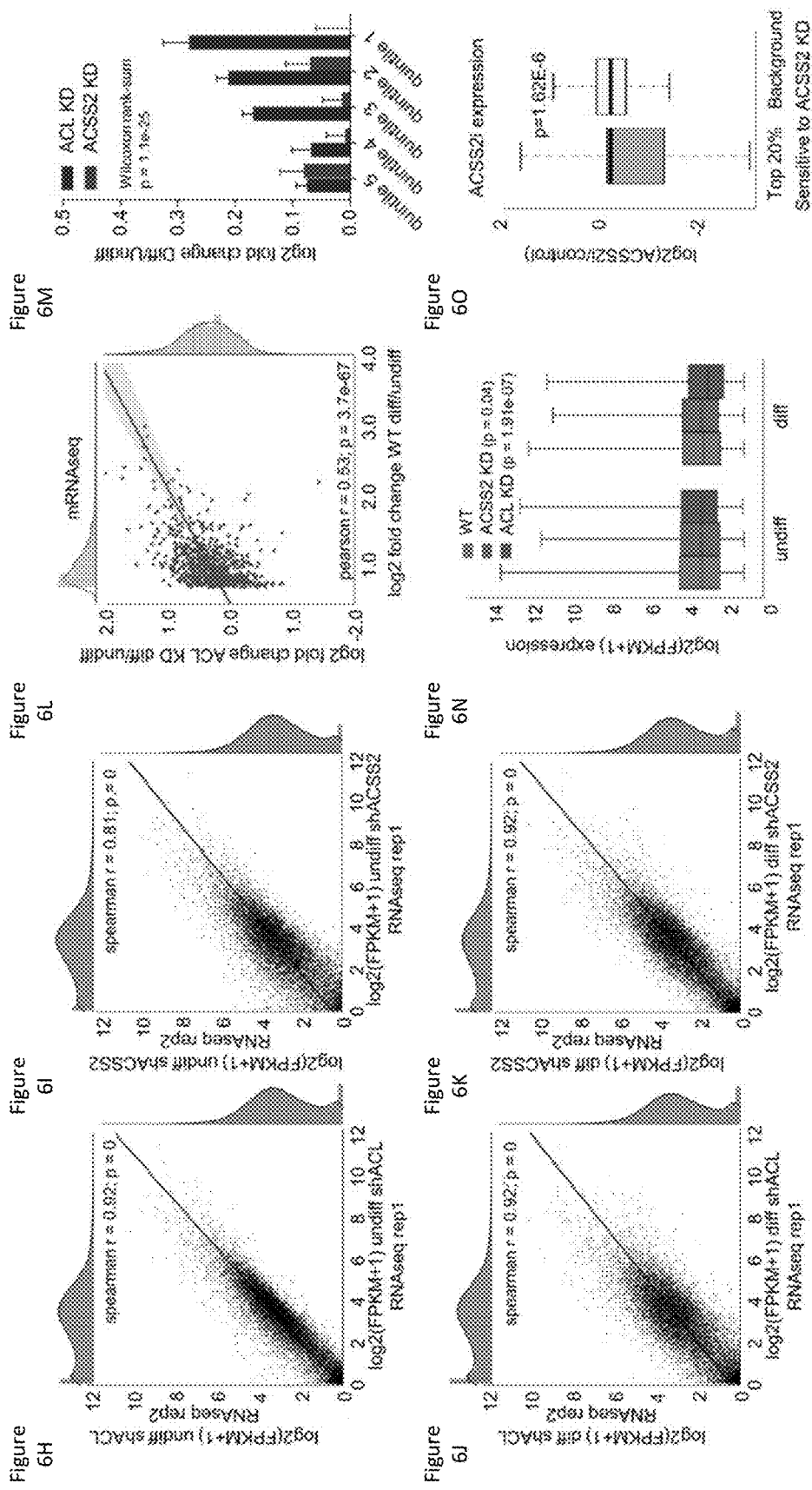

The metabolite acetyl-CoA is required by HAT enzymes for histone acetylation. To investigate histone acetylation during differentiation of CAD cells into neurons, chromatin immunoprecipitation with high-throughput DNA sequencing (ChIP-seq) was performed for histone H3 lysine 9 acetylation (H3K9ac), H4K5ac, and H4K12ac (see Methods). All marks were enriched upon differentiation at upregulated neuronal genes (for example, at nudix-type motif 1 (Nudt1)) (FIG. 6F). Overall, the 894 upregulated neuronal genes displayed higher acetylation than all other genes (FIG. 6G).

The levels of ACSS2 or ACL were reduced using short hairpin RNAs (shRNA) before cell differentiation and RNA-seq (FIG. 6H, FIG. 6I, FIG. 6J, FIG. 6K). The induction of neuronal genes was lost in the ACSS2 knockdown cells (Pearson r=0.15; FIG. 1D, FIG. 1E), whereas the same genes retained a strong correlation in transcriptional fold-change in ACL knockdown cells (Pearson r=0.53; FIG. 5L). The top 10% upregulated genes in differentiated wild-type cells were stratified into quintiles (FIG. 1I), and it was found that ACSS2 knockdown strongly lowered upregulation across all quintiles (FIG. 1I: green bars; $P=7.2 \times 10^{-252}$, Wilcoxon rank-sum test). The ACL-knockdown cells showed the same upward trend as wild-type cells, in contrast to the severe defect in ACSS2-knockdown cells (FIG. 6M; $P=1.1 \times 10^{-25}$, Wilcoxon rank-sum test). Notably, ACL-knockdown cells showed lower global transcript levels ($P=1.91 \times 10^{-7}$, Mann-Whitney U-test), unlike ACSS2-knockdown cells, which showed a less severe genome-wide defect (FIG. 6N; P=0.04, Mann-Whitney U-test). ACL thus has a broad but non-specific effect on gene expression, whereas ACSS2 is required for upregulation of the neuronal gene expression program upon differentiation of CAD cells into neurons.

Further, it was tested whether ACSS2 catalytic activity is required for the neuronal gene expression program using a small-molecule specific inhibitor of ACSS2 (ACSS2i)

(Comerford, S. A. et al., 2014, Cell, 159:1591-1602). RNA-seq showed a reduction in differentiation-induced genes (FIG. 1G), and the genes whose expression was affected by ACSS2-knockdown were also highly sensitive to the ACSS2i (FIG. 6O, P=1.62×10$^6$).

Recruitment of ACSS2 to Chromatin

The direct association of ACSS2 with chromatin was investigated using ChIP-seq of differentiated CAD cells (see Methods). Two ACSS2 antibodies showed a high correlation both for model-based analysis of ChIP-seq (MACS) overlapping peaks (Spearman r=0.82; FIG. 7A), and for global enrichment over 1-kb genomic windows (Spearman r=0.73; FIG. 7B). Binding of ACSS2 correlated with increases in histone H3K9ac, H4K5ac, and H4K12ac in differentiated relative to undifferentiated CAD cells, for instance at the promoters of Nudt1 and Tab2 (TAK1-binding protein 2; FIG. 7C, FIG. 7D). Both genes have been linked to neurodegenerative disorders; the Nudt1 hydrolase oxidizes purine nucleoside triphosphates to prevent RNA incorporation, and Tab2 regulates signal transduction pathways in neurons (Sardi, S. P. et al., 2006, Cell, 127:185-197). Gene ontology analysis showed that genes proximal to ACSS2 peaks were linked to neuronal differentiation (FIG. 7E). Hence, chromatin-associated, neuronal gene promoter-proximal ACSS2 may provide a local source of acetyl-CoA to HAT enzymes.

ACSS2 binding relative to histone acetylation was examined, and it was found that 80% of ACSS2 peaks upstream of the nearest target gene overlapped an acetylation peak or had an acetylation peak downstream towards the targeted transcription start site (TSS; FIG. 7F, FIG. 7G). A substantial number (13-15% of all ACSS2 peaks genome-wide) directly overlapped peaks of H3 and H4 acetylation (FIG. 7H). In addition, the height of ACSS2 peaks correlated overall with intersected histone acetylation peaks (FIG. 7I, FIG. 7J, FIG. 7K). This peak height correlation suggests that H4 acetylation might be most responsive to ACSS2-derived acetyl-CoA, in particular H4K12ac, a mark that has been linked to defective memory formation during aging (Peleg, S. et al., 2010, Science, 328:753-756). In general, the most enriched ACSS2 peaks displayed the strongest histone acetylation enrichment (FIG. 7L, FIG. 7M, FIG. 7N).

Putative recruitment of ACSS2 by transcription factor binding was investigated using de novo motif discovery over ACSS2 ChIP-seq peaks, which revealed binding sequences predicted for neuronal transcription factors. The most enriched motif was Yin Yang1 (YY1) (FIG. 7O; P=1×10$^{-599}$), which recruits the two acetyl-CoA-dependent HAT enzymes CREB-binding protein (CBP) and E1A binding protein (p300) (17), consistent with the idea that ACSS2 fuels nearby catalytic HAT activity.

Figure 8:
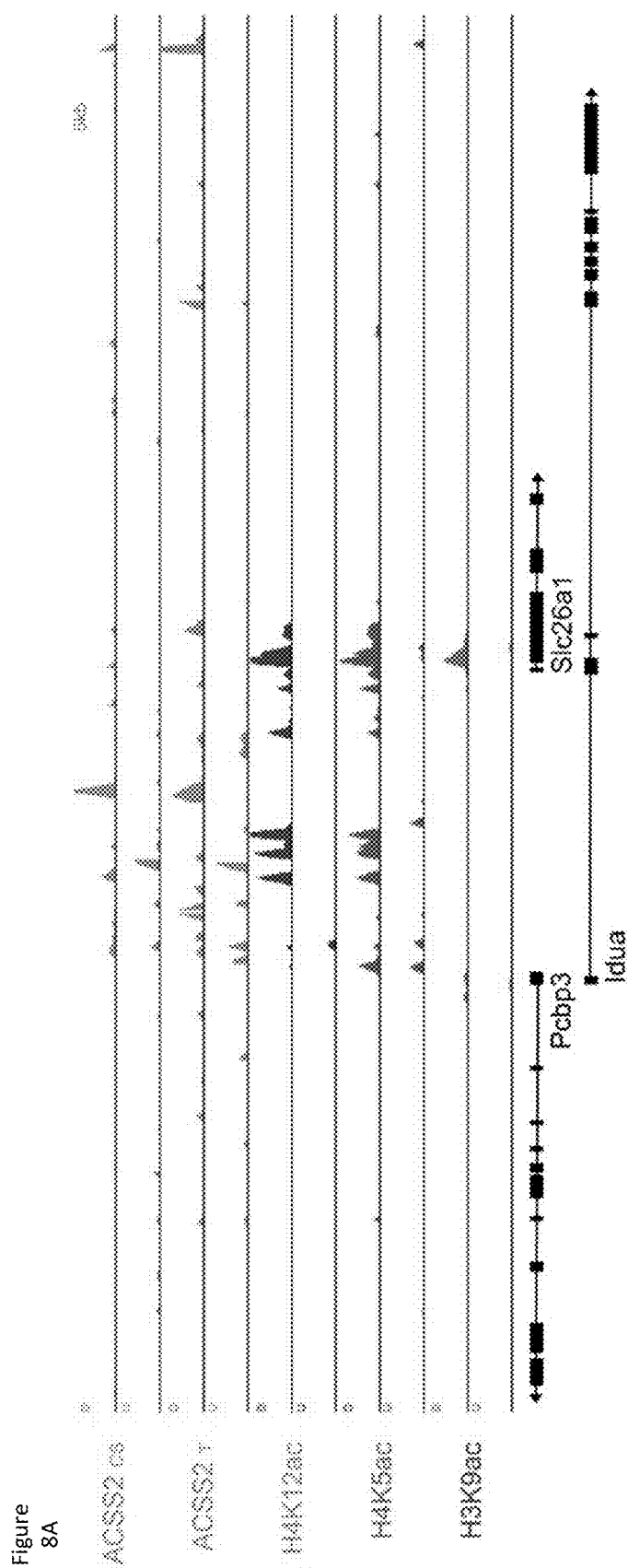
FIG. 8, comprising
Figure 8:
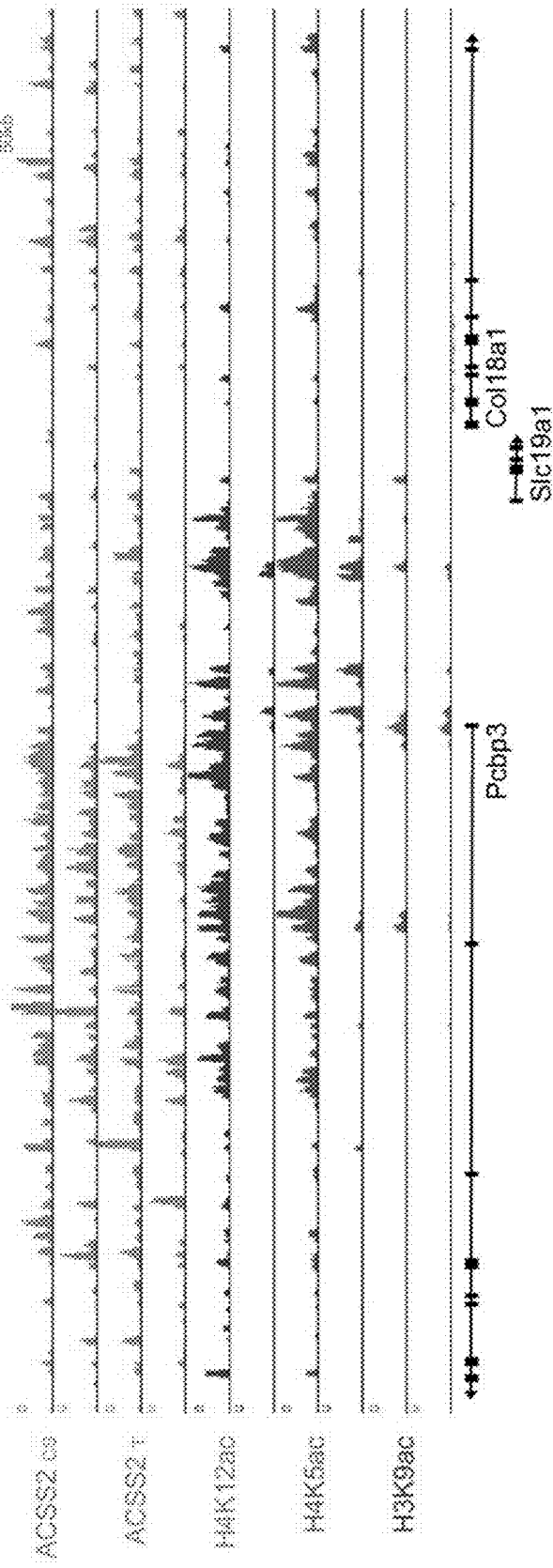

Initial peak analysis did not identify all peaks of ACSS2 or acetylation (FIG. 8A, FIG. 8B), so gene body enrichment was analyzed and there were additional prominent examples, such as Camk2a (FIG. 2A), which encodes the CaMKII alpha chain that is required for hippocampal long-term potentiation (LTP) and spatial learning. ACSS2 and acetylation co-occupancy profiles were similar at Camk2a and Nudt1 (FIG. 7C). Meta-gene analysis indicated that the top 5% of ACSS2-enriched genes had levels of acetylation up to threefold higher than the mean across all genes (FIG. 9A, FIG. 9B, FIG. 9C, FIG. 9D), and genes with the greatest fold-change in differential ACSS2 binding had the highest histone acetylation levels (FIG. 2C; FIG. 9E, FIG. 9F, FIG. 9G, FIG. 9H). Gene ontology term enrichment showed that the top ACSS2-bound and acetylated genes were neuron-specific (FIG. 2B).

Figure 2:
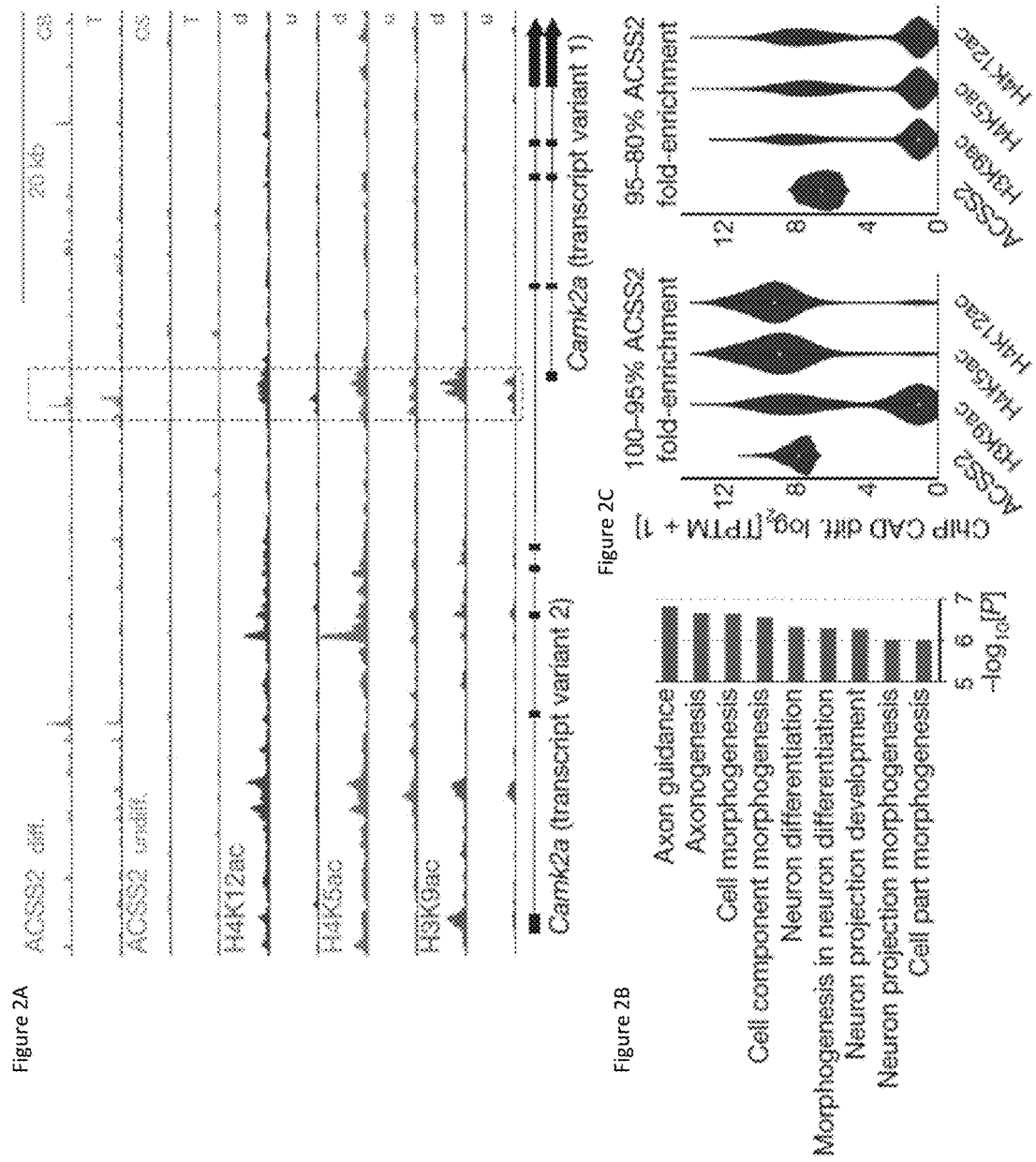
FIG. 2, comprising
Figure 2:
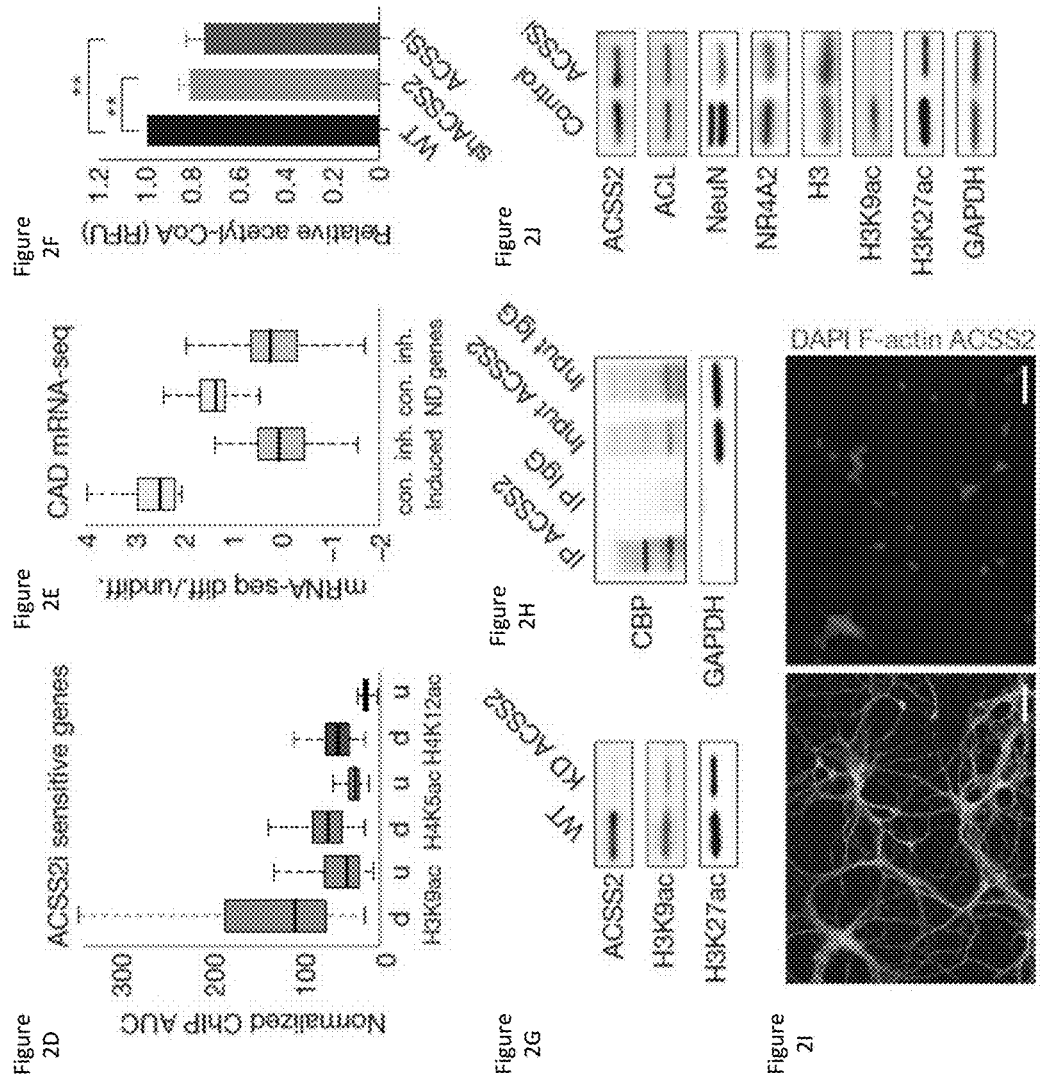

At all induced genes, ACSS2 binding was concomitant with increased histone acetylation (FIG. 7P), and the 299 genes that showed reduced expression upon ACSS2i treatment were those with the greatest differentiation-linked increases in histone acetylation (FIG. 2D). In total, about 9% of genes previously linked to neuronal differentiation (ND genes, AmiGO annotation set of 1,315 genes) were induced in differentiated CAD cells, and these induced genes were exceptionally sensitive to ACSS2i treatment (FIG. 2E, 'Induced'). Moreover, although the entire ND gene class did not change expression in differentiated CAD cells, their expression was markedly reduced by ACSS2i treatment (FIG. 2E, 'ND genes'). The interaction between differentiation-linked gene expression changes and ACSS2 recruitment to chromatin was visualized using multiple linear regression analysis, and a remarkable relationship between higher ACSS2 enrichment (red) and increased gene expression was found (FIG. 9I). Overall, the CAD cell genomic data demonstrate dynamic ACSS2 enrichment in differentiated neurons linked to increased histone acetylation and involvement in transcriptional upregulation of neuronal genes.

ACSS2 Functions in Neuronal Histone Acetylation

Nuclear acetyl-CoA levels was measured in ACSS2 knockdown cells (FIG. 2F; mean Δ=−0.19±0.03, P=0.003) and in cells treated with ACSS2i (FIG. 2F; mean Δ=−0.25±0.05, P=0.006) and it was found that levels of acetyl-CoA were similarly decreased. This finding supports the theory that ACSS2 enzymatic activity supplies nuclear acetyl-CoA. Global histone acetylation levels of transcription-linked H3K27ac and H3K9ac were reduced in ACSS2 knockdown cells (FIG. 2G, FIG. 10A), and these marks are key substrates of the transcriptional coactivators CBP and p300 with roles in hippocampal LTP and long-term memory (18). ACSS2 co-immunoprecipitated with acetylated chromatin, specifically H3K9ac, H3K27ac, and H4K12ac (FIG. 10B), and also with CBP (FIG. 2H), suggesting that ACSS2 binds chromatin at transcriptionally active genes to increase histone acetylation during memory formation in vivo (Wood, M. A. et al., 2005, Learn. Mem., 12:111-119; Korzus, E. et al., 2004, Neuron, 42:961-972; Vecsey, C. G. et al., 2007, J. Neurosci., 27:6128-6140).

Figure 10:
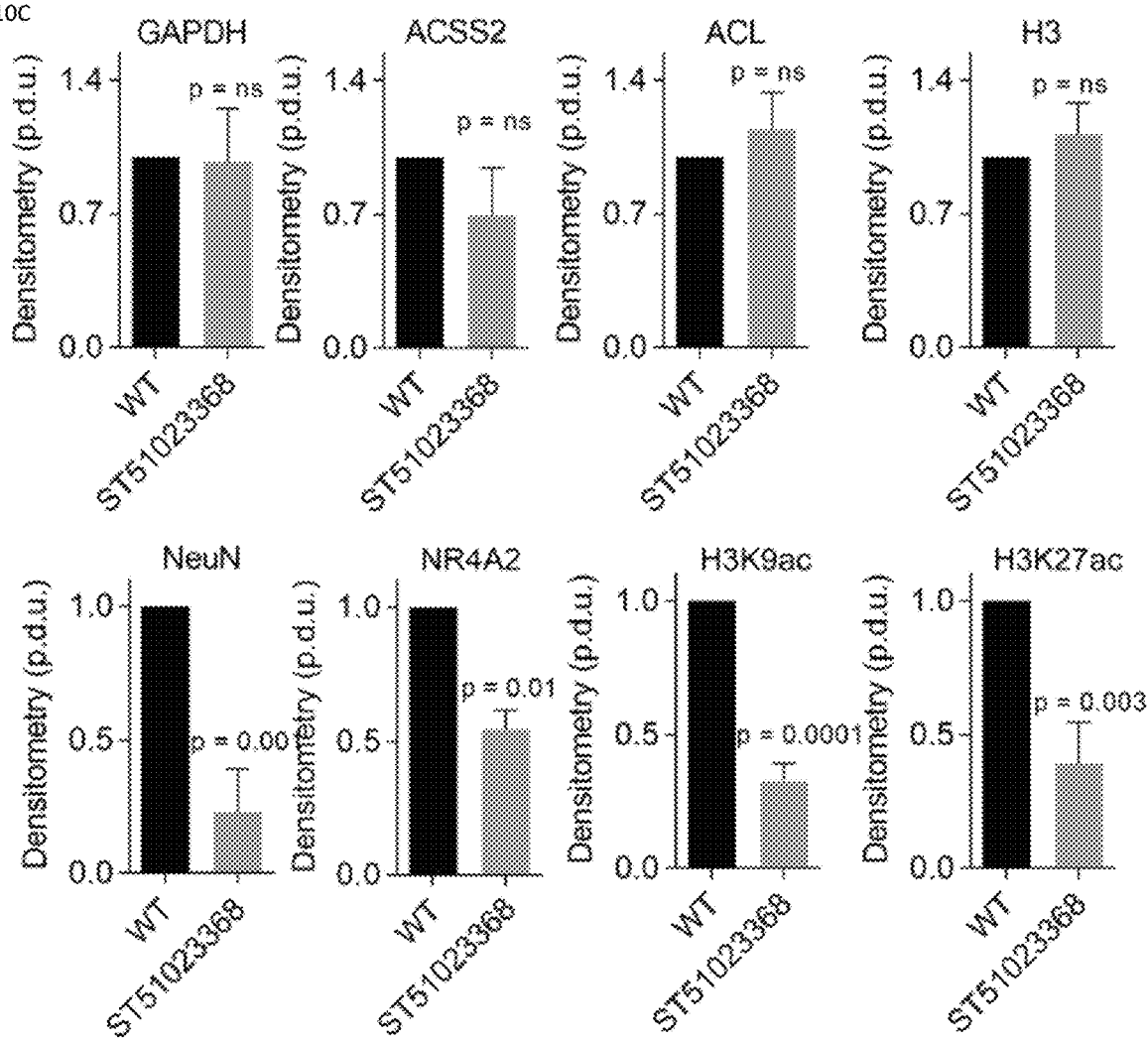
FIG. 10, comprising

ACSS2 was examined in primary mouse hippocampal neurons, given their capacity for depolarization and expression of key memory-related neuronal genes. ACSS2 was localized to the nucleus (FIG. 2I), and ACSS2i treatment reduced neuronal marker expression and histone acetylation without lowering ACSS2 levels (FIG. 2J, FIG. 10C). Expression of ACL did not change (FIG. 2J), indicating that ACL is less important than ACSS2 in the regulation of histone acetylation in hippocampal neurons.

Chromatin association of ACSS2 and H3K9ac was assessed in vivo using ChIP-seq in mouse hippocampus. The hippocampal H3K9ac mapping strongly correlated with ENCODE mouse forebrain H3K9ac ChIP-seq (Spearman coefficient of multiple correlation R=0.67), with similar peak distribution (FIG. 11A). Hippocampal ACSS2 and H3K9ac corresponded genome-wide and over three canonical neuronal genes involved in memory (Arc, Egr2 and Nr2f2; FIG. 3A, FIG. 3B). In addition, ACSS2 promoter binding and H3K9ac correlated with RNA-seq in the hippocampus (FIG. 3C). A small number of genes were found that were ACSS2-bound but not H3K9ac enriched that were silent, similar to genes not enriched for ACSS2 or H3K9ac (FIG. 3D). By contrast, genes enriched for H3K9ac were actively transcribed, but genes enriched for both ACSS2 and H3K9ac were most highly expressed (FIG. 3D).

Physical association of ACSS2 and CBP in differentiated CAD cells (FIG. 2H) correlated with gene colocalization of ACSS2 and CBP in the hippocampus, together with H3K27ac (from public mouse cortex CBP and H3K27ac ChIP-seq data; ACSS2:CBP overlap P=3.23×10$^{-16}$ by hypergeometric test). Overall, 57% of ACSS2-associated genes were co-targeted by H3K27ac (FIG. 3E), and ACSS2 and CBP co-targeted genes were enriched for gene ontology terms involved in synaptic membrane potential (FIG. 11B, FIG. 11C). Motif analysis at hippocampal ACSS2 peaks show that Nrf1—a transcription factor that regulates neurite growth—predicted binding at 45% of ACSS2 sites (FIG. 3F), evoking an ACSS2-CBP recruitment mechanism. Moreover, ACSS2i-sensitive genes (50%: 145 of 289) had proximal ACSS2 within 10 kb of the TSS (hypergeometric analysis, P=7.6986×10$^8$), consistent with a direct role for chromatin-bound ACSS2 in transcription.

ACSS2 Regulates Long-Term Memory Storage

Hippocampus-dependent spatial memory occurs through activity-dependent changes in gene expression that are coordinated, in part, through epigenetic modifications, specifically histone acetylation (Barrett, R. M. et al., 2011, Neuropsychopharmacology, 36:1545-1556; Graff, J. et al., 2012, Nat. Commun., 3:991). ACSS2 is expressed throughout the hippocampus (Lein, E. S. et al., 2007, Nature, 445:168-176; Ariyannur, P. S. et al., 2010, J. Comp. Neurol., 518:2952-2977) (FIG. 12A), and thus could mediate histone acetylation to upregulate neuronal gene expression during memory consolidation (Barrett, R. M. et al., 2011, Neuropsychopharmacology, 36:1545-1556; Maren, S. et al., 2000, Behav. Brain Res., 110:97-108). To investigate the role of ACSS2 in the adult hippocampus, ACSS2 expression was attenuated in the dorsal hippocampus by shRNA knockdown using a viral vector (FIG. 4A, FIG. 4B). Compared to control-injected mice, ACSS2 knockdown mice showed similar levels of locomotion, coordination, body weight, and anxiety-related thigmotaxis during open field exploration (Stanford, S. C., 2007, J. Psychopharmacol., 21:134-135) (FIG. 12B, FIG. 12C, FIG. 12D; not significant, n=10 per group); therefore, ACSS2 knockdown did not cause gross behavioral alterations.

To assess hippocampus-dependent spatial memory, an object-location memory paradigm was used (Balderas, I. et al., 2008, Learn. Mem., 15:618-624). Animals explored three different objects during training, and long-term memory was tested by re-exposure 24 hours later with one object moved to a different location (FIG. 4A, right). In training, control and knockdown mice showed no difference in exploration (FIG. 4C, left). During memory retrieval, control mice showed increased exploration of the object that had been moved (FIG. 4C). By contrast, ACSS2 knockdown mice were impaired in spatial object memory (FIG. 4C and FIG. 12E, mean Δ=−5.01±1.21; P=8.3×10$^5$), and displayed a lower discrimination index (FIG. 4D; % ΔDI=−29.5±11.4; P=0.02). ACSS2 knockdown mice showed reduced total object exploration during the test (FIG. 4C), suggesting diminished novelty associated with intact recognition of the objects from the training session (mean Δ=−6.13±2.15; P=0.02, n=10 per group).

Previous studies have shown that long-term contextual fear memory is mediated by the ventral hippocampus when manipulations of the dorsal hippocampus occur before training (Rogers, J. L. et al., 2006, Neurobiol. Learn. Mem., 86:72-81). Therefore, as a control experiment, mice injected with the ACSS2 knockdown shRNA or eGFP in the dorsal hippocampus were subjected to a contextual fear conditioning paradigm. During the 24-hour test session, there was no significant difference in the amount of freezing behavior between ACSS2-knockdown and eGFP mice (FIG. 12F, FIG. 12G) suggesting that the ventral hippocampus successfully mediated context-shock association. Overall, it was concluded that ACSS2 has a critical role in dorsal hippocampus-mediated long-term spatial memory.

ACSS2 Regulates Upregulation of Immediate Early Genes

Long-term spatial memory requires a rapid increase in histone acetylation and immediate early gene transcription to occur in a sensitive time window to enable memory consolidation (Barrett, R. M. et al., 2011, Neuropsychopharmacology, 36:1545-1556; Peixoto, L. L. et al., 2015, BMC Genomics, 16:S5); during memory retrieval, gene transcription also occurs for memory reconsolidation, and this can be prevented by inhibiting mRNA synthesis during the sensitive post-retrieval period (Mamiya, N. et al., 2009, J. Neurosci., 29:402-413). It was tested whether ACSS2 was involved in dynamic gene upregulation for hippocampal memory consolidation and reconsolidation by performing mRNA-seq on the dorsal hippocampus. Global gene expression changes were first identified that were induced by spatial object training, which has not previously been investigated genome-wide. Dorsal hippocampi from control and shACSS2-knockdown mice were removed during the sensitive period of memory consolidation following spatial object training. To control for circadian oscillation, injected animals were included that had been handled but not trained.

Figure 12:
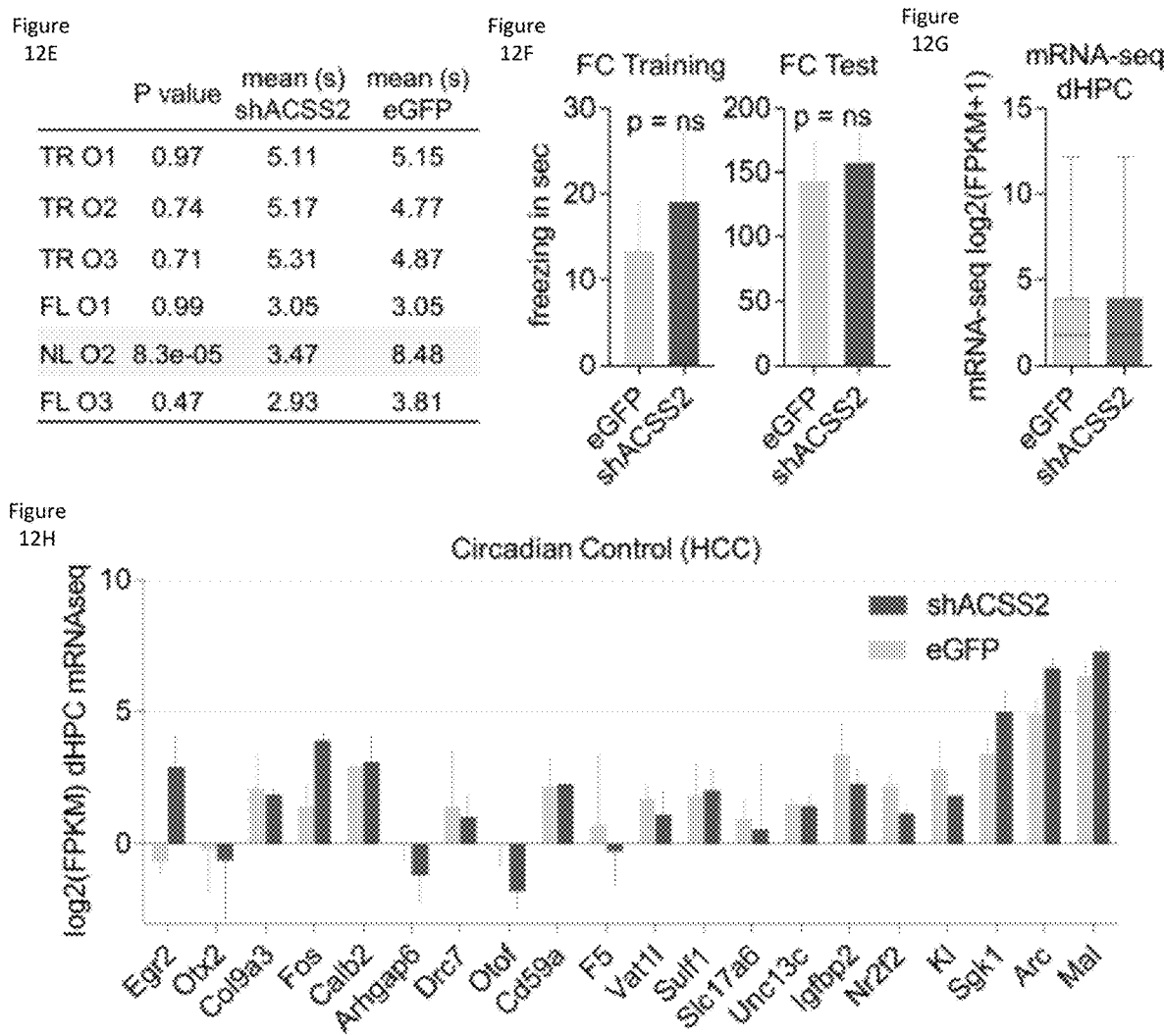
FIG. 12, comprising
Figure 13:
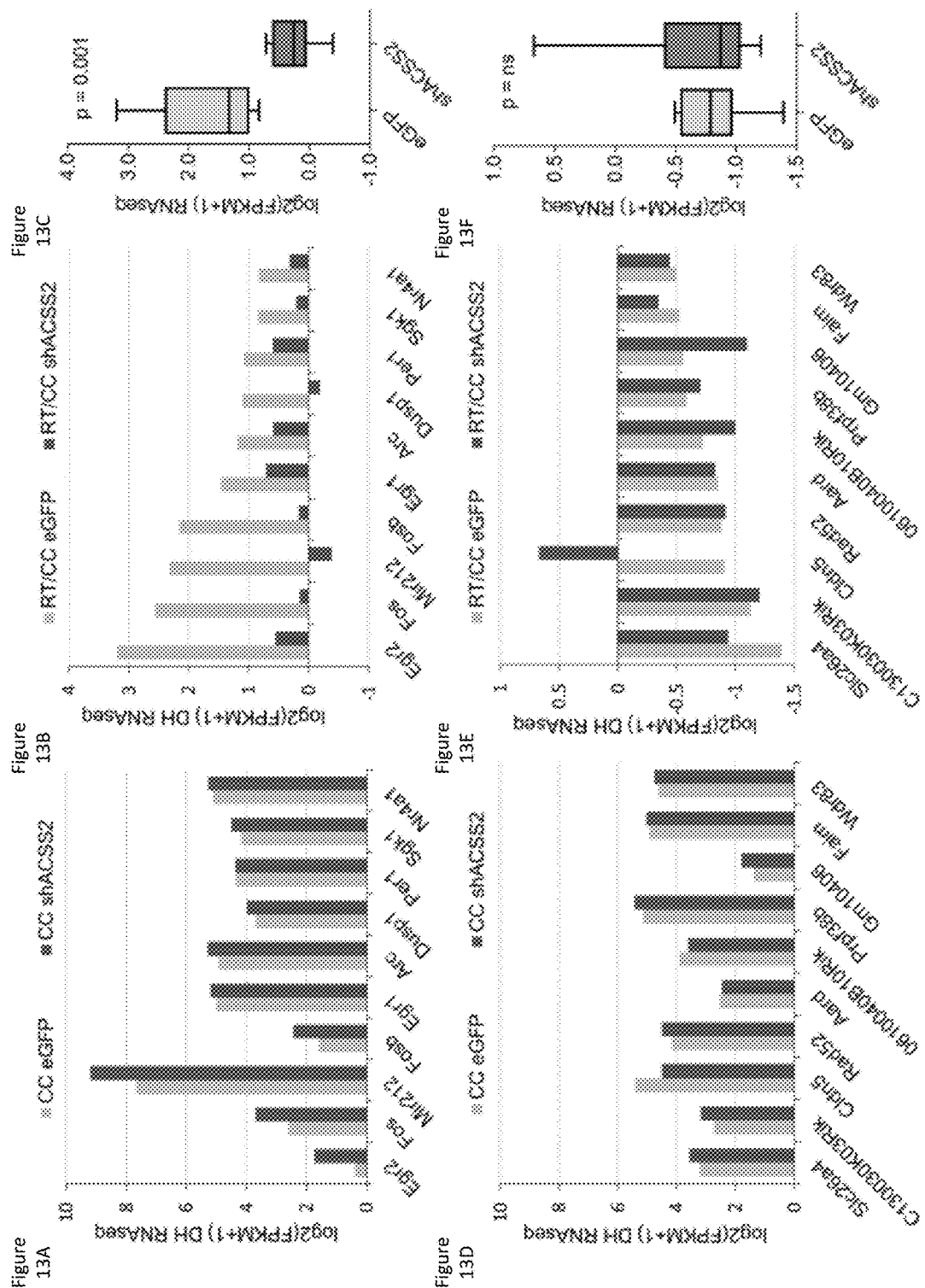
FIG. 13, comprising

Genes that were differentially expressed following training were identified by transcriptome comparison of trained control-injected mice to untrained circadian control-injected mice using Cuffdiff. A small number of genes were induced immediately after training, including immediate early genes such as Egr2, Fos, Nr2f2, Sgk1 and Arc (FIG. 4E). Importantly, baseline expression of these memory-associated genes in untrained control and ACSS2-knockdown mice was remarkably similar (FIG. 12H). By contrast, dynamic upregulation of these immediate early genes by training was greatly reduced by ACSS2 knockdown (FIG. 4E).

It was further tested whether ACSS2 also regulates immediate-early gene expression in the dorsal hippocampus during memory reconsolidation. Therefore, the hippocampal mRNA-seq analysis was focused on previously identified and validated genes that become upregulated following memory retrieval (Peixoto, L. L. et al., 2015, BMC Genomics, 16:S5; Poplawski, S. G. et al., 2014, Neurobiol. Learn. Mem., 116:90-95). Retrieval-associated induction of immediate early genes during the sensitive reconsolidation period was blocked by ACSS2 knockdown, whereas retrieval-linked downregulation during the same period was not (FIG. 13A, FIG. 13B, FIG. 13C, FIG. 13D, FIG. 13E, FIG. 13F).

Summary

Metabolic state can regulate chromatin structure, in particular by inducing histone modifications (Gut, P. et al., 2013, Nature, 502:489-498). Here, a connection is established between cellular metabolism and neuronal plasticity, and a neuronal function of ACSS2 as a chromatin-bound transcriptional coactivator that stimulates histone acetylation and gene expression is revealed.

Acetyl-CoA metabolism is cell- and tissue-specific, and is frequently disregulated in malignant transformation (Comerford, S. A. et al., 2014, Cell, 159:1591-1602; Mashimo, T. et al., 2014, Cell, 159:1603-1614). In adipose cells, ACSS2 partially localizes to the nucleus and contributes to histone acetylation under conditions of low glucose (Wellen, K. E. et al., 2009, Science, 324:1076-1080; Gao, X. et al., 2016, Nat. Commun., 7:11960), but the principal metabolic determinant of histone acetylation is ACL9. By contrast, it is shown herein that post-mitotic neurons rely on chromatin-recruited ACSS2 to supply acetyl-CoA for histone acetylation. Notably, fasting lowers acetyl-CoA and protein acetylation in most tissues, but acetyl-CoA levels remain unchanged in the brain (Marifio, G. et al., 2014, Mol. Cell, 53:710-725), indicating that neuronal ACSS2 has an important role in the fasted state when acetyl-CoA production by citrate-dependent ACL is reduced.

Optimal acetyltransferase activity requires an increased local acetyl-CoA to CoA ratio, which determines the catalytic activity and substrate specificity of HAT enzymes (Cai, L., et al., 2011, Mol. Cell, 42:426-437; Wellen, K. E. et al., 2009, Science, 324:1076-1080; Takahashi, H. et al., 2006, Mol. Cell, 23:207-217). This finding suggests that histone acetylation can be controlled by changing levels of nuclear acetyl-CoA. Thus, chromatin-bound ACSS2 could provide acetyl-CoA to fuel HAT activity locally, instantaneously recycling CoA and could also recapture acetate from deacetylation reactions. The data presented herein demonstrates specific chromatin binding by ACSS2 at neuronal genes and link localization to upregulation of histone acetylation and gene transcription in spatial memory (FIG. 4F), which requires increased histone acetylation (Graff, J. et al., 2013, Nat. Rev. Neurosci., 14:97-111; Graff, J. et al., 2012, Nat. Commun., 3:991). A crucial role for ACSS2 in upregulation of immediate early genes with key functions in neuronal plasticity and memory is demonstrated, leading to a critical role for this molecule in long-term memory consolidation.

Epigenetic mechanisms continue to be revealed as important regulators of neural function and behavior, and have been implicated in neuropsychiatric diseases, including anxiety disorders and depression (Kandel, E. R. et al., 2014, Cell, 157:163-186; Graiff, J. et al., 2013, Nat. Rev. Neurosci., 14:97-111; Walker, D. M. et al., 2015, Curr. Opin. Neurobiol., 30:112-121). In establishing ACSS2 as a key regulator at the interface of metabolic environment and neuronal chromatin, this example provides a previously unrecognized enzymatic target for the development of therapies to treat neurological and cognitive disorders.

Example 2: ACSS2 and Alcohol

Figure 17:
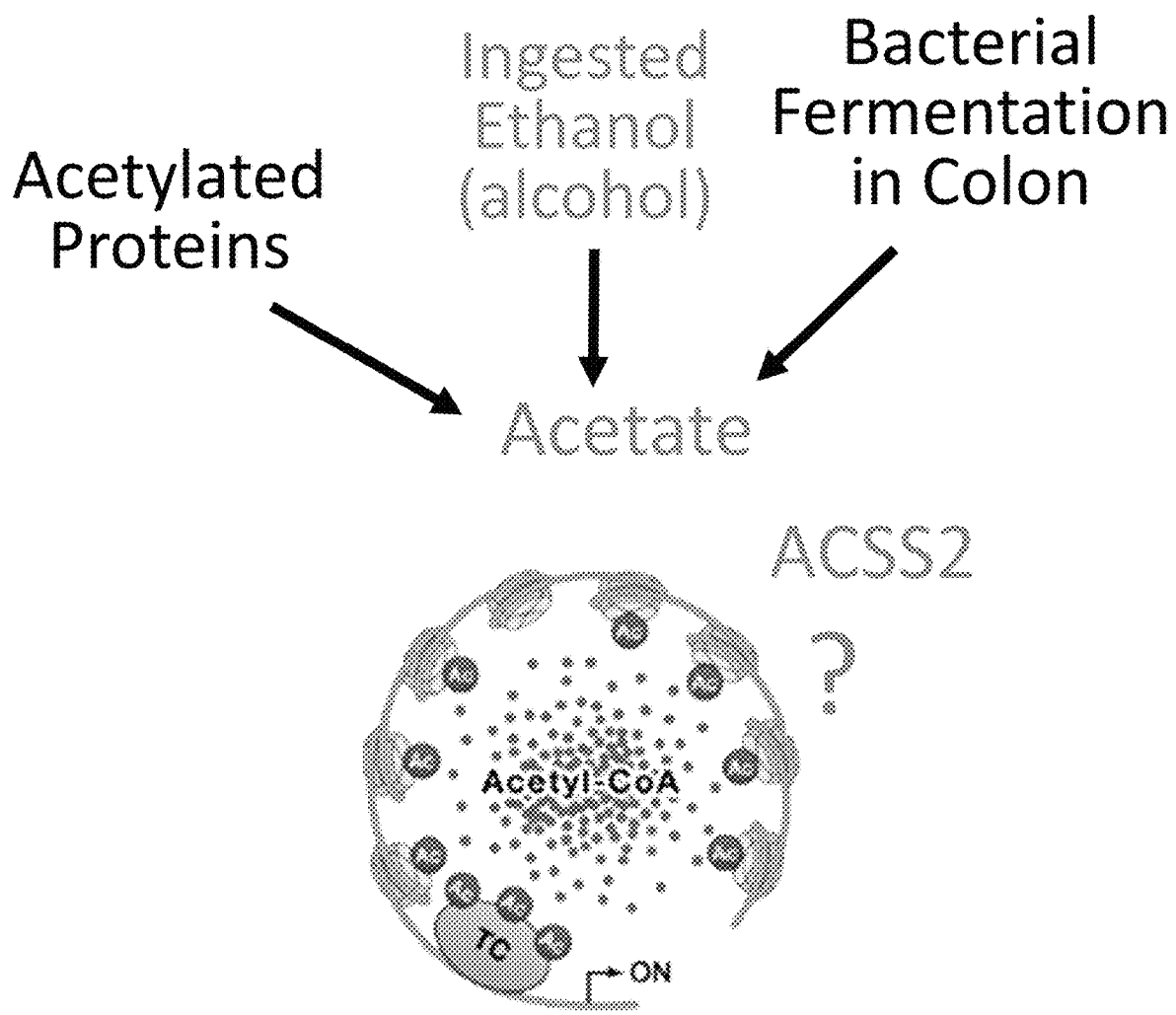
FIG. 17 depicts the physiological sources of acetate.
Figure 17:

The physiological sources of acetate include 1) acetylated proteins; 2) bacterial fermentation in colon; and 3) ingested ethanol. However, it is unknown if alcohol is destined for neuronal chromatin (FIG. 17).

Figure 18:
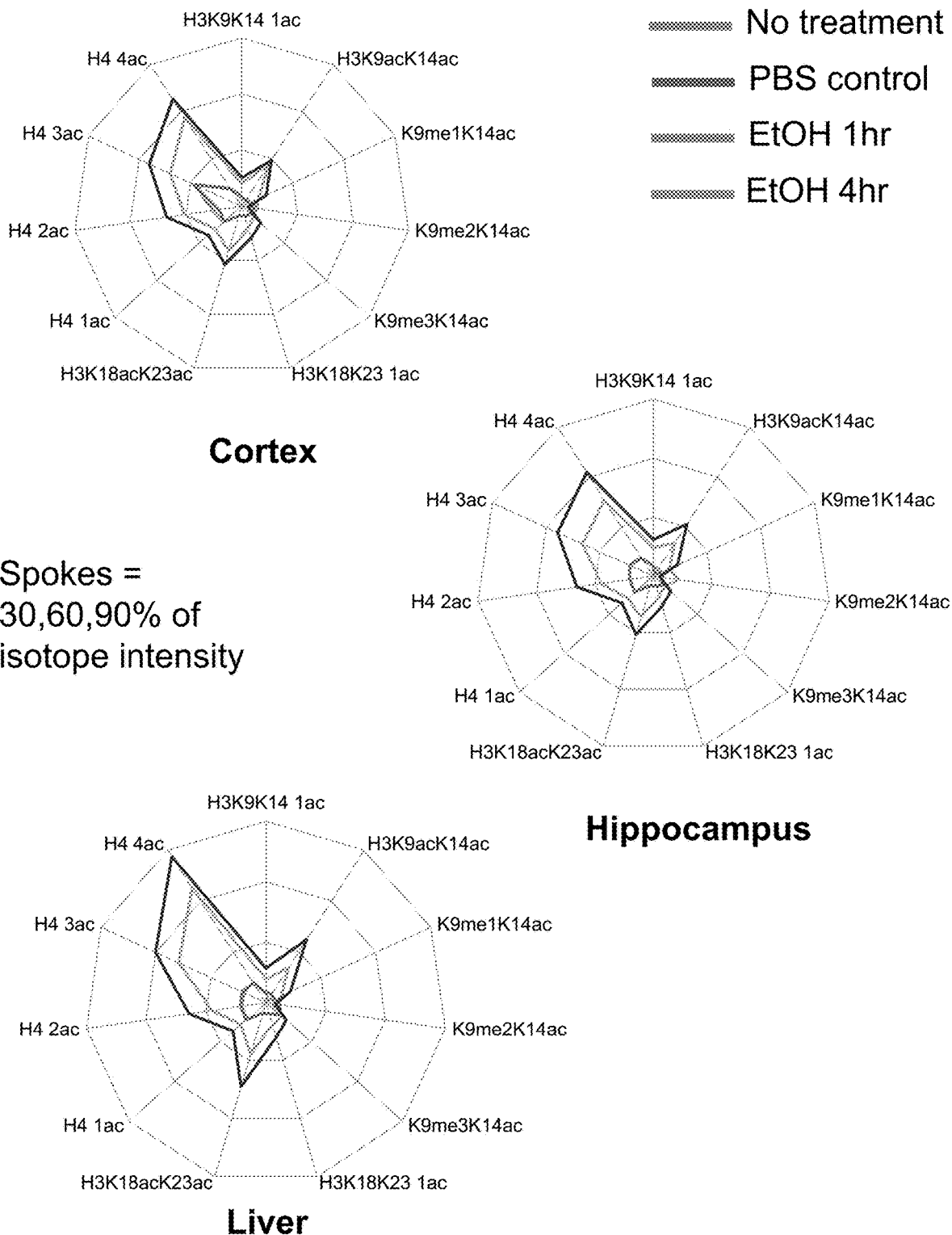
FIG. 18 depicts graphs measuring the histone acetylation in the cortex, hippocampus, and liver of mice after intraperitoneal injection of EtOH-$^{13}C_2$.

To study the effects of acute alcohol administration, mice are injected intraperitoneally with EtOH-$^{13}C_2$, to mimic "binge" drinking. Mass spectrometry is used to determine the acetylation of liver and brain histones. Heavy C acetate is incorporated into liver and brain histones by 1 hour post IP injection (FIG. 18).

Figure 19:
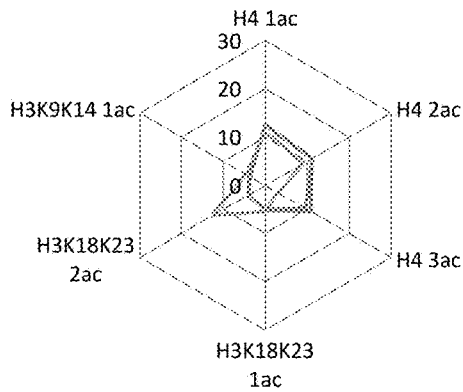
FIG. 19 depicts graphs measuring the histone acetylation in the hippocampus of ACSS2-knockdown mice.
Figure 19:
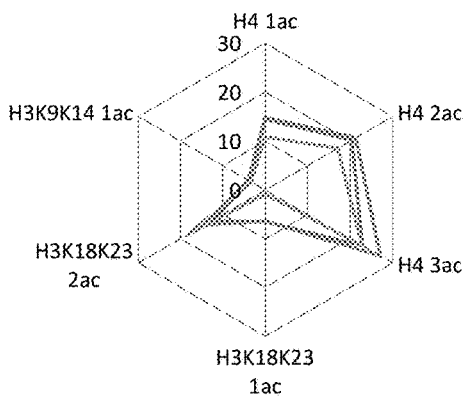
Figure 19:
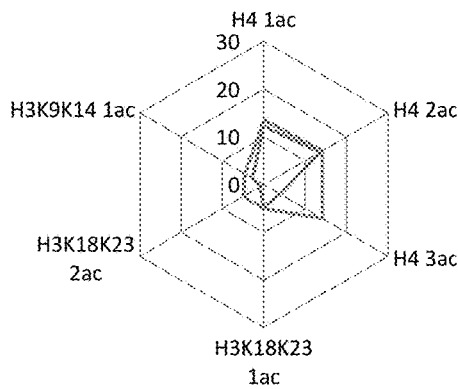
Figure 20:
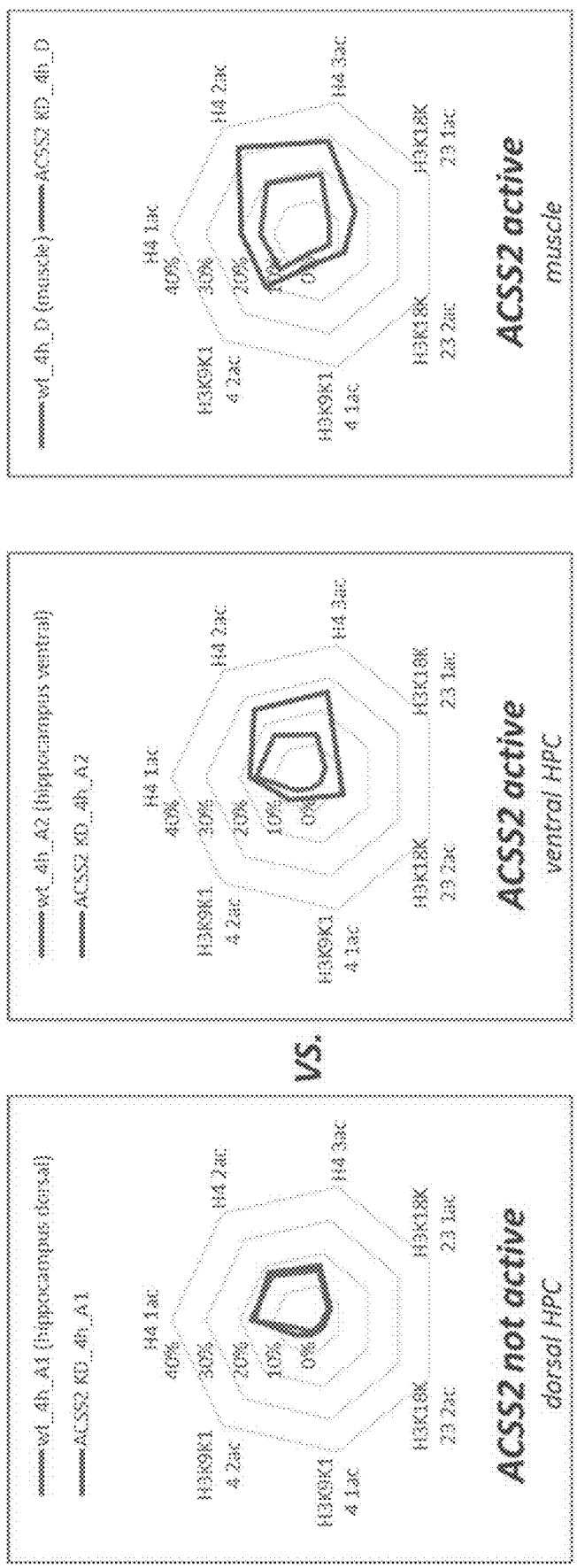
FIG. 20 depicts graphs demonstrating the difference in histone acetylation in the dorsal HPC, ventral HPC and muscle of ACSS2-knockdown mice versus wild type mice.

Next, it was determined if ACSS2 is required for heavy C acetate incorporation into hippocampus acetylated histones. ACSS2 KD in dorsal HPC leads to A loss of incorporation into dorsal HPC (4 h). The radar plot displays the relative abundance of the heavy isotope (as compared to the light one). The heavy isotope is higher in the knock-down as compared to wild type only in hippocampus ventral and in muscle. In hippocampus dorsal it remains at the same low levels as in WT mice (injected with unlabeled EtOH). (FIGS. 19-20).

Example 3: Liver Alcohol Metabolism Directly Fuels Histone Acetylation in the Brain In the adult brain, epigenetic control of gene expression has important roles in the processing of neural activity. Emerging evidence suggests that epigenetic regulation is dependent on metabolic state, implicating specific metabolic factors in neural functions that drive behavior. In neurons, histone acetylation is dependent on the metabolite acetyl-CoA that is produced from acetate by chromatin-bound ACSS2 (Mews et al., Nature, 2017, 546:381-386). Here, using in vivo stable isotope labeling, it is shown that liver alcohol metabolism rapidly fuels histone acetylation in the brain by direct deposition of alcohol-derived acetyl groups onto histones in an ACSS2-dependent manner. A similar induction was also observed with heavy labeled acetate injection in vivo. In addition, injection of labeled alcohol into a pregnant mouse results in incorporation of labeled acetyl groups into the brains of the gestating fetuses. In isolated primary hippocampal neurons in vitro, extracellular acetate induced learning and memory-related transcriptional programs that were sensitive to ACSS2 inhibition were discovered. These findings establish a novel and direct link between hepatic alcohol metabolism and neuronal histone acetylation, providing the first evidence for dynamic signaling from liver metabolism directly to epigenetic regulation in neurons.

Existing research into the neurobiology of alcohol addiction has focused on limbic reward circuitry, changes in neurotransmission, and intracellular neuronal signaling cascades. However, the exact mechanisms by which alcohol exerts its psychotropic effects remain incompletely understood. While alcohol directly interacts with neuronal channel proteins, this pathway cannot explain many of the effects of alcohol intoxication on brain function (Ron et al., Nat. Publ. Gr., 2016, 17:576-591). Indeed, recent work converges on the notion that dysregulated gene expression is a key molecular mechanism of alcohol action on target tissues (Ron et al, Nat. Publ. Gr., 2016, 17:576-591; Zakhari, Alcohol Res., 2013, 35:6-16). In the brain, epigenetic regulation of gene expression enables integration of neural activity to continuously adapt circuit connectivity and has critical importance for expression of appropriate or—in the case of alcohol addiction—inappropriate behaviors (Ron, Nat. Publ. Gr., 2016, 17:576-591; Mews et al., Prog. Brain Res., 2017, 235:19-63; Robinson et al., Nat. Rev. Neurosci., 2011, 12:623-637; Egervari et al., Neurosci. Biobehav. Rev., 2018, 85:117-125). Emerging evidence suggests that such epigenetic regulation is dependent on metabolic state. Indeed, it was recently shown that histone acetylation controlling hippocampal memory formation is reliant on the metabolite acetyl-CoA, produced from acetate by chromatin-bound ACSS2 (Mews et al., Nature, 2017, 546:381-386). Notably, a major physiological source of acetate is via breakdown of alcohol in the liver, leading to rapidly increasing blood acetate (Sarkola et al., Alcohol. Clin. Exp. Res., 2002, 26:239-245). Neuronal histone acetylation may thus be under the influence of extracellular levels of acetate (Soliman et al., Mol. Cell. Biochem., 2011, 352:173-180). However, it is unknown whether hepatic alcohol metabolism directly affects histone acetylation in the brain.

The methods and materials are now discussed.

Histone Extraction

The cells were incubated in nuclear isolation buffer (NIB) (15 mM Tris-HCl, 15 mM NaCl, 60 mM KCl, 5 mM $MgCl_2$, 1 mM $CaCl_2$), 250 mM sucrose, pH 7.5, and 0.5 mM AEBSF, 10 mM sodium butyrate, 5 nM microcystein, 1 mM DTT added fresh) with 0.2% NP-40 on ice for 5 min. The nuclei were collected by centrifuging at 700×g at 4° C. for 5 min. The resulting nuclear pellet was washed twice with the same volume of nuclear isolation buffer without NP-40. Histones were then acid-extracted with 0.2 M $H_2SO_4$ for 3 hours at 4° C. with rotation. The insoluble nuclear debris were pelleted at 3400×g at 4° C. for 5 min, and the supernatant was retained. Next, histone proteins were precipitated by adding 100% trichloroacetic acid (TCA) in the ratio of 1:3 (v/v) for 1 hour at 4° C. The pellet was washed with acetone to remove acid residual. Histones were resuspended in 30 µl of 50 mM $NH_4HCO_3$ (pH 8.0).

Histone Propionylation and Digestion

The sample was mixed with 15 µl of derivatization mix, consisting in propionic anhydride and acetonitrile in a ratio of 1:3 (v/v), immediately followed by 7.5 µl of ammonium hydroxide to maintain pH 8.0. The sample was incubated for 15 minutes at 37° C., dried and the derivatization procedure was repeated one more time. Samples were then resuspended in 50 mM $NH_4HCO_3$ and incubated with trypsin (enzyme:sample ratio 1:20) overnight at room temperature. After digestion, the derivatization reaction was performed again twice to derivatize peptide N-termini. Samples were desalted using C18 Stage-tips prior to LC-MS analysis.

NanoLC-MS/MS

Samples were analyzed by using a nanoLC-MS/MS setup. NanoLC was configured with a 75 µm ID×25 cm Reprosil-Pur C18-AQ (3 m; Dr. Maisch GmbH, Germany) nanocolumn using an EASY-nLC nano-HPLC (Thermo Scientific, San Jose, CA, USA), packed in-house. The HPLC gradient was as follows: 5% to 32% solvent B (A=0.1% formic acid; B=80% acetonitrile, 0.1% formic acid) over 45 minutes, from 32% to 90% solvent B in 5 minutes, 90% B for 10 minutes at a flow-rate of 300 nL/min. nanoLC was coupled to an Orbitrap Elite mass spectrometer (Thermo Scientific, San Jose, CA, USA). The acquisition method was data independent acquisition (DIA) as described. Briefly, two full scan MS spectra (m/z 300-1100) were acquired in the ion trap within a DIA duty cycle, and 16 ms/ms were performed with an isolation window of 50 Da. Normalized collision energy (CE) was set to 35%.

Data Analysis

Raw MS data were analyzed manually. The 7 most intense peptides of histone H3 and H4 containing acetylations were selected, and the relative abundance of the 4th isotope was extracted (compared to the monoisotopic signal). The other peptides were not considered as, due to their low abundance, the relative abundance of all the isotopes could not be confidently quantified.

RNA-Sequencing

All RNA-seq data were prepared for analysis as follows: NextSeq sequencing data was demultiplexed using native apps on BaseSpace. Demultiplexed FASTQs were aligned by RNA-STAR 2.5.2 to assembly mml0 (GRCm38). Aligned reads were mapped to genomic features using HTSeq 0.6.1. Quantification, library size adjustment, and differential gene expression analysis was done using DESeq2 and Wald's test (pairwise contrasts between acetate and DMSO-treatment in the inhibitor-treated or untreated cells, followed by a set overlap of differentially expressed genes). Gene list overlaps were tested for significance using the hypergeometric test.

Functional Analysis

Gene Ontology analysis was performed using DAVID with an FDR cutoff of 10%, filtering categories with fewer than 10 genes or less than 2.5× fold enrichment over background. Motif analysis was performed using HOMER v4.6 on all ACSS2 peaks from published in vivo data (Mews et al., Nature, 2017, 546:381-386) targeting (by the nearest TSS) a gene sensitive to acetate with H3K9ac at the promoter using a fixed window of 300 bp (Mews et al., Nature, 2017, 546:381-386).

Mouse Experiments 8-week-old adult male mice or E18.5 pregnant females were used. Ethanol, ethanol-$d_6$, and sodium acetate-$d_3$ (Sigma-Aldrich) were administered via intraperitoneal (i.p.) injection and dosed at 2 g/kg (20% solution in saline, filtered through a Stericup GV filter). Conditioned place preference (CPP) was performed according to Cunningham et al. Briefly, Ugo Basile (Italy) mouse CPP boxes (Model Number: 42553) with external dimensions 35×18×29 cm were used. The apparatus was divided into two chambers (16× 15×25 cm) that differed in wall and floor pattern. Striped walls were paired with circle cutouts (1 cm) and solid gray walls were paired with square cutouts (0.5 cm). Sessions were run in a dark room at ambient temperature. Boxes were cleaned with 70% ethanol between animals. The paradigm consisted of 1 habituation day (5 min exploration in neutral environment), 1 pre-training session (20 min), 8 training days (biased subject assignment, alternating sessions of saline or ethanol i.p. immediately prior to 5 min session) and 1 post-training test session (20 min). Percent time spent in conditioned chamber was measured. Shapiro-Wilks test was used to assess normal distribution and Mann-Whitney test to determine learning.

Intracranial Injection of Viral Vector

Adult mice (8+ weeks of age) were anaesthetized with isoflurane gas (1-5% to maintain surgical plane) and placed in a sterile field within a stereotaxic device. Animals received an injection of bupivacaine (2.5 mg kg−1) for local anaesthesia before the skin was disinfected with betadine solution and the skull exposed with a short incision using sterile surgical equipment. Artificial tears were applied to eyes to ensure sufficient lubrication. A small hole (about 0.5 mm) was drilled in the skull over the target area using a stereotax and a stereotactic drill. A micro-syringe filled with viral vector was inserted into the dorsal hippocampus and slowly removed following injection (AP, −2.0 mm; DV, −1.4 mm; 14 ML, ±1.5 mm from bregma). ACSS2 knockdown vector, AAV2/9; U6.shACSS2.CMV.EGFP. All animals received a single dose of subcutaneous meloxicam (5 mg kg) as analgesia at induction and one dose per day for two days postoperatively as needed.

The results are now discussed.

To determine whether acetate from hepatic alcohol breakdown fuels dynamic histone acetylation in the brain, in vivo stable isotope labeling of protein acetylation was used and monitored by mass spectrometry (MS) (Mews et al., Methods Enzymol., 2016, 574:311-329). Specifically, mice were injected intraperitoneally with 2 g/kg deuterated ethanol (d6-EtOH) or control saline, and deuterium incorporation into acetylated histones was assessed at baseline, as well as 1 and 4 hours after intraperitoneal injections (FIG. 21A, bottom). Using advanced quantitative liquid chromatography-MS technology, the relative abundance of isotopically labeled histone acetylation in the brain and in peripheral tissues was quantified (FIG. 21A, top). EtOH-derived acetyl-groups were rapidly incorporated into histone acetylation in the brain, both in hippocampus and in prefrontal cortex (FIGS. 21B and 21C, FIG. 22A-22D). Label incorporation into histone acetylation was dynamic and heavy labeling decreased to baseline levels 8 hours following intraperitoneal (i.p.) injection. A similar response also occurred in the liver (FIG. 21D), which is the principal site of alcohol metabolism, and which has been previously shown to express high levels of ACSS2 (Zakhari, Alcohol Res., 2013, 35:6-16; Comerford et al., Cell, 2014, 159:1591-1602). In contrast, such rapid labeling of histone acetylation was not observed in skeletal muscle (m. gastrocnemius, FIG.

21E), which expresses relatively low levels of ACSS2 (Bonthuis et al., Cell Rep., 2015, 12:979-991).

To investigate the direct role of ACSS2 in alcohol-dependent acetylation in the brain, ACSS2 expression in the dorsal hippocampus (dHPC) was attenuated by shRNA knockdown using a previously validated viral vector (Mews et al., Nature, 2017, 546:381-386). In these ACSS2 knockdown (KD) animals, heavy-alcohol-derived histone acetylation was compared separately in the dHPC, where ACSS2 was reduced (ACSS2 KD), and in the ventral hippocampus (vHPC), where ACSS2 was normally expressed. Strikingly, ACSS2 KD prevented the incorporation of alcohol-derived heavy acetyl groups into histone acetylation (FIG. 23A). In contrast, in the same animal, vHPC incorporation of the heavy label was not affected (FIG. 23B). These in vivo data indicate that acetate derived from hepatic alcohol metabolism is transported to the brain and readily incorporated into histone acetylation. Notably, even though the bulk of alcohol metabolism takes place in the liver, alcohol fractions may also be converted to acetate in the brain via the enzymes catalase and CYP2E1 (Zimatkin et al., Alcohol. Clin. Exp. Res., 2006, 30:1500-1505). Therefore, the contribution of extracellular acetate-derived acetyl groups to histone acetylation in the brain was assessed. In mice intraperitoneally injected with 2 g/kg deuterated acetate ($d_3$-acetate), rapid label incorporation into brain histone acetylation was detected, at similar levels in both hippocampus and cortex (FIGS. 23C and 23D). Remarkably, relative labeling was highest at 30 minutes and returned to background levels at 4 hours post-injection, indicating rapid incorporation of acetate-derived acetyl groups as well as rapid turnover of brain histone acetylation (FIGS. 23C and 23D). Together, these data demonstrate that increased blood acetate from liver alcohol metabolism (FIG. 23E, left) fuels ACSS2-mediated dynamic histone acetylation in the brain (FIG. 23E, right).

Next, the functional relevance of alcohol-derived acetate for ACSS2-dependent histone acetylation in regulating hippocampal gene expression was examined (FIG. 23E, right). It was found that alcohol administration in wild type (WT) mice resulted in significant enrichment of H3K9ac and H3K27ac peaks genome-wide. Strikingly, this response was eliminated in ACSS2 KD animals significant levels of H3K9ac peaks and a significant amount of H3K27ac peaks failed to induce upon EtOH treatment in the dHPC. RNA-seq was then performed to characterize the transcriptional response and it was found that H3K9ac and H3K27ac drove gene expression in EtOH-treated WT animals genome-wide. However, in line with the ChIP-seq data, this response was markedly blunted in ACSS2 KD mice. Together, the in vivo findings strongly suggest that alcohol administration leads to increased histone acetylation and transcriptional activity in the dHPC in an ACSS2-dependent manner. Because alcohol and acetate have pleiotropic effects on brain circuitry and metabolism, an in vitro assay was then developed to more closely model the direct effects of exogenous acetate on gene expression. Isolated mouse primary hippocampal neurons were utilized to investigate the transcriptional response to supraphysiological levels of acetate (cells were cultured for one week after isolation and subsequently treated with 10 mM acetate for 24 hours) that mimics exogenous acetate influx during alcohol intoxication. Further, to determine the specific role of ACSS2 in transcriptional responses to acetate, a highly specific small molecule inhibitor of ACSS2 (ACSS2i) was employed (Mews et al., Nature, 2017, 546: 381-386; Comerford et al., Cell, 2014, 159:1591-1602).

In primary hippocampal neurons, acetate supplementation induced 3613 genes (FIG. 24A, FIG. 25A) that were, via Gene Ontology (GO) term analysis, involved in nervous system processes, including signal transduction and learning and memory (FIG. 25B, red). In contrast, acetate treatment resulted in down regulation of genes involved in immune system processes (FIG. 25B, lower in blue). In the presence of the ACSS2i, 2107 of the acetate-induced genes failed to become upregulated (FIGS. 24A and 24C), indicating that acetate-induced transcription relies heavily on the catalytic activity of ACSS2. Importantly, acetate-induced genes were not regulated by ACSS2i treatment in the absence of acetate (FIG. 24B). GO analysis of ACSS2i-sensitive upregulated genes showed enrichment for nervous system processes, behavior, and learning and memory (FIG. 24C, lower). Notably, these acetate-induced genes showed a remarkable overlap with genes upregulated by acute alcohol in the hippocampus in vivo (Mulligan et al., Alcohol. Clin. Exp. Res., 2011, 35:659-670) (38% of 214 alcohol-responsive hippocampal genes, FIG. 25C), strongly supporting the translational validity of the in vitro model.

Further analysis revealed that 40% of the ACSS2i-sensitive upregulated genes are acetylated in vivo (Mews et al., Nature, 2017, 546:381-386) (H3K9ac ChIP-seq, 908 out of 2107 ACSS2i-sensitive genes), and that direct binding of hippocampal ACSS2 (ChIP-seq) is promotor-proximal at baseline without any direct behavioral stimulation in vivo (Mews et al., Nature, 2017, 546:381-386) (FIG. 23D). GO analysis linked these genes to intricate plasticity-related mechanisms involving axonogenesis and voltage-gated ion channel activity (FIG. 24D). Correspondingly, motif analysis of ACSS2-targeted, acetate-induced, and ACSS2i-sensitive genes implicated the involvement of neuronal transcription factors—including E2F3 and NR5A2 (FIG. 24E)—that are linked to neurodifferentiation and the regulation of behavior by drugs of abuse (Cates et al., Biol. Psychiatry, 2018, 84:167-179; Stergiopoulos et al., Nat. Commun., 2016, 7:1-16).

Together, these findings strongly suggest that ACSS2 plays an important role in alcohol-related learning by coordinating alcohol-induced histone acetylation and gene expression (FIG. 23C). To test this behaviorally, ethanol conditioned place preference (CPP) was performed in WT and ACSS2 KD mice. In this paradigm, animals are exposed to neutral and rewarding stimuli in distinct compartments, differentiated by environmental cues. After conditioning, CPP is measured by allowing the animals access to both environments and measuring time spent in the alcohol-associated chamber. In WT mice, rewarding stimuli such as ethanol led to increased time spent in the drug-associated environment (Mann-Whitney, p=0.022). Importantly, the development of CPP depends on dorsal HPC spatial memory formation, and, accordingly, dorsal HPC lesions disrupt place conditioning. Strikingly, it was found that ethanol CPP was completely abolished in ACSS2 KD (dHPC) mice (Mann-Whitney p=0.184), indicating that alcohol-related associative memory formation depends on ACSS2. Taken together, the in vitro, in vivo, and behavioral findings show that ACSS2 is required for heavy labeled acetate incorporation into acetylated histones in the dorsal HPC, which drives memory-related gene expression and alcohol-related associative learning. These results establish ACSS2 as a promising candidate for therapeutic intervention in alcohol use disorders, in which memory of alcohol-associated environmental cues is a primary driver of craving and relapse even after protracted periods of abstinence.

Importantly, alcohol exposure not only disrupts epigenetic and transcriptional processes in the adult brain but is also linked to epigenetic dysregulation in the developing fetus (Veazey et al., Epigenetics Chromatin, 2015, 8:39; Starkman et al., Alcohol Research: Current Reviews, 2011, 34:293-305). In utero, alcohol is an environmental teratogen that affects neuro-developmental gene expression and can elicit numerous alcohol-associated postnatal disease phenotypes that are categorized as fetal alcohol spectrum disorder (FASD) (Mead et al., Front. Genet., 2014, 5:1-10). Recent investigation of alcohol-mediated epigenetic changes in utero implicated altered histone acetylation in FASD, but the underlying mechanisms are still unknown (Kim et al., Alcohol Alcohol., 2006, 41:126-132; Mandal et al., Int. J. Biol. Sci., 2017, 13:1100-1108).

Whether gestational alcohol exposure may influence histone acetylation in the developing fetal brain was explored via direct deposition of alcohol-derived acetyl groups onto histones. Using the established paradigm of heavy-labeled alcohol injections (2 mg/kg i.p.) followed by mass spectrometry on isolated histone proteins, the incorporation of alcohol metabolites (4 h post-injection) into the neuronal histone acetylation in gestating female mice (FIG. 26A) was confirmed, consistent with the previous results in males (FIGS. 21B and 21C). Then whether alcohol similarly affects dynamic histone acetylation in utero in the developing mid- and forebrain was investigated (E18.5) (FIG. 26B).

The fetal brain MS data show that—parallel to maternal labeling of neuronal histone acetylation—'binge drinking-like' alcohol exposure resulted in the deposition of alcohol-derived acetyl-groups onto histones in fetal fore- and midbrain at early neural development (FIG. 26B). Taken together, the results indicate that direct incorporation of alcohol-derived acetyl groups drives histone acetylation in the fetal brain, indicating an unanticipated potential mechanism for FASD etiology.

In the adult brain, epigenetic mechanisms that control gene expression play a key role in processing neural activity. The data provide the first evidence for dynamic signaling from liver alcohol metabolism directly to epigenetic regulation in neurons in vivo, via metabolite activation by neuronal ACSS2. In the hippocampus, alcohol-derived acetyl group incorporation may be of critical importance for alcohol-related associative learning, which encodes environmental cues associated with alcohol that drive craving, seeking, and consumption even after protracted periods of abstinence. Importantly, the findings suggest that other peripheral sources of physiological acetate—primarily the gut microbiome—may similarly affect neuronal histone acetylation and brain function, which may either control or foster other metabolic syndromes. Translational treatment strategies that target this *nexus* between peripheral metabolic activity and neuro-epigenetic regulation may pave the way for novel therapeutic interventions for alcohol use and other neuropsychiatric disorders.

Example 4: Small Molecule Inhibition of H3K3 Acetylation

Figure 27:
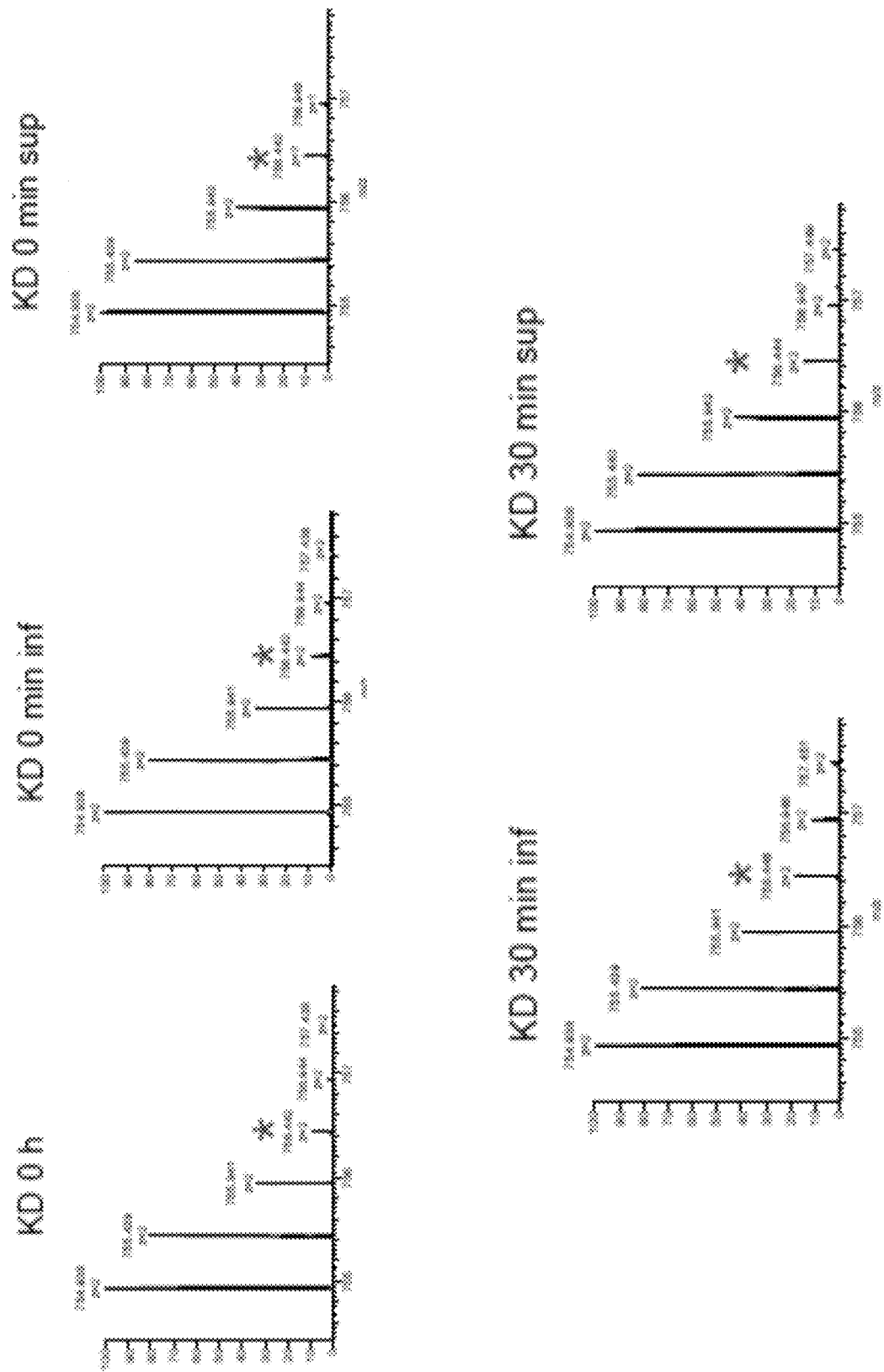
FIG. 27 depicts experimental results demonstrating the peptide H4 aa 4-17 with 3 acetyls (hippocampus).
Figure 28:
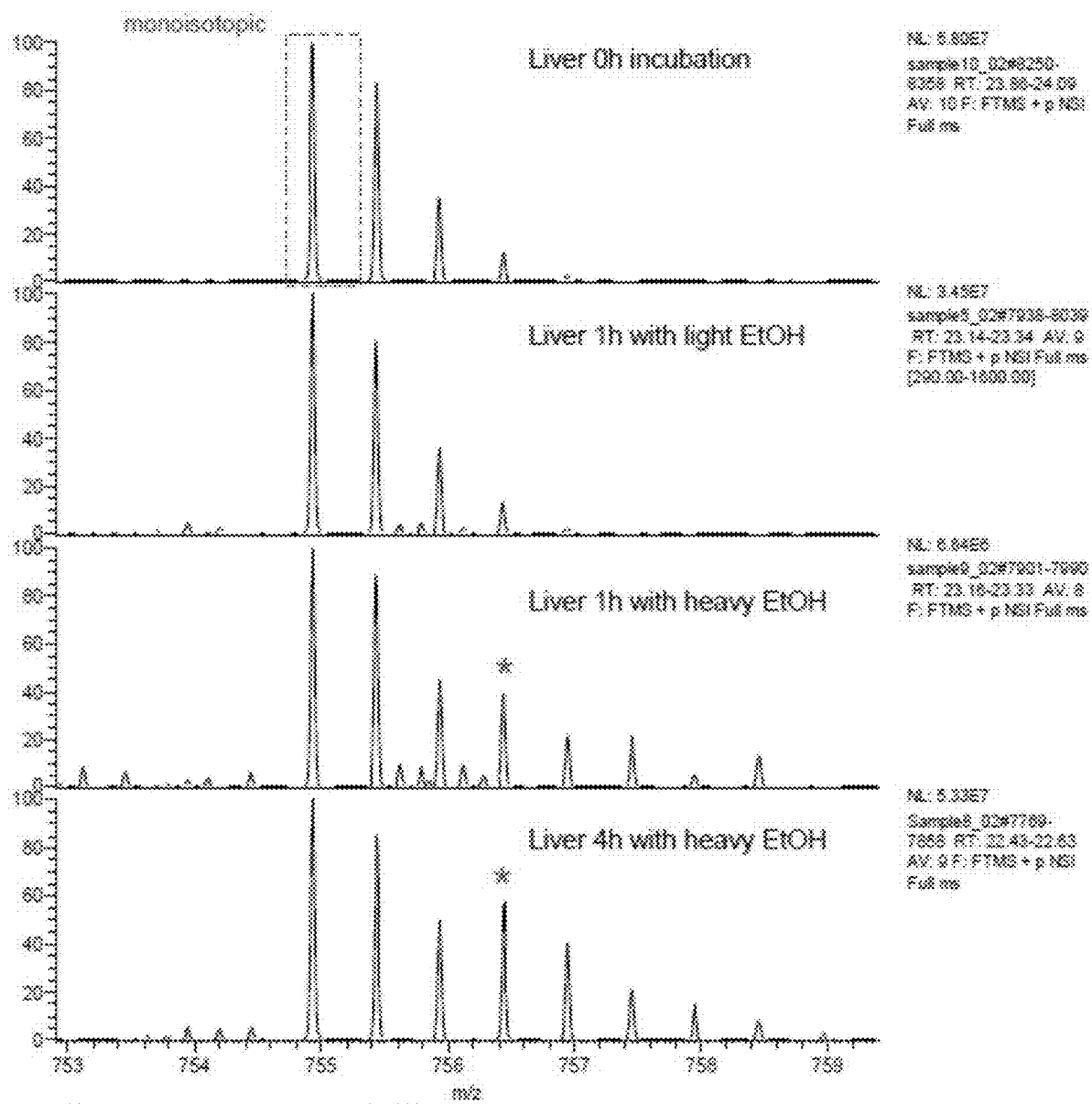
FIG. 28 depicts experimental results of SILAC-mass spec experiments.
Figure 29:
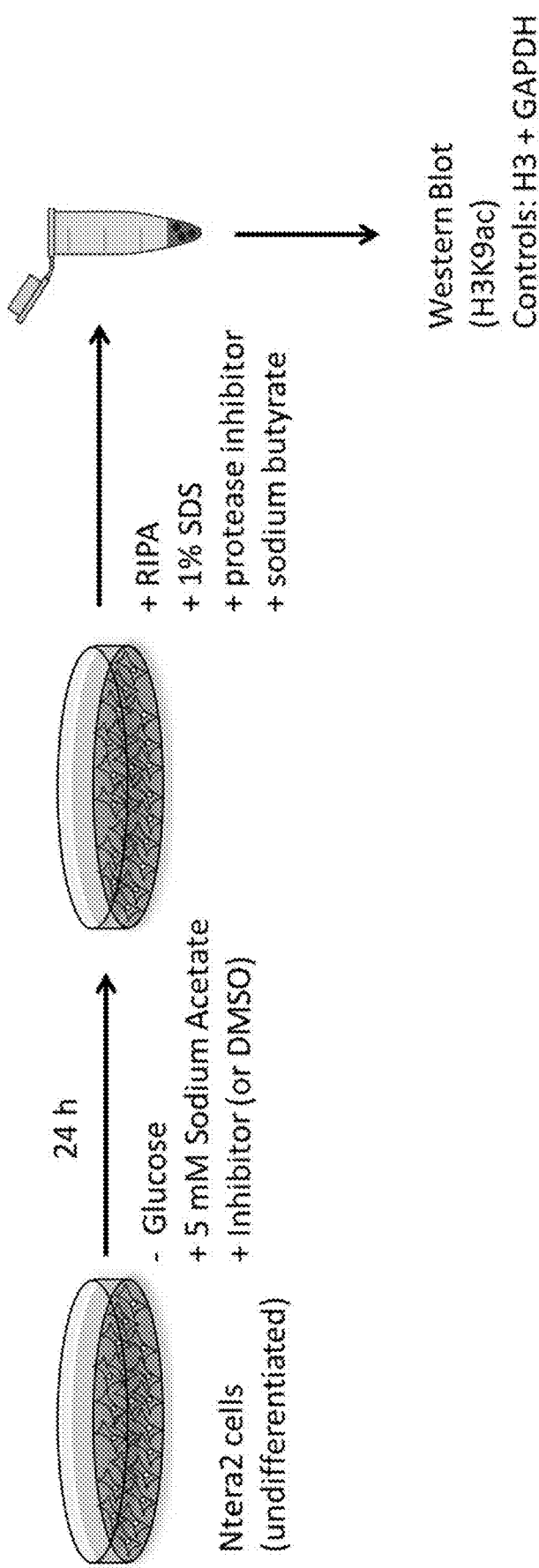
FIG. 29 depicts assay design to determine efficacy to reduce catalytic ACSS2 activity and histone H3 lysine 9 acetylation in vitro—Ntera2 cells were maintained in DMEM (Gibco) with 10% FBS and GlutaMAX (Gibco). Cells were treated for 24 hours with 5 mM sodium acetate in the absence of glucose and compound ADG-204, ADG-205, ADG-206, or vehicle (DMSO). Cells were lysed in RIPA buffer containing 50 mM Tris pH 8.0, 0.5 mM EDTA, 150 mM NaCl, 1% NP40, 1% SDS, supplemented with protease inhibitor cocktail (Life Technologies, number 78446) and 10 mM sodium butyrate. Protein concentration was determined by BCA protein assay (Life Technologies, number 23227), and equal amounts of protein were directly loaded onto polyacrylamide gels. Proteins were separated on 4-12% Bis-Tris polyacrylamide gels (NuPAGE). After transfer to nitrocellulose membrane, 3% BSA in TBS supplemented with 0.1% Tween 20 (TBST) was used to block the membrane at room temperature for 1 h. Primary antibodies were diluted in TBST and incubated at 4° C. overnight. The antibodies used were anti-H3 (Abcam ab1791), anti-H3K9ac (Abcam ab4441), anti-GAPDH (Fitzgerald Industries 10R-G109A). The membrane was washed three times with TBST, each for 10 min, followed by incubation with HRP-conjugated secondary antibodies at room temperature for 1 h, in TBST. The membrane was washed again three times and imaged with a Fujifilm LAS-4000 imager.
Figure 30:
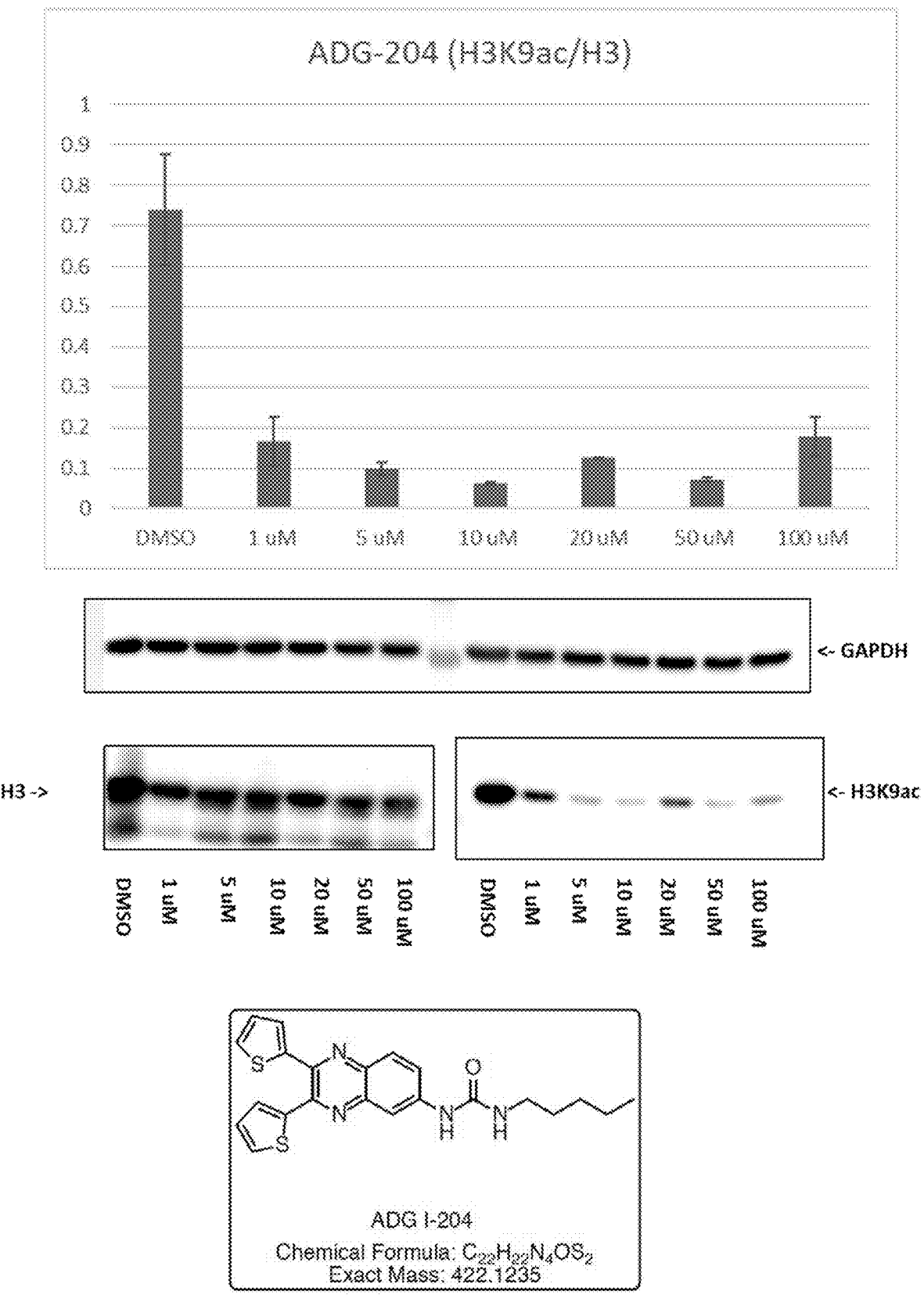
FIG. 30 depicts the chemical structure and activity of ADG-204.
Figure 31:
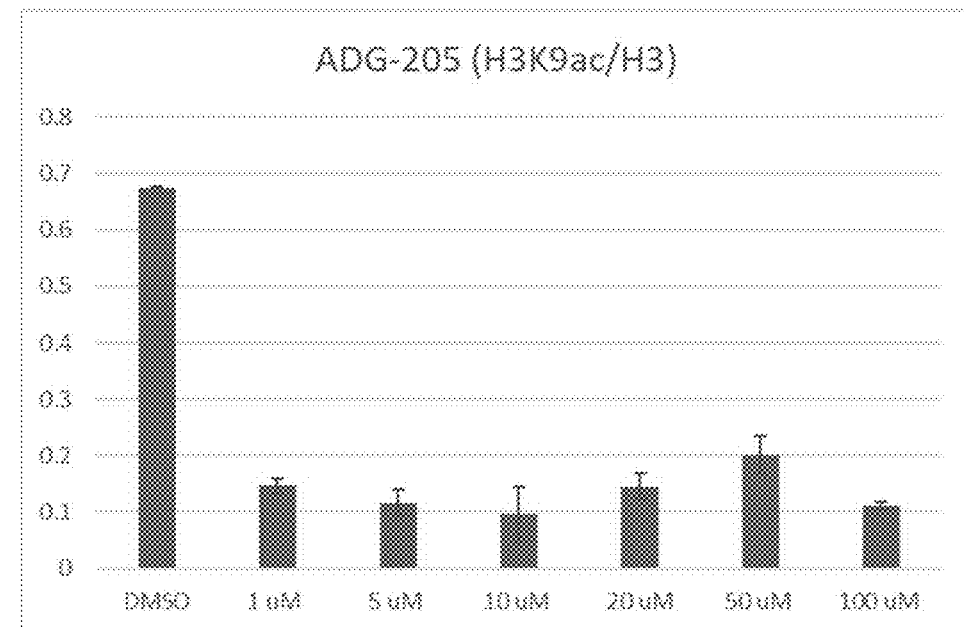
FIG. 31 depicts the chemical structure and activity of ADG-205.
Figure 31:
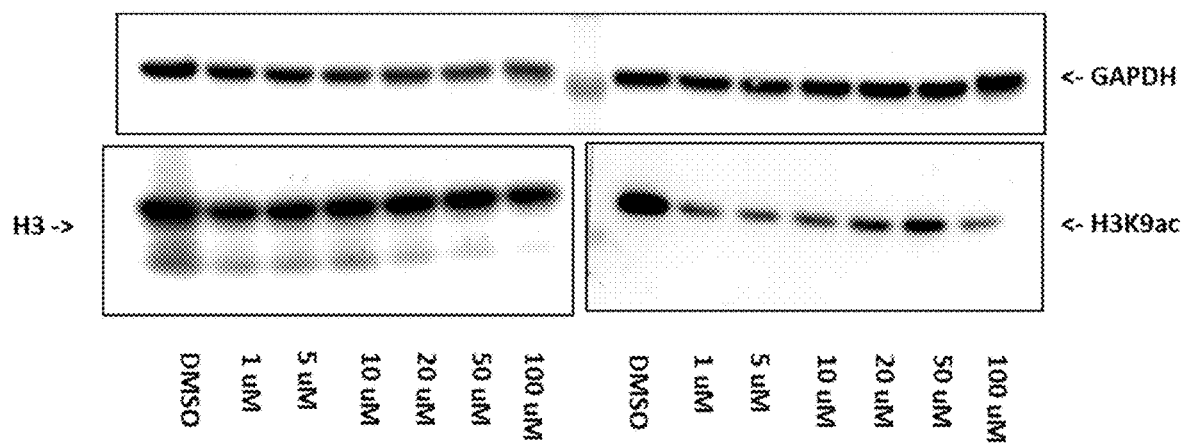
Figure 31:
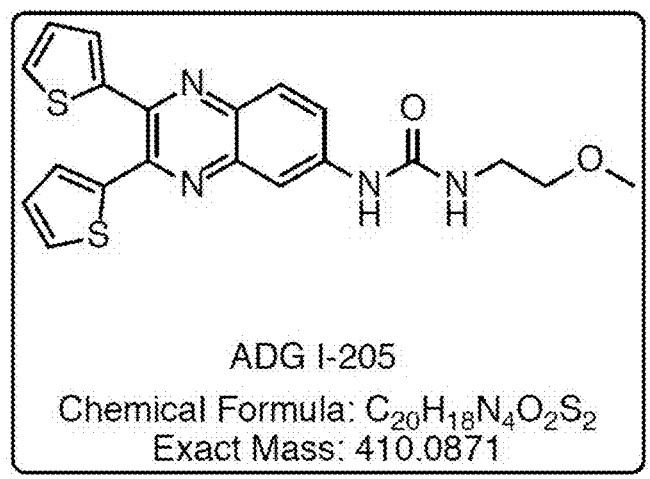
Figure 32:
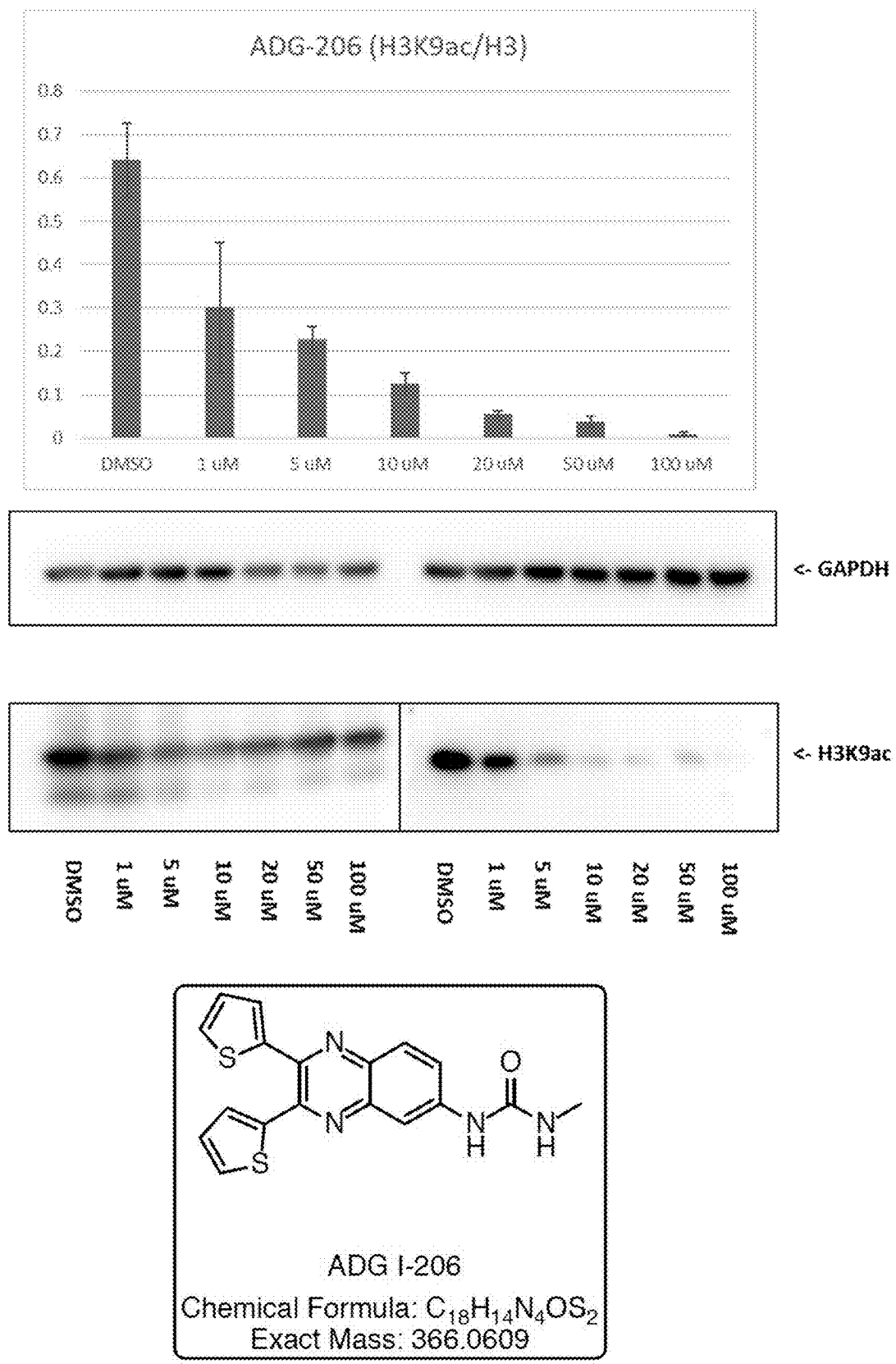
FIG. 32 depicts the chemical structure and activity of ADG-206.

Undifferentiated Ntera2 cells were treated with inhibitor for 24 hours with ADG-204, ADG-205 or ADG-206 (FIG. 27). Western blots were used to determine the levels H3K3ac after treatment with ADG-204 (FIG. 28), ADG-205 (FIG. 29) or ADG-206 (FIG. 30).

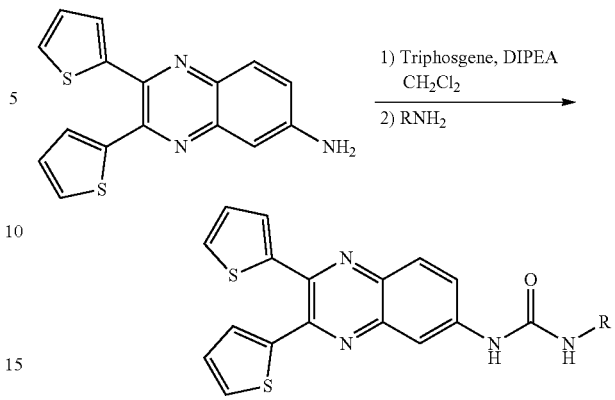

ADG-I-206: 1-(2,3-di(thiophen-2-yl)quinoxalin-6-yl)-3-methylurea (R=Me)

To a stirring solution of 2,3-di(thiophen-2-yl)quinoxalin-6-amine (333 mg, 1.08 mmol, 1 eq) in anhydrous $CH_2Cl_2$ (5.4 mL) was added N,N-diisopropylethylamine (0.375 mL, 2.15 mmol, 2 eq) followed by triphosgene (105 mg, 0.36 mmol, 0.33 eq) in anhydrous $CH_2Cl_2$ (5.4 mL) to give a red-orange solution. The reaction mixture was allowed to stir for 4 h at room temperature, then methylamine (2M in THF, 0.67 mL, 1.35 mmol, 1.25 eq) was added dropwise. The reaction mixture was then allowed to stir for 16 h at room temperature. A stream of argon was blown over the reaction mixture to remove the solvent and any excess phosgene, and the residue obtained was purified by flash chromatography (80% EtOAc/Hexanes) to afford the title compound as a yellow solid (196 mg, 50%). $^1$H NMR (500 MHz, DMSO-$d_6$) δ 9.17 (s, 1H), 8.24 (d, J=2.4 Hz, 1H), 7.90 (d, J=9.0 Hz, 1H), 7.84-7.54 (m, 3H), 7.16 (dd, J=13.9, 3.7 Hz, 2H), 7.12-7.06 (m, 2H), 6.29 (q, J=4.6 Hz, 1H), 2.71 (d, J=4.6 Hz, 3H). $^{13}$C NMR (126 MHz, DMSO) δ 155.51, 146.08, 143.15, 142.62, 141.39, 141.19, 141.10, 135.76, 129.65, 129.00, 128.91, 128.72, 128.66, 127.77, 127.65, 123.80, 111.56, 26.29. HRMS (ESI) m/z calc'd for $C_{18}H_{15}N_4OS_2$ [M+H]$^+$ 367.0687, found 367.0689

ADG-I-205: 1-(2,3-di(thiophen-2-yl)quinoxalin-6-yl)-3-(2-methoxyethyl)urea (R=MeOCH$_2$CH$_2$)

To a stirring solution of 2,3-di(thiophen-2-yl)quinoxalin-6-amine (337 mg, 1.09 mmol, 1 eq) in anhydrous $CH_2Cl_2$ (5.5 mL) was added N,N-diisopropylethylamine (0.38 mL, 2.18 mmol, 2 eq) followed by triphosgene (107 mg, 0.36 mmol, 0.33 eq) in anhydrous $CH_2Cl_2$ (5.5 mL) to give a red-orange solution. The reaction mixture was allowed to stir for 4 h at room temperature, then 2-methoxyethylamine (0.12 mL, 1.36 mmol, 1.25 eq) was added dropwise. The reaction mixture was then allowed to stir for 16 h at room temperature. A stream of argon was blown over the reaction mixture to remove the solvent and any excess phosgene, and the residue obtained was purified by flash chromatography (70% EtOAc/Hexanes) to afford the title compound as a yellow solid (196 mg, 50%). $^1$H NMR (500 MHz, DMSO-$d_6$) δ 9.19 (s, 1H), 8.23 (d, J=2.4 Hz, 1H), 7.91 (d, J=9.1 Hz, 1H), 7.76 (ddd, J=9.7, 5.1, 1.1 Hz, 2H), 7.68 (dd, J=9.1, 2.4 Hz, 1H), 7.18 (dd, J=3.7, 1.2 Hz, 1H), 7.15 (dd, J=3.7, 1.1 Hz, 1H), 7.10 (ddd, J=6.9, 5.1, 3.7 Hz, 2H), 6.47 (t, J=5.6 Hz, 1H), 3.43 (t, J=5.4 Hz, 2H), 3.33 (t, J=5.5 Hz, 2H), 3.30

(s, 3H). $^{13}$C NMR (126 MHz, DMSO) δ 154.83, 146.12, 143.21, 142.42, 141.37, 141.17, 141.07, 135.79, 129.68, 129.02, 128.94, 128.80, 128.68, 127.77, 127.65, 123.70, 111.55, 71.06, 57.90, 38.87. HRMS (ESI) m/z calc'd for $C_{20}H_{19}N_4O_2S_2$ [M+H]$^+$ 411.0949, found 411.0926.

ADG-I-204: 1-(2,3-di(thiophen-2-yl)quinoxalin-6-yl)-3-penlylurea (R=n-$C_5H_1$)

To a stirring solution of 2,3-di(thiophen-2-yl)quinoxalin-6-amine (1.04 g, 3.36 mmol, 1 eq) in anhydrous $CH_2Cl_2$ (34 mL) was added N,N-diisopropylethylamine (1.17 mL, 6.72 mmol, 2 eq) followed by triphosgene (329 mg, 1.11 mmol, 0.33 eq) in anhydrous $CH_2Cl_2$ (1 mL, final concentration 0.1M) to give a red-orange solution. The reaction mixture was allowed to stir for 4 h at room temperature, then amylmine (0.49 mL, 4.20 mmol, 1.25 eq) was added dropwise. The reaction mixture was then allowed to stir for 16 h at room temperature. A stream of argon was blown over the reaction mixture to remove the solvent and any excess phosgene, and the residue obtained was purified by flash chromatography (50-60% EtOAc/Hexanes) to afford the title compound as a yellow solid (872 mg, 61%). $^1$H NMR (500 MHz, DMSO-d$_6$) δ 9.07 (s, 1H), 8.23 (d, J=2.3 Hz, 1H), 7.90 (d, J=9.0 Hz, 1H), 7.76 (dd, J=9.7, 5.0 Hz, 2H), 7.69 (dd, J=9.1, 2.4 Hz, 1H), 7.16 (dd, J=16.6, 3.6 Hz, 2H), 7.13-7.05 (m, 2H), 6.41 (t, J=5.7 Hz, 1H), 3.14 (q, J=6.5 Hz, 2H), 1.48 (p, J=7.1 Hz, 2H), 1.40-1.11 (m, 4H, overlapping with grease), 0.90 (t, J=6.7 Hz, 3H). $^{13}$C NMR (126 MHz, DMSO) δ 154.87, 146.09, 143.13, 142.59, 141.40, 141.19, 141.08, 135.75, 129.67, 129.00, 128.91, 128.74, 128.66, 127.77, 127.65, 123.77, 111.49, 29.26, 28.55, 21.83, 13.91. HRMS (ESI) m/z calc'd for $C_{22}H_{23}N_4OS_2$ [M+H]$^+$ 423.1313, found 423.1336.

Example 5: Inhibition of Acetyl-CoA Affects Histone Acetylation and Hippocampal Memory To investigate the role of ACSS2 in the adult hippocampus, ACSS2 expression is attenuated in the dorsal hippocampus by treatment with small molecule ACSS2 inhibitors ADG-204, ADG-205, ADG-206 or ADG-207.

ADG-207

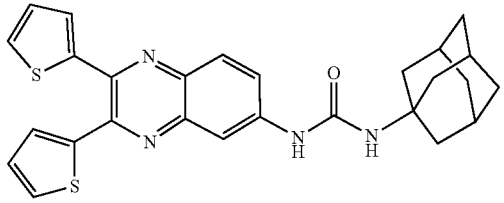

Compared to control-treated mice, Mice treated with an ACSS2 inhibitor show similar levels of locomotion, coordination, body weight, and anxiety-related thigmotaxis during open field exploration; therefore, ACSS2 inhibition does not cause gross behavioral alterations.

To assess hippocampus-dependent spatial memory, an object-location memory paradigm is used. Animals explore three different objects during training, and long-term memory is tested by re-exposure 24 hours later with one object moved to a different location. In training, control and inhibitor treated mice show no difference in exploration. During memory retrieval, control mice show increased exploration of the object that had been moved. By contrast, mice treated with an ACSS2 inhibitor are impaired in spatial object memory and display a lower discrimination index. Mice treated with an ACSS2 show reduced total object exploration during the test, suggesting diminished novelty associated with intact recognition of the objects from the training session.

As a control experiment, control mice or mice treated with an ACSS2 inhibitor are subjected to a contextual fear conditioning paradigm. During the 24-hour test session, there are no significant difference in the amount of freezing behavior between control mice or mice treated with an ACSS2 inhibitor suggesting that the ventral hippocampus successfully mediates context-shock association. Overall, ACSS2 has a critical role in dorsal hippocampus-mediated long-term spatial memory.

Example 6: Inhibition of Acetyl-CoA Synthetase Prevents the Incorporation of Alcohol-Derived Heavy Acetyl Groups into Histone Acetylation To investigate the direct role of ACSS2 in alcohol-dependent acetylation in the brain, mice are treated with an ACSS2 inhibitor, ADG-204, ADG-205, ADG-206, or ADG-207. Treatment with an ACSS2 inhibitor prevents the incorporation of alcohol-derived heavy acetyl groups into histone acetylation. In contrast, in control mice, vHPC incorporation of the heavy label is not affected. Thus, acetate derived from hepatic alcohol metabolism is transported to the brain and readily incorporated into histone acetylation.

Example 7: Synthesis of ADG-207: 1-((1S,3s)-adamantan-1-yl)-3-(2,3-di(thiophen-2-yl)quinoxalin-6-yl)urea (R=1-adamantyl)

To a stirring solution of 2,3-di(thiophen-2-yl)quinoxalin-6-amine (32 mg, 0.1 mmol, 1 eq) in anhydrous $CH_2Cl_2$ (0.6 mL) was added N,N-diisopropylethylamine (0.04 mL, 0.2 mmol, 2 eq) followed by triphosgene (10 mg, 0.034 mmol, 0.33 eq) in anhydrous $CH_2Cl_2$ (0.6 mL, final concentration 0.08 M) to give a red-orange solution. The reaction mixture was allowed to stir for 4 h at room temperature, then 1-adamantanamine (0.49 mL, 4.20 mmol, 1.25 eq) was added dropwise. The reaction mixture was then allowed to stir for 16 h at room temperature. A stream of argon was blown over the reaction mixture to remove the solvent and any excess phosgene, and the residue obtained was purified by flash chromatography (40% EtOAc/Hexanes) to afford the title compound contaminated with 1,1-di-adamantanylurea. The product was re-purified by flash chromatography twice to afford the analytically pure title compound as a yellow solid (4 mg, 8%)$^1$H NMR (500 MHz, DMSO-d$_6$) δ 8.91 (s, 1H), 8.20 (d, J=2.4 Hz, 1H), 7.89 (d, J=9.1 Hz, 1H), 7.76 (ddd, J=9.2, 5.1, 1.2 Hz, 2H), 7.61 (dd, J=9.1, 2.4 Hz, 1H), 7.19 (dd, J=3.7, 1.2 Hz, 1H), 7.14 (dd, J=3.7, 1.2 Hz, 1H), 7.10 (ddd, J=11.0, 5.0, 3.6 Hz, 2H), 6.15 (s, 1H), 2.06 (s, 3H), 1.99 (d, J=2.9 Hz, 6H), 1.66 (t, J=3.1 Hz, 6H). $^{13}$C NMR (126 MHz, DMSO) δ 153.55, 146.09, 143.03, 142.57, 141.48, 141.25, 141.06, 135.67, 129.73, 128.98, 128.87, 128.76, 128.65, 127.77, 127.64, 123.66, 111.24, 50.15, 41.50, 36.00, 28.88. HRMS (ESI) m/z calc'd for $C_{27}H_{27}N_4OS_2$ [M+H]$^+$ 487.1626, found.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating a memory-related disease or disorder associated with acetyl-CoA synthetase 2 (ACSS2), the method comprising administering a composition comprising an inhibitor of ACSS2 to a subject in need thereof;

wherein the inhibitor of ACSS2 is a small molecule;

wherein the small molecule is selected from the group consisting of a compound having the structure of:

Formula (4)

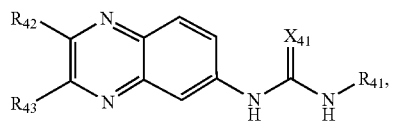

wherein $X_{41}$ is selected from the group consisting of O and S;

$R_{41}$ is selected from the group consisting of alkyl, cycloalkyl, heterocyclyl, unsubstituted aryl, heteroaryl, and combinations thereof, wherein $R_{41}$ may be optionally substituted; and $R_{42}$ and $R_{43}$ are each independently selected from the group consisting of phenyl and thiophenyl; and

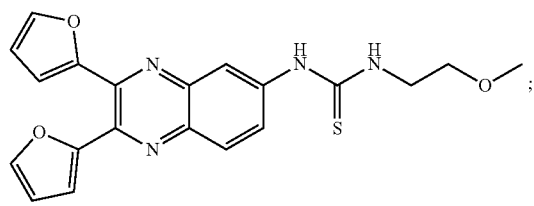 [SMILES: COCCNC(=S)Nc1ccc2nc(-c3ccco3)c(-c3ccco3)nc2c1]

wherein the memory-related disease or disorder associated with acetyl-CoA synthetase 2 (ACSS2) is an addiction to at least one selected from the group consisting of alcohol, tobacco, cocaine, and opioids.

2. The method of claim 1, wherein the small molecule is selected from the group consisting of a compound having the structure Formula (4)

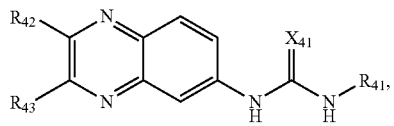

wherein, $X_{41}$ is selected from the group consisting of O and S;

$R_{41}$ is selected from the group consisting of alkyl, cycloalkyl, heterocyclyl, heteroaryl, and combinations thereof, wherein $R_{41}$ may be optionally substituted; and $R_{42}$ and $R_{43}$ are each independently selected from the group consisting of phenyl and thiophenyl; and

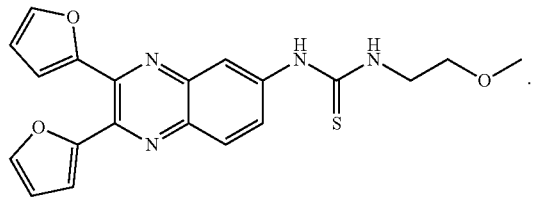 [SMILES: COCCNC(=S)Nc1ccc2nc(-c3ccco3)c(-c3ccco3)nc2c1]

3. The method of claim 1, wherein the small molecule is selected from the group consisting of

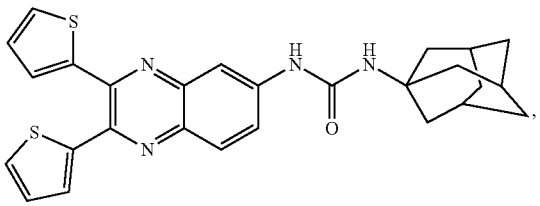

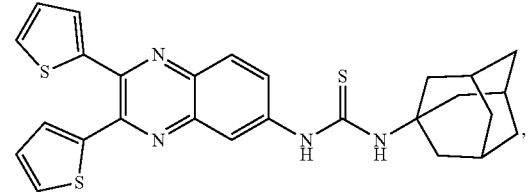

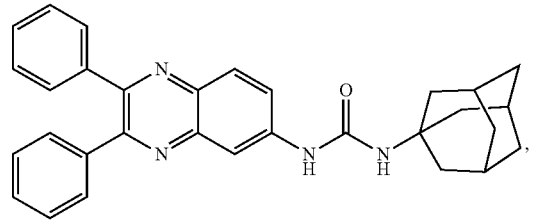

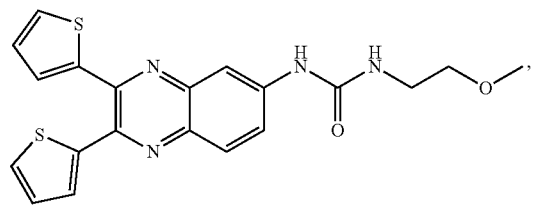

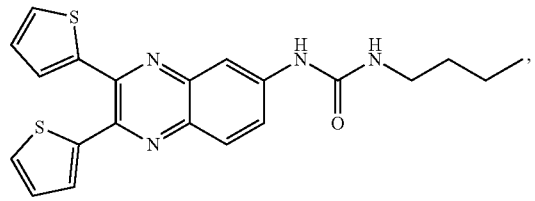

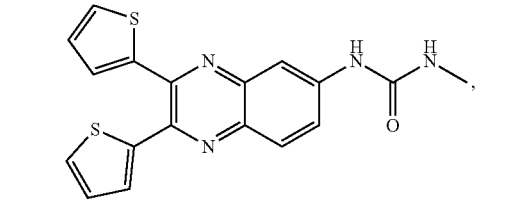

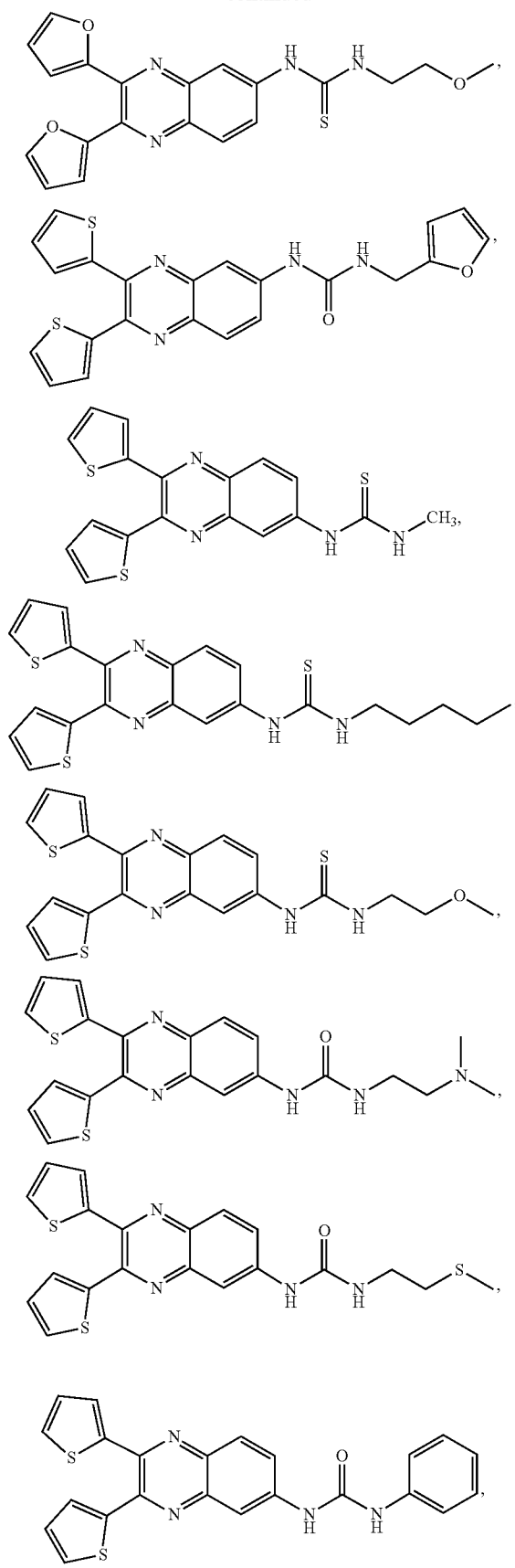

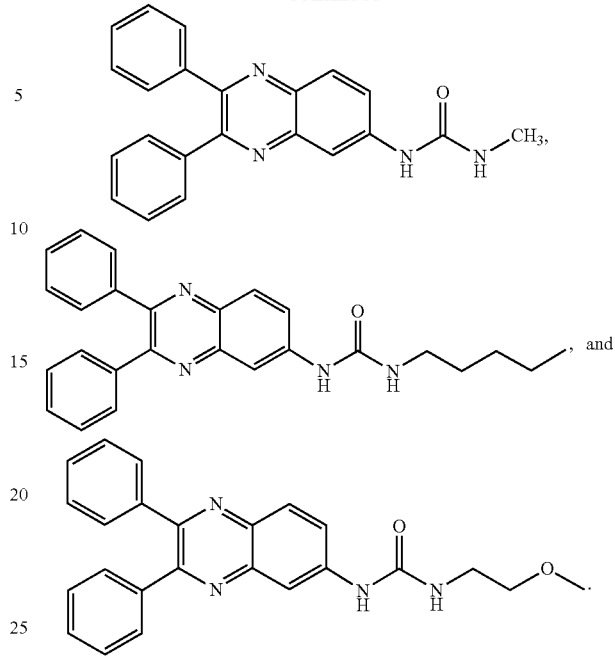

4. A compound having the structure of:

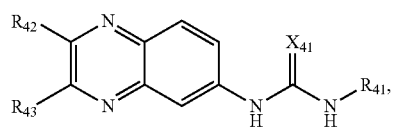

Formula (4)

wherein $X_{41}$ is selected from the group consisting of O and S;

$R_{41}$ is selected from the group consisting of adamantly, furanyl, heterocyclyl, and combinations thereof, wherein $R_{41}$ may be optionally substituted; and $R_{42}$ and $R_{43}$ are each thiophenyl.

5. The compound of claim 4, wherein the compound having the structure of Formula (4) is selected from the group consisting of

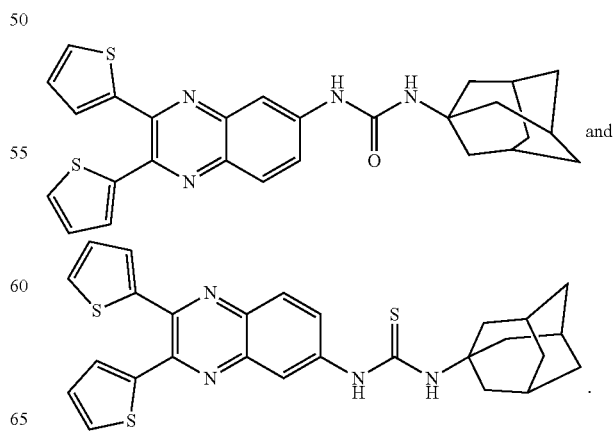

6. The method of claim 1, wherein the memory-related disease or disorder associated with acetyl-CoA synthetase 2 (ACSS2) is an addiction to alcohol.

7. The method of claim 1, wherein the memory-related disease or disorder associated with acetyl-CoA synthetase 2 (ACSS2) is an addiction to cocaine.

8. The method of claim 1, wherein the memory-related disease or disorder associated with acetyl-CoA synthetase 2 (ACSS2) is an addiction to tobacco.

9. The method of claim 1, wherein the memory-related disease or disorder associated with acetyl-CoA synthetase 2 (ACSS2) is an addiction to opioids.

10. The compound of claim 4, wherein the heterocyclyl is selected from the group consisting of morpholinyl, piperidnyl, pyrrolidinyl, and any combination thereof.

11. The compound of claim 4, wherein $R_{41}$ is selected from the group consisting of adamantly, morpholinyl, piperidnyl, pyrrolidinyl, furanyl, and combinations thereof, wherein $R_{41}$ may be optionally substituted.

* * * * *